(12) United States Patent
Fässler et al.

(10) Patent No.: US 6,451,973 B1
(45) Date of Patent: Sep. 17, 2002

(54) ANILINOPEPTIDE DERIVATIVES

(75) Inventors: Alexander Fässler, Arlesheim; Guido Bold, Gipf-Oberfrick; Hans-Georg Capraro, Rheinfelden, all of (CH); Marc Lang, Mulhouse (FR)

(73) Assignee: Novatis AG, Basel (CH)

( * ) Notice: Subject to any disclaimer, the term of this patent is extended or adjusted under 35 U.S.C. 154(b) by 0 days.

(21) Appl. No.: 09/214,959

(22) PCT Filed: Jul. 16, 1997

(86) PCT No.: PCT/EP97/03804

§ 371 (c)(1),
(2), (4) Date: Feb. 1, 1999

(87) PCT Pub. No.: WO98/03476

PCT Pub. Date: Jan. 29, 1998

(30) Foreign Application Priority Data

Jul. 17, 1996 (CH) .............................................. 1788/96

(51) Int. Cl.$^7$ ................................................. C07K 5/08
(52) U.S. Cl. ............................ 530/331; 514/18; 514/19
(58) Field of Search ............................. 530/331; 514/18, 514/19

(56) References Cited

U.S. PATENT DOCUMENTS

| | | | |
|---|---|---|---|
| 4,556,654 A | 12/1985 | Showalter et al. | 514/222 |
| 5,461,067 A | 10/1995 | Norbeck et al. | 514/333 |
| 5,621,109 A | 4/1997 | Norbeck et al. | 548/182 |
| 5,753,652 A | * 5/1998 | Fassler | 514/227.5 |
| 5,807,891 A | 9/1998 | Bold et al. | 514/487 |
| 5,849,911 A | * 12/1998 | Fassler | 544/335 |

FOREIGN PATENT DOCUMENTS

| | | |
|---|---|---|
| EP | 486 948 A2 | 5/1992 |
| EP | 0 604 368 A1 | 6/1994 |
| WO | WO 93/18006 | 9/1993 |
| WO | WO 94/14436 | 7/1994 |
| WO | WO 94 19332 A | 9/1994 |
| WO | 94/19332 * | 9/1994 |
| WO | 98/03476 * | 1/1998 |

OTHER PUBLICATIONS

Young J. Med. Chem. 35, 1702, 1992.*
Steven D. Young et al., Jour. of Medicinal Chemistry, vol. 35, No. 10, pp. 1702–1709 (1992).
Sham et al., J.Chem.Soc.Chem.Commun., p. 1052 (1993).
Fässler et al., J.Med.Chem., vol. 39, pp. 3203–3216 (1996).

* cited by examiner

*Primary Examiner*—Christopher S. F. Low
*Assistant Examiner*—David Lukton

(57) ABSTRACT

The invention relates to compounds of the formula I,

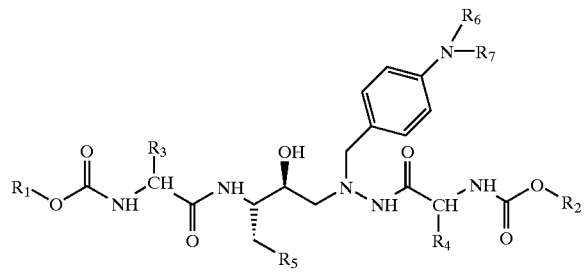

(I)

in which $R_1$ and $R_2$ are, independently of each other, lower alkyl or lower alkoxy-lower alkyl;

$R_3$ and $R_4$ are, independently of each other, sec-lower alkyl or tert-lower alkyl;

$R_5$ is phenyl or cyclohexyl; and $R_6$ and $R_7$ are, independently of each other, lower alkyl, or, together with the linking nitrogen atom, pyrrolidino, piperidino, 4-lower alkylpiperidino, 1,2,4-triazol-1-yl or 1,2,4-triazol-4-yl;

or a salt thereof, provided that at least one salt-forming group is present.

These compounds are inhibitors of HIV protease and are therefore suitable, for example, for treating AIDS or its preliminary stages.

12 Claims, No Drawings

ANILINOPEPTIDE DERIVATIVES

The invention relates to heterocyclic anilinobenzylazahexane derivatives which can be employed as substrate isosters of retroviral aspartate proteases, to salts thereof, to processes for preparing these compounds and their salts, to pharmaceutical preparations which comprise these compounds or salts thereof, and to the use of these compounds or of salts thereof (either alone or in combination with other active compounds which are effective against retroviruses) for the therapeutic or diagnostic treatment of a human or animal body or for producing pharmaceutical preparations.

BACKGROUND TO THE INVENTION

According to UN estimates, approximately 28 million people are infected with the "human immunodeficiency virus" i.e. HIV-1 or HIV-2. In infected patients, the disorder leads, by way of preliminary stages such as ARDS, and with very few exceptions, to a manifest disease of the immune system which is termed "acquired immunodeficiency syndrome" or AIDS. In what is by far the overwhelming majority of cases, this disease leads, sooner or later, to the death of the infected patient.

For treating retroviral diseases such as AIDS, use has hitherto been made primarily of inhibitors of reverse transcriptase, an enzyme which is active in converting retroviral RNA into DNA, such as 3'-azido-3'-deoxythymidine (AZT) or dideoxyinosine (DDI), and also trisodium phosphonoformate, ammonium 21-tungsto-9-antimoniate, 1-β-D-ribo-furanosyl-1,2,4-triazole-3-carboxamide and dideoxycytidine, and also adriamycin. In addition to this, there have been experiments to introduce the T4 cell receptor, which is present in the human body on particular cells of the immune system and is responsible for anchoring and introducing infectious virus particles into these cells. and consequently for their ability to infect, into the body, for example as a recombinant molecule or as a molecular fragment. This would thereby block viral binding sites so that the virions were no longer able to bind to the cells. Use is also being made of compounds, such as polymannoacetate, which employ other means to prevent the virus penetrating the cell membrane.

Saquinavir [N-tert-butyldecahydro-2-[2(R)-hydroxy-4-phenyl-3(S)-[[N- 2-quinolylcarbonyl-L-asparagnyl]amino] butyl]-(4aS,8aS)-isoquinoline-3(S)-carboxamide (Ro 31-8959); Hoffmann LaRoche] was the first inhibitor of so-called retroviral aspartate protease to be authorized for controlling the infection. Others have followed since then (Indinavir from Merck and Ritonavir from Abbott).

In addition, development is proceeding on a number of other inhibitors of retroviral aspartate protease, which is an enzyme whose function can be characterized as follows:

In the AIDS viruses, i.e. HIV-1 and HIV-2, and in other retroviruses, for example corresponding viruses in cats (FIV) and monkeys (SIV), an aspartate protease, such as the HIV protease, effects proteolytic maturation of the viral core proteins, for example. No infectious viral particles can be formed without this proteolytic maturation. The central role of the said aspartate proteases, such as HIV-1 protease or HIV-2 protease, in virus maturation, and experimental results obtained, for example, with infected cell cultures, have made it seem likely that effective prevention of the maturation step which is brought about by this protease would prevent the assembly of mature virions in vivo. As a consequence, inhibitors of this protease can be employed therapeutically.

The object of the present invention is to make available a novel type of compound which is endowed, in particular, with a pronounced inhibitory effect on viral multiplication in cells, with a high degree of antiviral activity against a large number of viral strains including those which are resistant to known compounds such as Saquinavir, Ritonavir and Indinavir, and with particularly favorable pharmacological properties, for example good pharmacokinetics, such as high bioavailability and/or high blood levels, and/or high selectivity.

EP 0 604 368 mentions a genus of compounds with HIV protease inhibiting activity—however, neither are the compounds of the present invention mentioned therein, nor are there any hints to the advantageous properties of the compounds of the formula I in the present disclosure.

COMPLETE DESCRIPTION OF THE INVENTION

The azahexane derivatives according to the invention are compounds of the formula I,

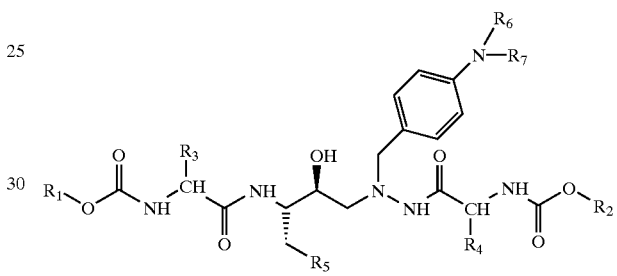

(I)

in which
$R_1$ and $R_2$ are, independently of each other, lower alkyl or lower alkoxy-lower alkyl;
$R_3$ and $R_4$ are, independently of each other, sec-lower alkyl or tert-lower alkyl;
$R_5$ is phenyl or cyclohexyl; and
$R_6$ and $R_7$ are, independently of each other, lower alkyl, or, together with the linking nitrogen atom, pyrrolidino, piperidino, 4-lower alkylpiperidino, 1,2,4-triazol-1-yl or 1,2,4-triazol-4-yl;
or a salt thereof, provided that at least one salt-forming group is present.

These compounds possess unexpectedly good, and surprisingly positive, pharmacological properties, as explained in detail below, and are relatively simple to synthesize.

Within the context of the present disclosure, the general terms which are used above and in that which follows preferably have the following meanings unless otherwise indicated:

The prefix "lower" designates a radical having not more than 7, in particular not more than 4, carbon atoms, with it being possible for the radicals concerned to be unbranched or to be branched once or more than once.

Lower alkyl and $C_1$–$C_4$alkyl are, in particular, tert-butyl, sec-butyl, iso-butyl, n-butyl, isopropyl, n-propyl, ethyl or, in particular, methyl.

Insofar as compounds, salts and the like are referred to in the plural, this also always means one compound, one salt or the like.

Any asymmetric carbon atoms which may be present, for example the carbon atoms which are linked to the radicals $R_3$ and $R_4$, can be present in the (R), (S) or (R,S)

configuration, preferably in the (R) or (S) configuration, with the (S) configuration being particularly preferred in the case of the carbon atoms in compounds of the formula I which carry the radical $R_3$ and/or the radical $R_5$. Consequently, the present compounds can exist as isomeric mixtures or as pure isomers, preferably as an enantiomerically pure diastereomer.

Lower alkoxy-lower alkyl is preferably $C_1$–$C_4$alkoxy-lower alkyl, in which the alkyl radical can be branched or unbranched, and is, in particular, ethoxyethyl or methoxyethyl.

Sec-lower alkyl or tert-lower alkyl is, in particular, sec-butyl, tert-butyl or isopropyl.

Pyrrolidino is pyrrolidin-1-yl. Piperidino is piperidin-1-yl. 4-Lower alkylpiperidino is, in particular, N-methylpiperidin-4-yl.

Preferably, the compounds of the formula I have the formula Ia,

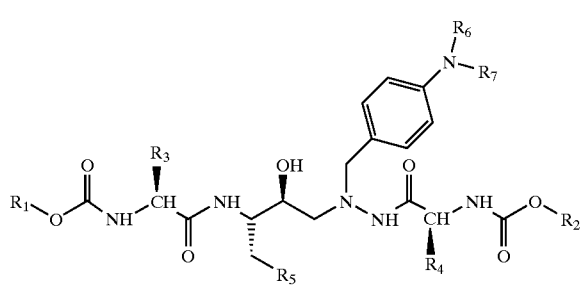

(Ia)

in which the radicals are as defined above or below.

Salts are first and foremost the pharmaceutically utilizable salts of compounds of the formula I.

These salts are formed, for example, from compounds of the formula I having a basic p-$R_6R_7N$—($C_6H_5$)—$CH_2$- carrying nitrogen atom as acid addition salts of strong acids, with strong acids preferably being understood to be inorganic acids, for example hydrohalic acid, such as hydrochloric acid, sulfuric acid or phosphoric acid, or strong organic sulfonic, sulfo or phospho acids, or N-substituted sulfamic acids (preferably: pKa<1). When basic heterocyclyl radicals, such as piperidino or 4-lower alkylpiperidino, are present, other salts can exist, depending on the base strength, which the skilled person can readily estimate or find out. These salts include, in particular, acid addition salts with organic or inorganic acids, in particular the pharmaceutically utilizable salts. Examples of suitable inorganic acids are, depending on the base strength of the corresponding compound of the formula I, hydrohalic acids, such as hydrochloric acid; sulfuric acid; or phosphoric acid. Examples of suitable organic acids are carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methyl maleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, glucuronic acid, galacturonic acid, methane-or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propylsulfamic acid, or other organic protonic acids, such as ascorbic acid.

Pharmaceutically unsuitable salts, for example picrates or perchlorates, can also be used for isolation or purification purposes. It is only the pharmaceutically utilizable salts or the free compounds (if desired in the form of pharmaceutical preparations) which are used therapeutically and which are therefore preferred.

As a consequence of the close relationship between the novel compounds in free form and in the form of their salts, including also those salts which can be used as intermediates, for example in the purification of the novel compounds or for the purpose of identifying them, the free compounds are, where applicable, also to be understood, both above and in that which follows, as being, analogously and appropriately, the corresponding salts.

The compounds of the formula I possess valuable pharmacological properties. They possess antiretroviral activity, in particular against the HIV-1 and HIV-2 viruses, which are regarded as the causative agents of AIDS, and can surprisingly have synergistic effects in combination with other compounds which are effective against retroviral aspartate proteases. The compounds of the formula I are inhibitors of retroviral aspartate proteases, in particular inhibitors of HIV-1 or HIV-2 aspartate proteases, and are consequently suitable for treating retroviral diseases such as AIDS or its preliminary stages (e.g. ARDS). Compounds of the formula I also have an effect against corresponding animal retroviruses, such as SIV (in monkeys) or FIV (in cats).

In this context, compounds of the formula I surprisingly have particularly advantageous and important pharmacological properties, for example a very high antiviral activity, in the cell test, against different virus strains including those which are resistant to other protease inhibitors, for example in MT 2 cells, good pharmacokinetics, such as high bioavailability, high selectivity and, in particular, high blood levels (even in the case of oral administration).

The inhibitory effect of the compounds of the formula I on the proteolytic activity of HIV-1 protease can be demonstrated using known methods (cf. A. D. Richards et al., J. Biol. Chem. 265 (14), 7733–6 (1990)). In this case, inhibition of HIV-1 protease (preparation: cf. S. Billich et al., J. Biol. Chem. 263 (34), 17905–8 (1990)) activity is measured in the presence of the icosapeptide RRSNQVSQNYPIVQ-NIQGRR (SEQ ID NO: 1, an artificial substrate for HIV-1 protease, which substrate is prepared by peptide synthesis using known methods (cf. J. Schneider et al., Cell 54, 363–368 (1988)) and which, as a substrate analogue, contains one of the cleavage sites of the gag precursor protein (natural substrate for HIV-1 protease) This substrate and its cleavage products are analyzed by high performance liquid chromatography (HPLC).

The active compound to be tested is dissolved in dimethyl sulfoxide. The enzymic test is carried out by adding suitable dilutions of the inhibitor in 20 mM β-morpholinoethane-sulfonic acid (MES) buffer, pH 6.0, to the test mixture. The latter consists of the abovementioned icosapeptide (122 μM)

in 20 mM MES buffer, pH 6.0. 100 μl are employed per test sample. The reaction is started by adding 10 μl of HIV-1 protease solution and is terminated, after incubation at 37° C. for one hour, by adding 10 μl of 0.3M $HClO_4$. After the sample has been centrifuged at 10,000×g for 5 min, 20 μl of the resulting supernatant are loaded onto a 125×4.6 mm Nucleosil® C18-5m HPLC column ("reversed-phase" material from Macherey & Nagel, Düren, FRG, based on silica gel which is coated with $C_{18}$ alkyl chains). The uncleaved icosapeptide, and its cleavage products are eluted from the column using the following gradient: 100% eluent 1→50% eluent 1+50% eluent 2 (eluent 1: 10% acetonitrile, 90% $H_2O$, 0.1% trifluoroacetic acid (TFA); eluent 2: 75% acetonitrile, 25% $H_2O$, 0.08% k TFA) over 15 min, flowrate 1 ml/min. The eluted peptide fragments are quantified by measuring the peak height of the cleavage product at 215 nm.

Compounds of the formula I have inhibitory effects in the nanomolar range; they preferably have $IC_{50}$ values ($IC_{50}$= that concentration which lowers the activity of the HIV-1 protease by 50% as compared with a control without inhibitor) of from about $3\times10^{-7}$ to $5\times10^{-9}$ M, preferably of from $9\times10^{-8}$ to $9\times10^{-9}$ M.

An alternative method (cf. Matayoshi et al., Science 247, 954–8 (1990), modified here) for determining the inhibitory effect against HIV-1 protease can be described briefly as follows: the protease (purification, cf. Leuthardt et al., FEBS Lett. 326, 275–80 (1993)) is incubated, at room temperature in 100 μl of assay buffer (20 mM MES, pH 6.0; 200 mM NaCl; 1 mM dithiothreitol; 0.01% polyethylene glycol (average molecular weight from 6000 to 8000 Da), with 10 μM fluorogenic substrate SC4400 (4-(4-dimethylaminophenylazo)benzoyl-γ-amino-butyryl-Ser-Gln-Asn-Tyr-Pro-Ile-Val-Gln-EDANS SEQ ID NO:2, (EDANS=5-(2-aminoethylamino)-1-naphthalenesulfonic acid); Neosystem Laboratoire, France). The reaction is terminated by adding 900 μl of 0.03 M $HClO_4$. The activity of the HIV-1 protease is determined by measuring the increase in fluorescence at $\lambda ex=336$, $\lambda em=485$ nm. The $IC_{50}$ values of compounds of the formula I are determined as the concentration of the compound which is required to inhibit protease activity by 50% in the assay. The numerical values are determined from computer-generated graphs obtained from data derived from at least 5 concentrations of the relevant compound of the formula I and three-fold determinations at each concentration.

In a further test, it can be demonstrated that cells which are normally infected by HIV are protected from such an infection by compounds of the formula I, or that compounds of the formula I at least retard such an infection. MT 2 cells which are infected with HIV-1/MN are used for this test. MT 2 cells are transformed with HTLV-1 (a virus which causes leukemia) and are a continuous producer of this virus; for this reason, they are particularly susceptible to the cytopathic effect of HIV. MT 2 cells can be obtained from Dr. Douglas Richman through the AIDS Research and Reference Reagent Program, Division of AIDS, NIAID, NIH (cf. J. Biol. Chem. 263, 5870–5875 (1988) and also Science 229, 563–6 (1985)). The MT 2 cells are maintained in culture in RPMI 1640 Medium (Gibco, Scotland; RPMI comprises an amino acid mixture without glutamine) which is supplemented with 10% heat-inactivated fetal calf serum. glutamine and standard antibiotics. The cells, and also the virus stock solution (HIV-1/MN) which is used for the infection, are in every case free of mycoplasmas. The virus stock solution is prepared as a cell culture supernatant of the permanently infected cell line H9/HIV-1/MN, which cell line can also be obtained, from Dr. Robert Gallo, through the AIDS Research and Reference Program, Division of AIDS, NIAID, NIH (cf. also Science 224, 500–3 (1984) and Science 226, 1165–70 (1984)). The titer of the HIV-1/MN virus stock solution (determined by titrating on MT 2 cells) is $4.2\times10^5$ TCID50/ml (TCID50=tissue culture infective dose=dose, which infects 50% of the MT 2 cells). In order to measure the infection-inhibiting effect of the compounds of the formula I, 50 μl of the relevant test substance in culture medium, and 2800 TCID50 of HIV-1/MN in 100 μl of culture medium, are added to $2\times10^4$ exponentially growing MT 2 cells, which are initially introduced in 50 μl of culture medium on 96-well microtiter plates (with round bottom). After 4 days of incubation (at 37° C. and under 5% $CO_2$), a sample of in each case 10 μl of the supernatant is removed from each well and transferred to another 96-well microtiter plate, which, if required, is stored at −20° C. In order to measure the activity of the virus-associated reverse transcriptase, 30 pi of reverse transcriptase cocktail are added to each sample. The reverse transcriptase cocktail consists of 50 mM Tris (α,α,α-tris(hydroxymethyl)-methylamine, Ultra pur, Merck, Germany) pH 7.8; 75 mM KCl, 2 mM dithiothreitol, 5 mM $MgCl_2$; 0.1% Nonidet P-40 (detergent; Sigma, Switzerland), 0.8 mM EDTA, 10 μg/ml poly-A (Pharmacia, Uppsala, Sweden) and 0.16 μg/ml of oligo(T) (=pdT(12–18), Pharmacia, Uppsala, Sweden) as the template primer—if desired, the mixture is filtered through a 0.45 mm Acrodisc filter (Gelman Sciences Inc., Ann Arbor, USA). It is stored at −20° C. Prior to the test, 0.1% (v/v) [alpha-$^{32}$P]dTTP is added to aliquots of the solution in order to bring the radioactivity to 10 μCi/ml.

After mixing, the plate is incubated at 37° C. for 2 h. 5 μl of the reaction mixture are transferred to DE81 paper (Whatman, one filter per well). The dried filters are washed three times for 5 min with 300 mM NaCl/25 mM trisodium citrate and then once with ethanol, and air-dried once again. The radioactivity on the filters is measured in a Packard Matrix 96-well counter (Packard, Zurich, Switzerland). The ED90 values are calculated and are defined as the concentration of the test compound which reduces the RT activity by 90% as compared with a control without test compound.

In this test, the preferred compounds of the formula I have an ED90, i.e. a 90% inhibition of virus replication, at concentrations of from $3\times10^{-7}$ to $10^{-9}$ M, in particular of from $3\times10^{-8}$ to $10^{-9}$ M.

The compounds of the formula I are therefore suitable for retarding the replication of HIV-1 in cell cultures in a highly efficient manner.

In order to determine the pharmacokinetics of compounds of the formula I, the latter are dissolved in dimethyl sulfoxide (DMSO) at a concentration of 240 mg/ml. These solutions are diluted 1:20 (v/v) with 20% (w/v) aqueous hydroxypropyl-β-cyclodextrin solution in order to bring the concentration of the relevant test substance to 12 mg/ml. The resulting solution is ultrasonicated briefly and administered orally to female BALB/c mice (Bomholtgarden, Copenhagen, Denmark) by artificial gavage feeding at a dose of 120 mg/kg. At predetermined times (e.g. 30, 60, 90, 120 min) after the administration, mice are sacrificed and the blood is collected in heparinized tubes. The blood is centrifuged (12,000×g, 5 min) and the plasma is taken off. The plasma is deproteinized by adding an equal volume of acetonitrile. The mixture is vortexed and left to stand at room temperature for from 20 to 30 min. The precipitate is pelleted by centrifugation (12,000×g, 5 min) and the concentration of the test compound is ascertained by reversed-phase high performance liquid chromatography (HPLC).

The HPLC analysis of the samples which have been obtained by the above-described method is carried out on a 125×4.6 mm Nucleosil® $C_{18}$ column (reversed-phase material from Macherey & Nagel, Duren, Germany, based on silica gel which is derivatized with carbon radicals having 18 carbon atoms) which possesses a 2 cm-long precolumn of the same column material. The sample is eluted with the following linear acetonitrile/water gradient (in each case in the presence of 0.05% trifluoroacetic acid): 20% acetonitrile to 100% acetonitrile over 20 min; then 100% acetonitrile for 5 min; then return to the initial conditions for 1 min, and 4 min of reequilibration. The flowrate is 1 ml/min. Under these conditions, the compound of the formula I from Example 1, for example, has a retention time of approx. 15.5 min and its detection limit is 0.1–0.2 $\mu$M. The test compound is detected by measuring UV absorption at 255 nm. Peaks are identified by the retention time and the UV spectrum between 205 and 400 nm. The concentrations are determined by the external standard method, the peak heights are ascertained in order to determine concentrations by comparison with standard curves. The standard curves are prepared by an analogous HPLC analysis of mouse plasma which contains known concentrations of the relevant test compound and which has been worked up in accordance with the above-described method.

In this analysis, plasma concentrations are obtained for compounds of the formula I which are well above the $ED_{90}$ values which were determined in the above-described cell experiment, i.e. up to about 1200 times greater than the $ED_{90}$ values after 30 min and up to about 800 times greater than the $ED_{90}$ values after 90 min, with plasma concentrations preferably being from 0.1 $\mu$M to 15 $\mu$M, in particular from 1 to 15 $\mu$M, at 30 min after oral administration, and being from 0.5 to 8 $\mu$M, in particular from 1 to 8 $\mu$M, at 90 min after oral administration.

It is particularly the combination of high bioavailability (in particular high plasma levels), which is in itself surprising, and an unexpectedly outstanding $ED_{90}$ value in the cell experiment which makes the compounds of the present invention valuable in a manner which was not foreseen. The combined presence of the $NR_6R_7$ radical and of branched, in particular tertiary lower alkyl radicals $R_3$ and $R_4$ evidently contributes to these properties.

The combination of the positive properties is particularly pronounced in compounds of the formula I in which $R_6$ and $R_7$ are in each case lower alkyl, in particular ethyl, and at least one, preferably both, of the radicals $R_3$ and $R_4$ is/are tert-lower alkyl, in particular tert-butyl When antienzymic activity against a large number of human aspartate proteases is determined using known methods (cf., for example Biochem. J. 265, 871–8 (1990)), it is found that compounds of the formula I have a high selectivity in favor of the HIV, in particular HIV-1, retrovirat aspartate protease. Thus, when tested against cathepsin D, compounds of the formula I have inhibitory constants ($IC_{50}$s) which are greater than 25 $\mu$M. in these experiments, the $IC_{50}$ against human cathepsin D is measured at pH 3.1. The test is carried out in accordance with known methods using the substrate KPIQF*NphRL (cf. Jupp, R. A., Dunn, B. M., Jacobs, J. W., Vlasuk, G., Arcuri, K. E., Veber, D. F., S. Perow, D. S., Payne, L. S., Boger, J., DeLazio, S., Chakrabarty, P. K., TenBroeke, J., Hangauer, D. G., Ondeyka, D., Greenlee, W. J. and Kay, J.: The selectivity of statine-based inhibitors against various human aspartic proteases. Biochem. J. 265: 871–878 (1990)).

The compounds of the formula I may be administered alone or in combination (as a fixed combination of appropriate preparations or as a combination of individual active compounds or individual preparations in chronologically staggered sequence) with other compounds (or salts thereof, provided at least one salt-forming group is present) which are active against retroviruses, in particular HIV, such as HIV-1 or HIV-2; in particular with inhibitors of reverse transcriptase, especially nucleoside analogues, in particular 3'-azido-3'-deoxypyrimidine (=Zidovudine=®RETROVIR, Burroughs-Wellcome), 2',3'-dideoxy-cytidine (=Zalcitabine=®HIVID, Hoffmann-LaRoche), 2',3'-dideoxyInosine (=Didanosine=7VIDEX, Bristol-Myers-Squibb) or (2R,cis)-4-amino-1-(2-hydroxymethyl-1,3-oxathiolan-5-yl)-(1H)-pyrimidin-2-one (=Lamivudine, Glaxo) or non-nucleoside analogues, such as 11-cyclopropyl-5,11-dihydro-4-methyl-(6H)-dipyrido[3,2-b;2',3'-e]-[1,4]diazepin-6-one; or with one or more (in particular one or else two) other inhibitors of retroviral aspartate proteases, in particular of HIV, such as HIV-1 and HIV-2, aspartate proteases, in particular a) one of the inhibitors mentioned in EP 0 346 847 (published on Dec. 20, 1989) and EP 0 432 695 (published on Jun. 19, 1991; corresponds to U.S. Pat. No. 5,196,438, published on Mar. 23, 1993), in particular the compound having the designation Ro 31-8959 (=Saquinavir; Hoffmann-LaRoche);

b) one of the inhibitors mentioned in EP 0 541 168 (published on May 12, 1993; corresponds to U.S. Pat. No. 5,413,999), in particular the compound having the designation L-735 524 (=Indinavir=®CRIXIVAN; Merck & Co., Inc.);

c) one of the inhibitors mentioned in EP 0 486 948 (published on May 27, 1992; corresponds to U.S. Pat. No. 5,354,866), in particular the compound having the designation ABT-538 (=Ritonavir; Abbott));

d) the compound having the designation KVX-478 (or VX-478 or 141 W94; GlaxoWellcome, Vertex and Kissei Pharmaceuticals)

e) the compound having the designation AG-1343 (Agouron);

f) the compound having the designation KNI-272 (Nippon Mining);

g) the compound having the designation U-96988 (Upjohn); and/or h) the compound having the designation BILA-2011 BS (=Palinavir; Boehringer-lngelheim), or in each case a salt thereof, provided salt-forming groups are present.

The compounds of the formula I may also be used for the prevention, control and therapy of infections by retroviruses, in particular HIV, such as HIV-2 or, in particular HIV-1, in cell cultures, in particular cell cultures of lymphocyte cell lines, which are derived from homeothermic animals, something which is particularly advantageous in the case of very valuable cell cultures which, for example, produce specific antibodies, vaccines or messenger substances, such as interleukins and the like, and are therefore of great commercial value.

Finally, the compounds of the formula I may be used as standards in experiments, for example as HPLC standards or as standards for comparing animal models in relation to different aspartate protease inhibitors, for example with regard to the blood levels which can be reached.

In the case of the groups of preferred compounds of the formula I which are specified below, definitions of substituents from the abovementioned general definitions can be employed in a meaningful manner, for example for the purpose of replacing more general definitions with more specific definitions or, in particular, with definitions which are characterized as being preferred; in each case, preference is given to the definitions which are characterized above as being preferred or as being typical.

Preference is given to a compound of the formula I, in particular Ia, in which $R_1$ and $R_2$ are in each case, independently of each other, lower alkyl, in particular methyl;

$R_3$ and $R_4$ are, independently of each other, sec- or tert-lower alkyl; in particular isopropyl, sec-butyl or tert-butyl, with preferably at least one of the two radicals being tert-lower alkyl, in particular the two radicals being tert-lower alkyl, in particular tert-butyl;

$R_5$ is phenyl; and $R_6$ and $R_7$ are, independently of each other, lower alkyl, in particular ethyl, or, together with the linking nitrogen atom, are pyrrolidino;

or a salt thereof, provided at least one salt-forming group is present.

Particular preference is given to a compound of the formula I, in particular of the formula Ia, in which $R_1$ and $R_2$ are in each case methyl;

$R_3$ is isopropyl or tert-butyl;

$R_4$ is tert-butyl;

$R_6$ is phenyl; and $R_7$ are in each case lower alkyl, in particular ethyl or methyl, especially ethyl, or a salt thereof, provided a salt-forming group is present (in particular a salt with a strong acid, as defined above).

The greatest preference is given to 1-[p-(N,N-diethylamino)phenyl-4(S)-hydroxy-2-[N-(N-methoxycarbony-(L)-tert-leucyl)amino]- 5(S)-[N-(N-methoxycarbonyl-(L)-valyl)-amino]-6-phenyl-2-azahexane, or to a pharmaceutically utilizable salt thereof (in particular a salt with a strong acid, as defined above).

The very greatest preference is given to 1-[p-(N,N-diethylamino)phenyl]-4(S)-hydroxy-5(S)-2,5-bis!N-(N-methoxycarbonyl-(L)-tert-leucyl)amino]-6-phenyl-2-azahexane, or a pharmaceutically utilizable salt thereof (in particular a salt with a strong acid, as defined above).

Great preference is also given to the remaining compounds of the formula I which are mentioned in the examples or to pharmaceutically utilizable salts thereof, provided at least one salt-forming group is present.

The compounds of the formula I, or salts of those compounds having at least one salt-forming group, are prepared by processes which are known per se, for example by a) adding a hydrazine derivative of the formula

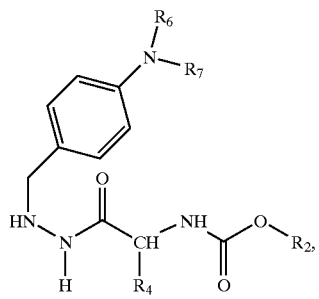

in which the radicals $R_2$, $R_4$, $R_6$ and $R_7$ have the meanings given for compounds of the formula I, to an epoxide of the formula

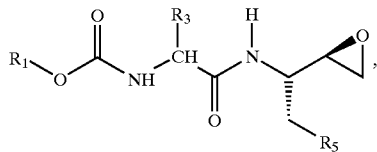

in which the radicals $R_1$, $R_3$ and $R_5$ have the meanings given for compounds of the formula I, with free functional groups, with the exception of those which are involved in the reaction, being present in protected form if necessary, and detaching protecting groups which are present, or b) condensing an amino compound of the formula

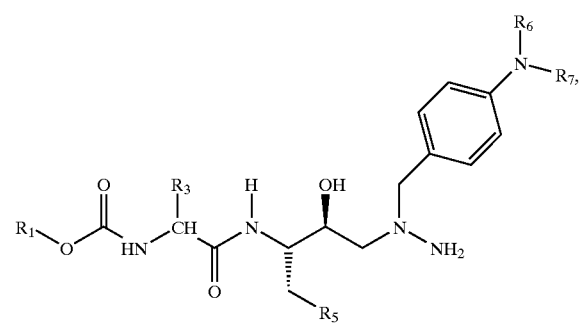

in which the radicals $R_1$, $R_3$, $R_5$, $R_6$ and $R_7$ have the meanings given for compounds of the formula I, with an acid of the formula

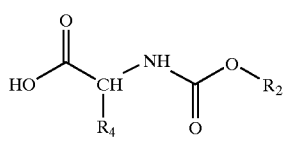

or a reactive acid derivative thereof, in which the radicals $R_2$ and $R_4$ have the meanings given for compounds of the formula I, with free functional groups, with the exception of those which are involved in the reaction, being present in protected form if necessary, and detaching protecting groups which are present, or c) condensing an amino compound of the formula

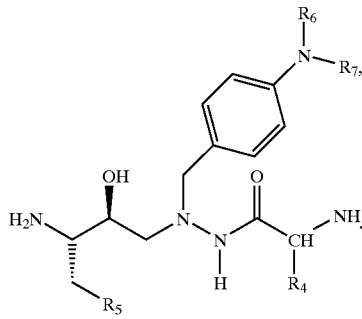

in which the radicals $R_2$, $R_4$, $R_5$, $R_6$ and $R_7$ have the meanings given for compounds of the formula I, with an acid of the formula

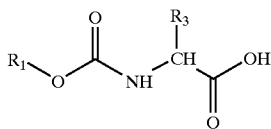

(VIII)

or a reactive acid derivative thereof, in which $R_1$ and $R_3$ have the meanings given for compounds of the formula I, with free functional groups, with the exception of those which are involved in the reaction, being present in protected form if necessary, and detaching any protecting groups which are present, or d) for preparing compounds of the formula I in which the substituent pairs $R_1$ and $R_2$, and also $R_3$ and $R_4$, are in each case two identical radicals, as defined for compounds of the formula I, and $R_5$, $R_6$ and $R_7$ have the meanings given for compounds of the formula I, condensing a diamino compound of the formula

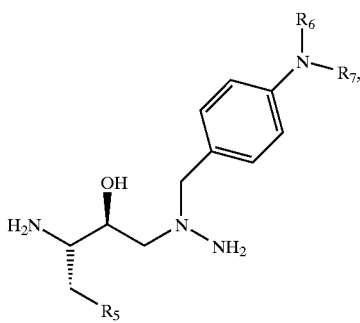

(IX)

in which the radicals have the meanings which have just been mentioned, with an acid of the formula

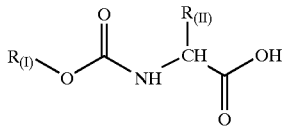

(VIIIa)

or a reactive acid derivative thereof, in which $R_{(I)}$ and $R_{(II)}$, respectively, have the meanings given in formula I for $R_1$ and $R_2$ and $R_3$ and $R_4$, respectively, with the pairs $R_1$ and $R_2$ and also $R_3$ and $R_4$ in each case being two identical radicals, with free functional groups, with the exception of those which are involved in the reaction, being present in protected form if necessary, and detaching any protecting groups which are present, or e) reacting an imino compound of the formula I',

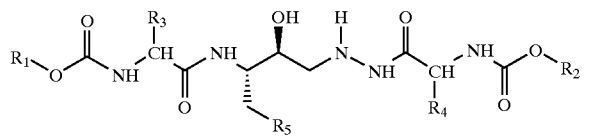

(I')

in which the radicals $R_1$, $R_2$, $R_3$, $R_4$ and $R_5$ have the meanings given for compounds of the a, formula I, with a compound of the formula X,

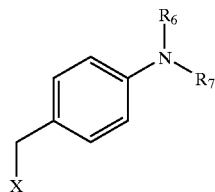

(X)

in which X is a leaving group and $R_6$ and $R_7$ have the meanings given for compounds of the formula I, with free functional groups, with the exception of those which are involved in the reaction. being present in protected form if necessary, and detaching any protecting groups which are present, or f) reacting an imino compound of the formula I',

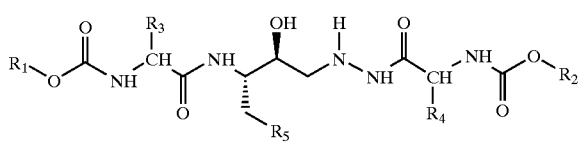

(I')

in which the radicals $R_1$, $R_2$, $R_3$, $R_4$ and $R_5$ have the meanings given for compounds of the formula I, with an aldehyde of the formula X*,

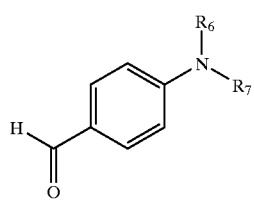

(X*)

in which $R_5$ and $R_7$ have the meanings given for compounds of the formula I, or a reactive derivative thereof with reductive alkylation, with free functional groups, with exception of those which are involved in the reaction, being present in protected form if necessary, and detaching any protecting groups which are present, and, if desired, converting a compound of the formula I which can be obtained by one of the above processes a) to f) and which possesses at least one salt-forming group into its salt, or converting an obtainable salt into the free compound or into another salt, and/or resolving isomeric mixtures which may be obtainable, and/or converting a compound of the formula I according to the invention into another compound of the formula I according to the invention.

The above processes are described in more detail below with reference to preferred embodiments:

In the subsequent description of the individual processes, and of the preparation of the starting materials, the radicals $R_1$, $R_2$, $R_3$, $R_4$, $R_5$, $R_5$ and $R_7$ have, unless otherwise indicated, the meanings given for the compounds of the formula I, preferably the meanings which are in each case given as being preferred.

Process a) (Addition of an Amine to an Epoxide):

The amino group of the hydrazine derivatives of the formula III which participates in the reaction preferably has a free hydrogen atom; however, it can also itself be derivatized in order to increase the reactivity of the hydrazine derivative.

The epoxide of the formula IV enables the terminal addition of the hydrazine derivative to proceed in a preferential manner.

In a general manner (not only in relation to process a)), functional groups in starting materials, reaction of which functional groups is to be avoided, in particular carboxyl, amino including sec-amino (=—NH—) and hydroxyl groups (in process a)), especially sec-amino groups, can be protected by suitable protecting groups (conventional protecting groups) which are customarily used not only in the synthesis of peptide compounds but also of cephalosporins and penicillins and also nucleic acid derivatives and sugars. These protecting groups can already be present in the precursors and are intended to protect the functional groups concerned from undesirable side reactions such as acylations, etherifications, esterifications, oxidations, solvolysis and the like. In particular cases, the protecting groups can, over and above this, cause reactions to proceed in a selective manner, for example in a stereoselective manner. It is characteristic of protecting groups that they can be detached readily, i.e. without any undesirable side reactions, for example solvolytically, reductively, photolytically or else enzymically, for example under physiological conditions as well. However, radicals which are analogous to protecting groups can also be present in the final products. Compounds of the formula I having protected functional groups can possess a higher degree of metabolic stability, or possess pharmacodynamic properties which are in some other way superior, as compared with the corresponding compounds having free functional groups. In that which has been mentioned above, and in that which follows, protecting groups in the true sense are being referred to when the radicals concerned are no longer present in the final products.

The protection of functional groups by these protecting groups, the protecting groups themselves, and their detachment reactions, are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; volume 3 (E. Gross and J. Meienhofer, Eds.), Academic Press, London and New York 1981, in "Methoden der organischen Chemie (Methods of organic chemistry)", Houben-Weyl, 4th edition, volume 15/1, Georg Thieme Verlag, Stuttgart 1974, in H.-D. Jakubke and H. Jescheit, "Aminosäuren, Peptide, Proteine (Amino acids, peptides and proteins)", Verlag Chemie, Weinheim, Deerfield Beach and Basel 1982, and in Jochen Lehmann, "Chemie der Kohlenhydrate: Monosaccharide und Derivate (Chemistry of carbohydrates: monosaccharides and derivatives)", Georg Thieme Verlag, Stuttgart 1974.

A carboxyl group is protected, for example, as an ester group which can be selectively detached under mild conditions. A carboxyl group which is protected in esterified form is first and foremost esterified with a lower alkyl group which is preferably branched in the 1 position of the lower alky group or preferably substituted by suitable substituents in the 1 or 2 positions of the lower alkyl group.

A protected carboxyl group which is esterified with a lower alkyl group is, for example, methoxycarbonyl or ethoxycarbonyl.

A protected carboxyl group which is esterified with a lower alkyl group which is branched in the 1 position of the lower alkyl group is. for example, tert-lower alkoxycarbonyl, e.g. tert-butoxycarbonyl.

A protected carboxyl group which is esterified with a lower alkyl group which is substituted by suitable substituents in the 1 or 2 positions of the lower alkyl group is, for example, arylmethoxycarbonyl having one or two aryl radicals, in which aryl is unsubstituted phenyl or phenyl which is mono-, di- or tri-substituted, for example by lower alkyl, e.g. tert-lower alkyl, such as tert-butyl, lower alkoxy, e.g. methoxy, hydroxyl, halogen, e.g. chlorine, and/or nitro, for example benzyloxycarbonyl, benzyloxycarbonyl which is substituted by the said substituents, e.g. 4-nitrobenzyloxycarbonyl or 4-methoxybenzyloxycarbonyl, diphenylmethoxycarbonyl or diphenylmethoxycarbonyl which is substituted by the said substituents, e.g. di(4-methoxyphenyl)methoxycarbonyl, and also carboxyl which is esterified with a lower alkyl group, with the lower alkyl group being substituted by suitable substituents in the 1 or 2 positions, such as 1-lower alkoxy-lower alkoxycarbonyl, e.g. methoxymethoxycarbonyl, 1-methoxyethoxycarbonyl or 1-ethoxyethoxycarbonyl, 1-lower alkylthio-lower alkoxycarbonyl, e.g. 1-methylthiomethoxycarbonyl or 1-ethylthioethoxy-carbonyl, aroylmethoxycarbonyl, in which the aroyl group is benzoyl which is unsubstituted or substituted, for example, by halogen, such as bromine, e.g. phenacyloxycarbonyl, 2-halogeno-lower alkoxycarbonyl, e.g. 2,2,2-trichloroethoxycarbonyl, 2-bromoethoxycarbonyl or 2-iodoethoxycarbonyl, and also 2-(trisubstituted silyl)-lower alkoxycarbonyl, in which the substituents are in each case, independently of each other, an aliphatic, araliphatic, cycloaliphatic or aromatic hydrocarbon radical which is unsubstituted or substituted, for example, by lower alkyl, lower alkoxy, aryl, halogen and/or nitro, for example lower alkyl, phenyl-lower alkyl, cycloalkyl or phenyl, which is unsubstituted or substituted as described above, e.g. 2-tri-lower alkylsilyl-lower alkoxycarbonyl, such as 2-tri-lower alkylsilylethoxycarbonyl, e.g. 2-trimethylsilylethoxycarbonyl or 2-(di-n-butylmethylsilyl) ethoxycarbonyl, or 2-triarylsilylethoxycarbonyl, such as triphenylsilylethoxycarbonyl.

A carboxyl group can also be protected as an organic silyloxycarbonyl group. An organic silyloxycarbonyl group is, for example, a tri-lower alkylsilyloxycarbonyl group, e.g. trimethylsilyloxycarbonyl.

A protected carboxyl group is preferably tert-lower alkoxycarbonyl, e.g. tert-butoxycarbonyl, benzyloxycarbonyl, 4-nitrobenzyloxycarbonyl, 9-fluorenylmethoxycarbonyl or diphenylmethoxycarbonyl.

A protected amino group can be protected with an amino protecting group, e.g. in the form of an acylamino, arylmethylamino, etherified mercaptoamino, 2-acyl-lower alk-1-enylamino or silylamino group, or be present as an azido group.

In a corresponding acylamino group, acyl is, for example, the acyl radical of an organic carboxylic acid having, for example, not more than 18 carbon atoms, in particular of a lower alkanecarboxylic acid which is unsubstituted or substituted, for example by halogen or aryl, or of benzoic acid which is unsubstituted or substituted, for example by halogen, lower alkoxy or nitro, or preferably of a carbonic acid semiester. Examples of such acyl groups are lower alkanoyl, such as formyl, acetyl, propionyl or pivaloyl, halogeno-lower alkanoyl, e.g. 2-halogenoacetyl, such as 2-chioro-, 2-bromo-, 2-iodo-, 2,2,2-trifluoro- or 2,2,2-trichloroacetyl, benzoyl which is unsubstituted or substituted, for example by halogen, lower alkoxy or nitro, such as benzoyl, 4-chlorobenzoyl, 4-methoxybenzoyl or 4-nitrobenzoyl, lower alkoxycarbonyl, lower alkoxycarbonyl which is preferably branched in the 1 position of the lower alkyl radical or preferably suitably substituted in the 1 or 2 positions, e.g. tert-lower alkoxycarbonyl, such as tert-butoxycarbonyl, arylmethoxycarbonyl having one, two or three aryl radicals which are phenyl which is unsubstituted or mono- or poly-substituted, for example by lower alkyl, in particular tert-lower alkyl, such as tert-butyl, lower alkoxy, such as methoxy, hydroxyl, halogen, such as chlorine, and/or nitro, e.g. benzyloxycarbonyl, 4-nitrobenzyloxycarbonyl, diphenylmethoxycarbonyl, 9-fluorenylmethoxycarbonyl or di-(4-methoxyphenyl) methoxycarbonyl, aroylmethoxycarbonyl, in which the aroyl group is preferably benzoyl which is unsubstituted or substituted, for example by halogen, such as bromine, e.g. phenacyloxycarbonyl, 2-halogeno-lower alkoxycarbonyl, e.g. 2,2,2-trichloroethoxycarbonyl, 2-bromoethoxycarbonyl or 2-iodoethoxycarbonyl, 2-(trisubstituted silyl)-lower alkoxycarbonyl, e.g. 2-tri-lower alkylsilyl-lower alkoxycarbonyl, such as 2-trimethylsilylethoxycarbonyl or 2-(di-n-butylmethylsilyl)ethoxycarbonyl, or triarylsilyl-lower alkoxycarbonyl, e.g. 2-triphenylsilylethoxycarbonyl.

In an arylmethylamino group which is, for example, a mono-, di- or, in particular, triarylmethylamino group, the aryl radicals are, in particular, substituted or unsubstituted phenyl radicals. Examples of such groups are benzyl-, diphenylmethyl- or, in particular, trityl-amino, or, very particularly, 1-aryl-lower alkylmethylamino, in which the lower alkyl radical is preferably branched in the 1 position, as in 1-methyl-1-phenylethylamino.

In an etherified mercaptoamino group, the mercapto group is first and foremost present as a substituted arylthio or aryl-lower alkylthio, in which aryl is, for example, phenyl which is unsubstituted or substituted, for example by lower alkyl, such as methyl or tert-butyl, lower alkoxy, such as methoxy, halogen, such as chlorine, and/or nitro, e.g. 4-nitrophenylthio.

In a 2-acyl-lower alk-1-enyl radical which can be used as an amino protecting group, acyl is, for example, the corresponding radical of a lower alkanecarboxylic acid, of a benzoic acid which is unsubstituted or substituted, for example by lower alkyl, such as methyl or tert-butyl, lower alkoxy, such as methoxy, halogen, such as chlorine, and/ or nitro, or, in particular, of a carbonic acid semiester, such as a carbonic acid lower alkyl semiester. Corresponding protecting groups are, first and foremost, 1-lower alkanoyl-lower alk-1-en-2-yl, e.g. 1-lower alkanoylprop-1-en-2-yl, such as 1-acetylprop-1-en-2-yl, or lower alkoxycarbonyl-lower alk-1-en-2-yl, e.g. lower alkoxycarbonylprop-1-en-2-yl, such as 1-ethoxycarbonylprop-1-en-2-yl.

A silylamino group is, for example, a tri-lower alkylsilylamino group, e.g. trimethylsilylamino or tert-butyldimethylsilylamino. The silicon atom of the silylamino group can also be substituted by just two lower alkyl groups, e.g. methyl groups, and the amino group or carboxyl group of a second molecule of the formula I. Compounds having such protecting groups can be prepared, for example, using the corresponding chlorosilanes, such as dimethylchlorosilane, as silytating agents.

An amino group can also be protected by converting it into the protonated form; corresponding anions which are suitable are first and foremost those of strong inorganic acids, such as of sulfuric acid, phosphoric acid or hydrohalic acids, e.g. the chlorine anion or bromine anion, or of organic sulfonic acids, such as p-toluenesulfonic acid.

Preferred amino protecting groups are lower alkoxycarbonyl, phenyl-lower alkoxycarbonyl, fluorenyl-lower alkoxycarbonyl, 2-lower alkanoyl-lower alk-1-en-2-yl, 1-methyl-1-phenyl-ethyl or lower alkoxycarbonyl-lower alk-1-en-2-yl.

A hydroxyl group can be protected, for example, with an acyl group, e.g. with halogen, such as chlorine, substituted lower alkanoyl, such as 2,2-dichloroacetyl, or, in particular, with an acyl radical of a carbonic acid semiester which is specified for protected amino groups. A preferred hydroxyl protecting group is, for example, 2,2,2-trichloroethoxycarbonyl, 4-nitrobenzyloxycarbonyl, diphenylmethoxycarbonyl or trityl. A hydroxyl group can furthermore be protected with tri-lower alkylsilyl, e.g. trimethylsilyl, triisopropylsilyl or tert-butyidimethylsilyl, a readily detachable etherifying group, e.g. an alkyl group, such as tert-lower alkyl, e.g. tert-butyl, an oxa- or a thia-aliphatic or -cycloaliphatic, in particular 2-oxa- or 2-thia-aliphatic or -cycloaliphatic, hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having 5–7 ring atoms, such as 2-tetrahydrofuryl or 2-tetrahydropyranyl, or a corresponding thia analogue, and also with 1-phenyl-lower alkyl, such as benzyl, diphenylmethyl or trityl, where the phenyl radicals can be unsubstituted or substituted, for example by halogen, e.g. chlorine, lower alkoxy, e.g. methoxy, and/or nitro.

Hydroxyl and amino groups which occur adjacently in a molecule can be protected, for example, with bivalent protecting groups, such as a methylene group which is preferably substituted, for example by one or two lower alkyl radicals or oxo, e.g. with unsubstituted or substituted alkylidene, e.g. lower alkylidene, such as isopropylidene, cycloalkylidene, such as cyclohexylidene, a carbonyl group or benzylidine.

Within the meaning of the present disclosure, a protecting group, for example a carboxyl protecting group, is expressly also to be understood as meaning a polymeric support, as is suitable, for example, for the Merrifield synthesis, which is bonded in a readily detachable manner to the functional group, for example carboxyl group, which is to be protected. An example of such a suitable polymeric support is a polystyrene resin which is weakly crosslinked by copolymerization with divinylbenzene and which carries suitable bridging members for the reversible bonding.

The compounds of the formula III are preferably added to the epoxides of the formula IV under the reaction conditions which are customary for adding nucleophiles to epoxides.

The addition is effected, in particular, in aqueous solution and/or in the presence of polar solvents, such as alcohols, e.g. methanol, ethanol, isopropanol or ethylene glycol, ethers, such as dioxane, amides, such as dimethylformamide, or phenols, such as phenol, and also under anhydrous conditions, in apolar solvents, such as benzene or toluene, or in benzene/water emulsions, if desired in the presence of acidic or basic catalysts, e.g. of alkaline solutions, such as sodium hydroxide solution, or in the presence of solid phase catalysts, such as aluminum oxide, which are doped with the hydrazine, in ethers, e.g. diethylether, generally at temperatures of from about 0° C. up to the boiling temperature of the corresponding reaction mixture, preferably between 20° C. and reflux temperature, if desired under elevated pressure, e.g. in a bomb tube, with it also being possible to exceed the boiling temperature, and/or under an inert gas, such as nitrogen or argon, with it being possible for each one of the two compounds of the formulae III and IV to be present in excess, for example in a molar ratio of from 1:1 to 1:100, preferably in a molar ratio of from 1:1 to 1:10, particularly preferably in a ratio of from 1:1 to 1:3.

If necessary, protected groups are set free in accordance with the methods which are described below under "protecting group detachment".

Process b) (Preparation of an Amide Bond)

With the exception of the groups which are to participate in the reaction or which do not react under the reaction conditions, functional groups in starting materials of the formulae V and VI are protected, independently of each other, with one of the protecting groups mentioned under process a).

The compounds of the formula VI either contain a free carboxyl group or are present as reactive acid derivatives thereof, e.g. as the derived activated esters or reactive anhydrides, and also reactive cyclic amides. The reactive acid derivatives can also be formed in situ.

Activated esters of compounds of the formula VI having a terminal carboxyl croup are, in particular, esters which are unsaturated at the linking carbon atom of the radical to be esterified, e.g. of the vinyl ester type, such as vinyl esters (obtainable, for example, by transesterifying a corresponding ester with vinyl acetate; activated vinyl ester method), carbamoyl esters (obtainable, for example, by treating the corresponding acid with an isoxazolium reagent; 1,2-oxazolium method or Woodward method), or 1-lower alkoxyvinyl esters (obtainable, for example, by treating the corresponding acid with a lower alkoxyacetylene; ethoxyacetylene method), or esters of the amidino type, such as N,N'-di-substituted amidino esters (obtainable, for example, by treating the corresponding acid with a suitable N,N'-disubstituted carbodiimide, e.g. N,N'-dicyclohexylcarbodiimide or, in particular, N-(3-dimethylaminopropyl)-N'-ethylcarbodiimide; carbodiimide method), or N,N-disubstituted amidino esters (obtainable, for example, by treating the corresponding acid with an N,N-disubstituted cyanamide; cyanamide method), suitable aryl esters, in particular phenyl esters which are suitably substituted by electron-attracting substituents (obtainable, for example, by treating the corresponding acid with a suitably substituted phenol, e.g. 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexyl-carbodiimide; activated aryl ester method), cyanomethyl esters (obtainable, for example, by treating the corresponding acid with chioroacetonitrile in the presence of a base; cyanomethyl ester method), thio esters, in particular phenylthio esters which are unsubstituted or substituted, e.g. by nitro (obtainable, for example, by treating the corresponding acid with thiophenols which are unsubstituted or substituted, e.g. by nitro, inter alia using the anhydride method or carbodiimide method; activated thiol ester method), or, in particular, amino esters or amido esters (obtainable, for example, by treating the corresponding acid with an N-hydroxyamino compound or N-hydroxyamido compound, respectively, e.g. N-hydroxysuccinimide, N-hydroxypiperidine, N-hydroxyphthalimide, N-hydroxy-5-norbornene-2,3-dicarboximide, 1-hydroxybenzotriazole or 3-hydroxy-3,4-dihydro-1,2,3-benzotriazin-4-one, e.g. in accordance with the anhydride method or carbodiimide method; activated N-hydroxy ester method). Internal esters, e.g. γ-lactones, may also be employed.

Anhydrides of acids can be symmetrical, or preferably mixed, anhydrides of these acids, e.g. anhydrides with inorganic acids, such as acid halides, in particular acid chlorides (obtainable, for example, by treating the corresponding acid with thionyl chloride, phosphorus pentachloride, phosgene or oxalyl chloride; acid chloride method), azides (obtainable, for example, from a corresponding acid ester by way of the corresponding hydrazide and its treatment with nitrous acid; azide method), anhydrides with carbonic acid semiesters, e.g. carbonic acid lower alkyl semiesters (in particular methyl chloroformate) (obtainable, for example, by treating the corresponding acid with lower alkyl chloroformates or with a 1-lower alkoxycarbonyl-2-lower alkoxy-1,2-dihydroquinoline; mixed O-alkylcarbonic acid anhydride method), or anhydrides with dihalogenated, in particular dichlorinated, phosphoric acid (obtainable, for example, by treating the corresponding acid with phosphorus oxychloride; phosphorus oxychloride method), anhydrides with other phosphoric acid derivatives (e.g. those which can be obtained using phenyl-N-phenyl-phosphoramidochloridate or by reacting alkylphosphoric acid amides in the presence of sulfonic acid anhydrides and/or racemization-lowering additives, such as N-hydroxybenzotriazole, or in the presence of diethyl cyanophosphonate) or with phosphorous acid derivatives, or anhydrides with organic acids, such as mixed anhydrides with organic carboxylic acids (obtainable, for example, by treating the corresponding acid with a substituted or unsubstituted lower alkanecarbonyl halide or phenyl-lower alkanecarbonyl halide, e.g. phenylacetyl chloride, pivaloyl chloride or trifluoroacetyl chloride; mixed carboxylic anhydride method) or with organic sulfonic acids (obtainable, for example, by treating a salt, such as an alkali metal salt, of the corresponding acid with a suitable organic sulfonyl halide, such as lower alkane- or aryl-, e.g. methane- or p-toluene-sulfonyl chloride; mixed sulfonic anhydride method) and also symmetrical anhydrides (obtainable, for example, by condensing the corresponding acid in the presence of a carbodiimide or of 1-diethylamino-propine; symmetrical anhydride method).

Suitable cyclic amides are, in particular, amides with five-membered diazacycles of aromatic character, such as amides with imidazoles, e.g. imidazole (obtainable, for example, by treating the corresponding acid with N,N'-carbonyldiimidazole; imidazole method), or pyrazole, e.g. 3,5-dimethylpyrazole (obtainable, for example, by way of the acid hydrazide by treating with acetylacetone; pyrazolide method).

As mentioned, derivatives of carboxylic acids which are used as acylating agents can also be formed in situ. Thus. N,N'-disubstituted amidino esters, for example, can be formed in situ by reacting the mixture of the starting material of the formula IV and the acid used as acylating agent in the presence of a suitable N,N'-disubstituted carbodiimide, e.g. N,N'-cyclohexylcarbodiimide or, in particular, N-(3-dimethylaminopropyl)-N'-ethylcarbodiimide. Furthermore, amino esters or amido esters of the acids used as acylating agents can be formed in the presence of the starting material of the formula V to be acylated by reacting the mixture of the corresponding acid and amino starting compounds in the presence of an N,N'-disubstituted carbodiimide, e.g. N,N'-dicyclohexylcarbodiimide, and of an N-hydroxyamine or N-hydroxyamide, e.g. N-hydroxysuccinimide, if desired in the presence of a suitable base, e.g. 4-dimethylaminopyridine. Activation in situ can also be achieved by reacting with N,N,N',N'-tetraalkyluronium compounds, such as O-benzotriazol-1-yl-N,N,N',N'-tetramethyluroniu m hexafluorophosphate, O-(1,2-dihydro-2-oxo-1-pyridyl)-N,N,N',N'-tetramethyluronium tetrafluoroborate (in the presence or absence of 1,8-diaza-bicyclo [5.4.0]undec-7-ene-(1,5–5)) or O-(3,4-dihydro-4-oxo-1,2,3-benzotriazolin-3-yl) N,N,N',N'-tetramethyluronium tetrafluoroborate.

Finally, phosphoric anhydrides of the carboxylic acids of the formula VI can be prepared in situ by reacting an alkylphosphoramide, such as hexamethylphosphoramide, in the presence of a sulfonic anhydride, such as 4-toluenesulfonic anhydride, with a salt, such as a tetrafluoroborate, e.g. sodium tetrafluoroborate, or with another derivative of hexamethylphosphoramide, such as benzotriazol-1-yloxytris(dimethylamino)phosphonium hexafluoride, preferably in the presence of a racemization-lowering additive such as N-hydroxybenzotriazole.

The amino group of compounds of the formula V, which group participates in the reaction, preferably carries at least one reactive hydrogen atom, in particular when the carboxyl group, sulfonyl group or phosphoryl group which is reacting with it is present in reactive form; however, it can also itself be derivatized, e.g. by reaction with a phosphite, such as diethyl chlorophosphite, 1,2-phenylene chlorophosphite, ethyl dichlorophosphite, ethylene chlorophosphite or tetraethyl pyrophosphite. A derivative of such a compound with an amino group is, for example, also a carbamoyl halide or an isocyanate, with the amino group participating in the reaction being substituted by halocarbonyl, e.g. chlorocarbonyl, or being modified as an isocyanate group.

The condensation for preparing an amide bond can be carried out in a manner known per se, for example as described in standard works, such as "Houben-Weyl, Methoden der organischen Chemie (Methods of organic chemistry)", 4th edition, volume 15/II (1974), volume IX (1955) volume E 11 (1985), Georg Thieme Verlag, Stuttgart, "The Peptides" (E. Gross and J. Meienhofer, Eds.), volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can preferably be carried out in the presence of one of the customary condensing agents, or using carboxylic anhydrides or acyl halides, such as acyl chlorides, or activated carboxylic esters, such as p-nitrophenyl esters. Customary condensing agents are, for example, carbodiimides, e.g. diethyl-, dipropyl- and dicyclohexyl-carbodiimide or, in particular, N-(3-dimethylaminopropyl)-N'-ethylcarbodiimide, and also suitable carbonyl compounds, for example carbonylimidazole, 1,2-oxazolium compounds, e.g. 2-ethyl-5-phenyl-1,2-oxazolium-3'-sulfonate and 2-tert-butyl-5-methylisoxazolium perchlorate, or a suitable acylamino compound, e.g. 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate or, in particular, O-(1,2-dihydro-2-oxo-1-pyridyl)-N,N,N',N'-tetramethyluronium tetrafluoroborate (in the presence or absence of 1,8-diazabicyclo[5.4.0O]undec-7-ene-(1,5–5)), and also activated phosphoric acid derivatives, e.g. diphenylphosphoryl azide, diethylphosphoryl cyanide, phenyl-N-phenylphosphoroamidochloridate, bis-(2-oxo-3-oxazolidinyl)phosphinic chloride or 1-benzotriazolyloxytris(dimethylamino)phosphonium hexafluorophosphate.

If desired, an organic base is added, preferably a tertiary amine, e.g. a tri-lower alkylamine, in particular ethyldiisopropylamine or, especially, triethylamine, and/or a heterocyclic base, e.g. 4-dimethylaminopyridine or, preferably, N-methylmorpholine or pyridine.

The condensation of activated esters, reactive anhydrides or reactive cyclic amides with the corresponding amines is customarily carried out in the presence of an organic base, e.g. simple tri-lower alkylamines, e.g. triethylamine or tributylamine, or of one of the abovementioned organic bases. If desired, a condensing agent is used as well, as described for free carboxylic acids.

The condensation of acid anhydrides with amines can, for example, take place in the presence of inorganic carbonates, e.g. ammonium or alkali metal carbonates or hydrogen carbonates, such as sodium or potassium carbonate or hydrogen carbonate (if desired together with a sulfate).

Acyl chlorides, for example chlorocarbonic acid derivatives which are derived from the acid of the formula VI, are condensed with the corresponding amines, preferably in the presence of an organic amine, e.g. of the abovementioned tri-lower alkylamines or heterocyclic bases, in the presence or absence of a hydrogen sulfate or of a hydroxide, preferably of an alkali metal hydroxide such as sodium hydroxide.

The condensation is preferably carried out in an inert, aprotic, preferably water-free, solvent or solvent mixture, for example in a carboxamide, e.g. formamide or dimethylformamide, a halogenated hydrocarbon, e.g. methylene chloride, carbon tetrachloride or chlorobenzene, a ketone, e.g. acetone, a cyclic ether, e.g. tetrahydrofuran or dioxane, an ester, e.g. ethyl acetate, or a nitrile, e.g. acetonitrile, or in a mixture thereof, if desired at a reduced temperature or an elevated temperature, e.g. in a temperature range of from about −40° C. to about +100° C., preferably of from about −100° C. to about +70° C., also at from about +100° C. to +200° C. when using arylsulfonyl esters, in particular at temperatures of between 10 and 30° C., and, if desired. under an inert gas atmosphere, e.g. nitrogen atmosphere or argon atmosphere.

Aqueous, for example alcoholic, e.g. ethanol, or aromatic solvents, e.g. benzene or toluene, are also possible. Acetone can also be added, if desired, in the presence of alkali metal hydroxides as bases.

The condensation can also take place in accordance with the technique known as solid phase synthesis, which technique was devised by R. Merrifield and is described, for example, in Angew. Chem. 97, 801–812 (1985), Naturwissenschaften 71, 252–258 (1984) or in R. A. Houghten, Proc. Natl. Acad. Sci. USA 82,5131–5135 (1985).

Protected groups are set free, if desired, using the methods which are described below under "protecting group detachment".

Process c) (Preparation of an Amide Bond)

With the exception of the groups which are to participate in the reaction or which do not react under the reaction conditions, functional groups in starting materials of the formulae VII and VIII are protected, independently of each other, with one of the protecting groups mentioned under process a).

The process is completely analogous to that described under process b) if compounds Of the formula VII are employed in place of compounds of the formula V and compounds of the formula VIII are employed in place of compounds of the formula VI.

Protected groups are set free, if desired, using the methods which are described below under "protecting group detachment".

Process d) (Preparation of an Amide Bond)

In starting materials of the formula IX and the acid of the formula VIIIa which is suitable for introducing the identical acyl radicals, or their reactive derivatives, functional groups which are not to participate in the reaction, or which do not react under the reaction conditions, are protected, independently of each other, with one of the protecting groups mentioned under process a).

Those starting compounds of the formula II which are described below in the section on starting compounds are preferred as starting compounds of the formula IX which may be protected with protecting groups.

The process is completely analogous to that described under process b), with compounds of the formula IX being employed in place of compounds of the formula V and compounds of the formula VIIIa being employed in place of compounds of the formula VI.

Protected groups are set free, if desired, using the methods described below under "protecting group detachment".

Process e) (Alkylation of a Secondary Nitrogen Atom)

In starting materials of the formula I' and the formula X, or their reactive derivatives, functional groups which are not to participate in the reaction, or which do not react under 4the reaction conditions, are protected, independently of each other, with one of the protecting groups mentioned under process a).

A leaving group X is, in particular, a nucieofugic leaving group which is selected from hydroxyl which is esterified with a strong inorganic or organic acid, such as with a mineral acid, e.g. hydrohalic acid, such as hydrochloric acid, hydrobromic acid or hydriodic acid, or with a strong organic sulfonic acid, such as a lower alkanesulfonic acid which is unsubstituted or substituted, for example, by halogen, such as fluorine, or an aromatic sulfonic acid, for example a benzenesulfonic acid which is unsubstituted or substituted by lower alkyl, such as methyl, halogen, such as bromine, and/or nitro, e.g. hydroxyl which is esterified with a methanesulfonic acid, p-bromotoluenesulfonic acid or p-toluenesulfonic acid, or hydroxyl which is esterified with hydrogen azide.

The substitution can take place under the conditions of a nucleophilic substitution of the first or second order.

For example, one of the compounds of the formulae X, in which X is a leaving group with high polarizability of the electron shell, e.g. iodine, can be employed in a polar, aprotic solvent, e.g. acetone, acetonitrile, nitromethane, dimethylsulfoxide or dimethylformamide. The reaction can also be carried out in water with which an organic solvent, e.g. ethanol, tetrahydrofuran or acetone, is admixed, if desired, as solubilizing agent. The substitution reaction is carried out, if desired, at reduced or elevated temperature, e.g. in a temperature range of from about −40 to about 100° C., preferably of from about −100 to about 50° C., and, if desired, under an inert gas, e.g. under a nitrogen or argon atmosphere.

Process e) does not succeed in every case and is often only possible under special conditions; it is therefore a less preferred process.

Protected groups are set free, if desired, using the methods which are described below under "protecting group detachment".

Process f) (Reductive Alkylation of a Secondary Amino Group)

In starting materials of the formula I' and the formula X*, or their reactive derivatives, functional groups which are not to take part in the reaction, or which do not react under the reaction conditions, are protected, independently of each other, with one of the protecting groups mentioned under process a).

Examples of reactive derivatives of the compounds of the formula I are corresponding bisulfite adducts or, in particular, semiacetals or ketals of the compounds of the formula X* with alcohols, e.g. lower alkanols; or thioacetals of the compounds of the formula X* with mercaptans, e.g. lower alkane sulfides. The free aldehydes of the formula X* are preferred.

The reductive alkylation preferably takes place while hydrogenating in the presence of a catalyst, in particular of a precious metal catalyst, such as platinum or, in particular palladium, which is preferably bonded to a support material, such as carbon, or of a heavy metal catalyst, such as Raney nickel, under standard pressure or pressures of from 0.1 to 10 megapascals (MPa), or while reducing with the aid of complex hydrides, such as borohydrides, in particular alkali metal cyanoborohydrides, e.g. sodium cyanoborohydride, in the presence of a suitable acid, preferably of relatively weak acids, such as lower alkanecarboxylic acids or, in particular, of a sulfonic acid, such as p-toluenesulfonic acid, in customary solvents, for example alcohols, such as methanol or ethanol, or ethers, e.g. cyclic ethers, such as tetrahydrofuran, in the presence or absence of water.

Protected groups are set free, if desired, using the methods which are described below under "protecting group detachment".

Protecting Group Detachment

Protecting groups which are not components of the desired end product of the formula I or an intermediate, e.g. the carboxyl, amino and hydroxyl protecting groups, are detached in a manner known per se, e.g. by means of solvolysis, in particular hydrolysis, alcoholysis or acidolysis, or by means of reduction, in particular hydrogenoysis or chemical reduction, and also photolysis, if desired stepwise or simultaneously, with it also being possible to use enzymic methods. The detachment of the protecting groups is described, for example, in the standard works which are cited above in the section on "Protecting groups".

Thus, protected carboxyl, e.g. tert-lower alkoxycarbonyl, lower alkoxy carbonyl which is substituted in the 2 position by a trisubstituted silyl group or in the 1 position by lower alkoxy or lower alkylthio, or substituted or unsubstituted diphenylmethoxycarbonyl can, for example, be converted into free carboxyl by treating with a suitable acid, such as formic acid, hydrochloric acid or trifluoroacetic acid, if desired while adding a nucleophilic compound, such as phenol or anisole. Carboxyl can also be set free from lower alkoxycarbonyl with bases, such as hydroxides, e.g. alkali metal hydroxides, such as NaOH or KOH. Substituted or unsubstituted benzyloxycarbonyl can, for example, be set free by means of hydrogenolysis, i.e. by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxyl by means of reduction, e.g. by treatment with an alkali metal, such as sodium dithionite, or with a reducing metal, e.g. zinc, or a reducing metal salt, such as a chromium (II) salt, e.g. chromium(II) chloride, customarily in the presence of a hydrogen-yielding agent which, together with the metal, can produce nascent hydrogen, such as an acid, first and foremost a suitable carboxylic acid, such as a lower alkanecarboxylic acid which is unsubstituted or substituted, for example, by hydroxyl, e.g. acetic acid, formic acid, glycolic acid, diphenylylgcolic acid, lactic acid, mandelic acid, 4-chloromandelic acid or tartaric acid, or of an alcohol or thiol, with water preferably being added. It is also possible to convert 2-halogeno-lower alkoxycarbonyl (if desired after converting a 2-bromo-lower alkoxycarbonyl group into a corresponding 2-iodo-lower alkoxycarbonyl group) or aroylmethoxycarbonyl into free carboxyl by treatment with a reducing metal or metal salt as described above. Aroylmethoxycarbonyl can also be cleaved by treatment with a nucleophilic, preferably salt-forming reagent, such as sodium thiophenoxide or sodium iodide. 2-(Trisubstituted silyl)-lower alkoxycarbonyl, such as 2-tri-lower alkylsilyl-lower alkoxycarbonyl, can also be converted into free carboxyl by treatment with a salt of hydrofluoric acid which yields the fluoride anion, such as an alkali metal fluoride, e.g. sodium or potassium fluoride, if desired in the presence of a macrocyclic polyether ("crown ether"), or with a fluoride of an organic quaternary base, such as tetra-lower alkylammonium fluoride or tri-lower alkylaryl-lower alkylammonium fluoride, e.g. tetraethylammonium fluoride or tetrabutylammonium fluoride, in the presence of an aprotic, polar solvent, such as dimethyl sulfoxide or N,N-dimethylacetamide. Carboxyl which is protected as organic silyloxycarbonyl, such as tri-lower alkylsilyloxycarbonyl, e.g. trimethylsilyloxycarbonyl, can be set free in a customary manner solvolytically, e.g. by treatment with water, an alcohol or acid, or additionally fluoride, as described above. Esterified carboxyl can also be set free enzymically, for example with esterases or suitable peptidases, e.g. using trypsin.

A protected amino group is set free in a manner which is known per se and which differs depending on the nature of the protecting groups, preferably by means of solvolysis or reduction. Lower alkoxycarbonylamino, such as tert-butoxycarbonylamino, can be cleaved in the presence of acids, for example mineral acids, e.g. a hydrohalic acid, such as hydrochloric acid or hydrobromic acid, or of sulfuric acid or phosphoric acid, preferably of hydrochloric acid, or of strong organic acids, such as trihaloacetic acid, e.g. trifluoroacetic acid, or formic acid, in the presence or absence of polar solvents, such as water, or ethers, preferably cyclic ethers, such as dioxane, or nitriles, such as acetonitrile, while 2-halogeno-lower alkoxycarbonylamino (if desired after converting a 2-bromo-lower alkoxycarbonylamino group into a 2-iodo-lower alkoxycarbonylamino group), or directly dissolved in a liquid organic carboxylic acid, such as formic acid, aroyl methoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroyimethoxycarbonylamino can also be cleaved by treatment with a nucieophilic, preferably salt-forming reagent, such as sodium thiophenoxide, and 4-nitrobenzyloxycarbonylamino can also be cleaved by treatment with an alkali metal dithionite, e.g. sodium dithionite. Substituted or unsubstituted diphenylmethoxycarbonylamino, tert-lower alkoxycarbonylamino or 2-(trisubstituted silyl)-lower alkoxycarbonylamino, such as 2-tri-lower alkyl-silyl-lower alkoxycarbonylamino, can be set free by treatment with a suitable acid, e.g. formic acid or trifluoroacetic acid, while substituted or unsubstituted benzyloxycarbonylamino can be set free, for example by means of hydrogenolysis, i.e. by treatment with hydrogen in the presence of a suitable hydrogenation catalyst, such as a platinum or palladium catalyst, substituted or unsubstituted triarylmethylamino or formylamino can be set free, for example by treatment with an acid, such as mineral acid, e.g. hydrochloric acid, or an organic acid, e.g. formic, acetic or trifluoroacetic acid, if desired in the presence of water, and an amino group which is protected as silylamino can be set free, for example by means of hydrolysis or alcoholysis. An amino group which is protected with 2-haloacetyl, e.g. 2-chloroacetyl, can be set free by treatment with thiourea in the presence of a base, or with a thiolate salt, such as an alkali metal thiolate of thiourea, and subsequent solvolysis, such as alcoholysis or hydrolysis, of the resulting substitution product. Amino is set free from trifluoroacetylamino by, for example, hydrogenolysis with bases, such as alkali metal hydroxides or alkali metal carbonates, such as $Na_2CO_3$ or $K_2CO_3$, in polar solvents, e.g. alcohols, such as methanol, in the presence or absence of water, at temperatures of between 0 and 100° C., in particular at reflux temperature. An amino group which is protected with 2-(trisubstituted silyl)-lower alkoxycarbonyl, such as 2-tri-lower alkylsilyl-lower alkoxycarbonyl, can also be converted into the free amino group by treatment with a fluoride anion-yielding salt of hydrofluoric acid, as specified above in connection with the release of a correspondingly protected carboxyl group. A 1-aryl-lower alkylmethyl protecting group, in which the lower alkyl radical is preferably branched in the 1 position, such as 1-methyl-1-phenylethyl, can be detached, in particular, in the presence of a strong acid, such as sulfuric acid (e.g. 80% sulfuric acid) in aqueous solution, at preferred temperatures of between −10 and 30° C., in particular at about 0° C.

Silyl which is bonded directly to a hetero atom, such as nitrogen, an example of such silyl being trimethylsilyl, can also be detached using fluoride ions.

Amino which is protected in the form of an azido group is converted into free amino by, e.g. reduction, for example by means of catalytic hydrogenation with hydrogen in the presence of a hydrogenation catalyst, such as platinum oxide, palladium or Raney nickel, by means of reduction using mercapto compounds, such as dithiothreitol or mercaptoethanol, or else by means of treating with zinc in the presence of an acid, such as acetic acid. The catalytic hydrogenation is preferably carried out in an inert solvent, such as a halogenated hydrocarbon, e.g. methylene chloride, or else in water or a mixture of water and an organic solvent, such as an alcohol or dioxane, at from about 20° C. to 25° C., or else with cooling or heating.

A hydroxyl group which is protected with a suitable acyl group, a tri-lower alkylsilyl group or with substituted or unsubstituted 1-phenyl-lower alkyl is set free in analogy with a correspondingly protected amino group. A hydroxyl group which is protected with 2,2-dichloroacetyl is set free, for example, by means of alkaline hydrolysis, while a hydroxyl group which is protected with tert-lower alkyl or with a 2-oxa- or 2-thia-aliphatic or -cycloaliphatic hydrocarbon radical is set free by means of acidolysis, e.g. by treatment with a mineral acid or a strong carboxylic acid, e.g. trifluoroacetic acid. Adjacent amino and hydroxyl groups which are together protected by means of a bivalent protecting group, preferably, for example, a methylene group which is substituted once or twice by lower alkyl, such as by lower alkylidene, e.g. isopropylidene, cycloalkylidene, e.g. cyclohexylidene, or benzylidene, can be set free by means of acidic solvolysis, particularly in the presence of a mineral acid or a strong organic acid. A tri-lower alkylsilyl group is also detached by means of acidolysis, e.g. by means of a mineral acid, preferably hydrofluoric acid, or a strong carboxylic acid. 2-Halogeno-lower alkoxycarbonyl is removed by means of the above-mentioned reducing agents, e.g. a reducing metal, such as zinc, reducing metal salts, such as chromium(II) salts, or by means of sulfur compounds, for example sodium dithionite or, in particular, sodium sulfide and carbon disulfide.

When more than one protected functional groups are present, the protecting groups can, if desired, be selected such that more than one such group can be detached at the same time, or they can also be chosen such that they are not all detached simultaneously but, instead, detached in a desired sequence, with the corresponding intermediates being obtained; for example detachment of trifluoroacetyl as amino protecting group by means of base catalysis, e.g. with $K_2CO_3$ in methanol/water, and subsequent detachment of tert-butoxycarbonyl as amino protecting group, for example with HCl in dioxane or acetonitrile (in the presence or absence of water) or with formic acid, or selective detachment of 1-methyl-1-phenylethyl as amino protecting group using sulfuric acid; or, in a general manner acidolytically, as by treatment with trifluoroacetic acid, or with hydrogen and a hydrogenation catalyst, such as a palladium/carbon catalyst.

Additional Procedural Steps

In the additional procedural steps which are carried out if desired, starting compound functional groups which are not to participate in the reaction can be unprotected or be in protected form, for example protected with one or more of the protecting groups which are specified above under process a). The protecting groups can be retained in the final products or be detached, wholly or in part, using one of the methods specified under "Protecting group detachment".

Salts of compounds of the formula I having a salt-forming group can be prepared in a manner which is known per se. Thus, acid addition salts of compounds of the formula I can be obtained, for example, by treatment with an acid or a suitable anion exchange reagent.

Salts can be converted into the free compounds in a customary manner, for example by treatment with a suitable basic agent.

Stereoisomeric mixtures, e.g. mixtures of diastereomers, can be resolved into the corresponding isomers in a manner known per se using suitable separation methods. Thus, diastereomeric mixtures can be resolved into the individual diastereomers by means of fractional crystallization, chromatography, solvent partition and the like. This resolution can be effected both at the stage of one of the starting products and in association with the compounds of the formula I themselves.

In a compound of the formula I in which $R_5$ is phenyl, this phenyl radical can be hydrogenated, for example by means of catalytic hydrogenation, in particular in the presence of heavy metal oxides, such as rhodium/platinum mixed oxides, e.g. using the Nishimura catalyst, preferably in a polar solvent, such as an alcohol, e.g. methanol or ethanol, at temperatures of between 0 and 8° C., in particular of between 10 and 40° C., and under a preferred hydrogen pressure of from 1 to 10 atm, preferably under about standard pressure. In a compound of the formula I in which $R_6$ and $R_7$, together with the linking nitrogen, are piperidino, a 4-lower alkyl group, e.g. methyl, can be introduced by reaction with a lower alkyl halide or lower alkylarylsulfonate, such as a lower alkyl iodide or lower alkyltoluenesulfonate, e.g. methyl iodide or tert-butyl iodide, preferably in the presence of celsium carbonate in a mixture of a cyclic ether, such as dioxane, and an N,N-di-lower alkyl-lower alkanecarboxamide, such as dimethylformamide, at preferred temperatures of between −10 and 40° C., in particular of between 0 and about 30° C.

General Process Conditions

All the procedural steps which are cited in the present text can be carried out under reaction conditions which are known per se, preferably under the reaction conditions which are specifically mentioned, in the absence or, usually, the presence of solvents or diluents, preferably those which are inert towards the reagents employed and dissolve these reagents, in the absence or presence of catalysts, condensing agents or neutralizing agents, e.g. ion exchangers, such as cation exchangers, e.g. in the $H^+$ form, depending on the nature of the reaction and/or the reactants, at reduced, normal or elevated temperature, e.g. in a temperature range of from about −10° C. to about 190° C., preferably of from about −80° C. to about 150° C., e.g. at from −80 to −60° C., at room temperature, at from −20 to 40° C. or at the boiling point of the solvent employed, under atmospheric pressure or in a sealed vessel, if desired under pressure, and/or in an inert atmosphere, e.g. under an argon atmosphere or nitrogen atmosphere.

All the starting compounds and intermediate compounds can be in the form of salts, provided salt-forming groups are present. These compounds can also be in the form of salts during the reaction, provided this does not interfere with the reaction.

At all reaction stages, isomeric mixtures which arise can be resolved into the individual isomers, e.g. diastereomers or enantiomers, or be resolved into any desired mixtures of isomers, e.g. racemates or diastereomeric mixtures, for example in analogy with the methods which are described under the "Additional procedural steps".

In specific cases, for example in the case of hydrogenations, it is possible to achieve stereoselective reactions, thereby, for example, facilitating isolation of individual isomers.

The solvents from which those which are suitable for each particular reaction can be selected include, for example, water, esters, such as lower alkyl-lower alkanoates, e.g. diethyl acetate, ethers, such as aliphatic ethers, e.g. diethyl ether, or cyclic ethers, e.g. tetrahydrofuran, liquid aromatic hydrocarbons, such as benzene or toluene, alcohols, such as methanol, ethanol or 1- or 2-propanol, nitrites, such as acetonitrile, halohydrocarbons. such as methylene chloride, acid amides, such as dimethylformamide, bases, such as heterocyclic nitrogen bases, e.g. pyridine, carboxylic anhydrides, such as lower alkanoic anhydrides, e.g. acetic anhydride, cyclic, linear or branched hydrocarbons, such as cyclohexane, hexane or isopentane, or mixtures of these solvents, e.g. aqueous solutions, unless otherwise indicated in the description of the processes. Such solvent mixtures can also be used during the working-up, for example by means of chromatography or partition.

The invention also relates to those embodiments of the process in which a compound which is obtainable as an intermediate at any stage is used as the starting material and the missing steps are then carried out or in which the process is discontinued at any stage or in which a starting compound is formed under the reaction conditions or is used in the form of a reactive derivative or salt, or in which a compound which is obtainable by the process according to the invention is produced under the process conditions and subjected to further processing in situ. In this context, those starting compounds are preferably used which lead to the compounds which are described above as being preferred, in particular as being particularly preferred, first and foremost those which are preferred and/or most especially preferred.

Compounds of the formula I are preferably prepared in analogy with the processes and process steps which are specified in the examples.

The compounds of the formula I, including their salts, can also be obtained in the form of hydrates, or their crystals can, for example, include the solvent which is used for the crystallization.

Pharmaceutical Preparations

The invention also relates to pharmaceutical preparations which comprise compounds of the formula I, in particular of the formula Ia.

The pharmacologically utilizable compounds of the present invention can be used, for example, to produce pharmaceutical preparations which comprise an effective quantity of the active compound together, or in a mixture, with a significant quantity of inorganic or organic, solid or liquid, pharmaceutically utilizable carrier substances.

The invention also includes a pharmaceutical composition (preparation) which is suitable for administration to homeothermic animals, in particular humans, for treating or preventing a disease which responds to inhibition of a retroviral protease, in particular a retroviral aspartate protease, such as HIV-I gag protease or else HIV-II gag protease, e.g. for treating or preventing a retroviral disease such as AIDS or its preliminary stages, which composition comprises a quantity of a compound of the formula I, or of a pharmaceutically acceptable salt thereof, which is effective for inhibiting the retroviral protease, together with at least one pharmaceutically acceptable carrier material.

The pharmaceutical preparations according to the invention are preparations for enteral, such as nasal, rectal or oral, or parenteral, such as intramuscular or intravenous, administration to homeotherms (humans and animals) which comprise an effective dose of the pharmacological active compound either alone or together with a significant quantity of a pharmaceutically utilizable carrier material. The dosage of the active compound depends on the homeothermic species, the bodyweight, the age and the individual state of health, and on individual pharmacokinetic conditions, on the disease to be treated and on the mode of administration.

The invention also relates to a method for treating diseases which are caused by viruses, in particular retroviruses, in particular AIDS or its preliminary stages, which comprises administering a therapeutically effective quantity of a compound of the formula I, or of a pharmaceutically utilizable salt thereof, according to the invention to a homeotherm in particular, e.g. a human, who is in need of such treatment on account of one of the said diseases, in particular AIDS or its preliminary stages. The dose quantities to be administered to homeotherms. e.g. humans of about 70 kg in body weight, are between about 3 mg and about 3 g, preferably between about 10 mg and about 1.5 g, e.g. from about 50 mg to 1000 mg per person and day, preferably divided into from 1 to 3 individual doses which can, for example, be of equal size. Children are usually given half the adult dose.

The pharmaceutical preparations comprise from about 1% to about 95%, preferably from about 20% to about 90%, of the active compound. Pharmaceutical preparations according to the invention can, for example, be in dose unit form, such as ampoules, vials, suppositories, coated tablets, tablets or capsules.

The pharmaceutical preparations of the present invention are produced in a manner known per se, e.g. using conventional solubilizing, lyophilizing, mixing, granulating or sugar-coating methods.

Use is preferably made of solutions, and also suspensions, of the active compound, specifically and in particular isotonic aqueous solutions or suspensions, with it being possible to prepare these solutions or suspensions prior to use in the case, for example, of lyophilized preparations which comprise the active substance either alone or together with a carrier material, e.g. mannitol. The pharmaceutical preparations can be sterilized and/or comprise auxiliary substances, e.g. preservatives, stabilizers, wetting agents and/or emulsifying agents, solubilizers, salts for regulating the osmotic pressure and/or buffers, and are produced in a manner known per se, for example using conventional solubilizino or lyophilizing methods. The said solutions or suspensions can comprise viscosity-increasing substances, such as sodium carboxymethyl cellulose, carboxymethyl cellulose, dextran, polyvinylpyrrolidone or gelatin.

Suspensions in oil comprise, as the oily component, the vegetable, synthetic or semisynthetic oils which are customary for injection purposes. Those which are particularly to be mentioned are liquid fatty acid esters which, as the acid component, contain a long-chain fatty acid having 8–22, in particular 12–22, carbon atoms, for example lauric acid, tridecylic acid, myristic acid, pentadecylic acid, palmitic acid, margaric acid, stearic acid, arachidic acid, behenic acid and corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has at most 6 carbon atoms and is a monohydric or polyhydric, e.g. monohydric, dihydric or trihydric alcohol, e.g. methanol, ethanol, propanol, butanol or pentanol, or their isomers, in particular, however, glycol and glycerol. Examples of fatty acid esters to be mentioned are therefore: ethyl oleate, isopropyl myristate, isopropyl palmitate, "Labrafil M 2375" (polyoxyethylene glycerol trioleate from Gatteiosse, Paris), "Miglyol 812" (triglyceride of saturated fatty acids of $C_8$ to $C_{12}$ chain length from Hüls AG, Germany), in particular, however, vegetable oils such as cottonseed oil, almond oil, olive oil, castor oil, soya bean oil and, in particular, groundnut oil or sesame oil.

The injection preparations are produced in a customary manner under sterile conditions; ampoules or vials are likewise filled, and the containers sealed, under sterile conditions.

Pharmaceutical preparations for oral use can be obtained by combining the active compound with solid carrier substances, if desired granulating a resulting mixture and processing the mixture, if desired or necessary after adding suitable auxiliary substances, into tablets, coated tablet cores or capsules. In this context, the preparations can also be incorporated into plastic supports which release the active compounds in a metered manner or allow them to diffuse.

Suitable carrier substances are, in particular, fillers, such as sugars, e.g. lactose, sucrose, mannitol or sorbitol, cellulose preparations, and/or calcium phosphates, e.g. tricalcium phosphate or calcium hydrogen phosphate, and also binders, such as starch pastes using, for example, corn starch, wheat starch, rice starch or potato starch, gelatin, gum tragacanth, methyl cellulose, hydroxypropyl methyl cellulose, sodium carboxymethyl cellulose and/or polyvinylpyrrolidone, and/or, if desired, disintegrants, such as the abovementioned starches, and also carboxymethyl starch, cross-linked polyvinylpyrrolidone, agar or alginic acid or a salt thereof, such as sodium alginate. Auxiliary substances are first and foremost flowance agents and lubricants, e.g. silicic acid, talc, stearic acid or salts thereof, such as magnesium stearate or calcium stearate, and/or polyethylene glycol. Coated tablet cores are provided with suitable coatings which can be gastric juice-resistant, with use being made, inter alia, of concentrated sugar solutions which may contain gum arabic, talc, polyvinylpyrrolidone, polyethylene glycol and/or titanium dioxide, lacquer solutions in suitable organic solvents or, for preparing gastric juice-resistant coatings, solutions of suitable cellulose preparations, such as ethyl cellulose phthalate or hydroxypropyl methyl cellulose phthalate.

Capsules are hard capsules consisting of gelatin and also soft, closed capsules consisting of gelatin and an emollient, such as glycerol or sorbitol. The hard capsules can contain the active compound in the form of a granulate, e.g. together with fillers, such as lactose, binders, such as starches, and/or glidants, such as talc or magnesium stearate, and, if desired, together with stabilizers. In capsules, the active compound is preferably dissolved or suspended in suitable oily auxiliary substances, such as fat oils, paraffin oil or liquid polyethylene glycols, with it also being possible to add stabilizers and/or antibacterial agents. Oils of this nature which are to be mentioned are, in particular, liquid fatty acid esters which, as the acid component, contain a long-chain fatty acid, for example having 8–22, in particular 12–22, carbon atoms, for example lauric acid, tridecylic acid, myristic acid, pentadecylic acid, palmitic acid, margaric acid, stearic acid, arachidic acid or behenic acid, or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has at most 6 carbon atoms and is a monohydric or polyhydric, e.g. monohydric, dihydric or trihydric alcohol, e.g. methanol, ethanol, propanol, butanol or pentanol or their isomers, especially, however, ethylene glycol, propylene glycol and glycerol. Examples of fatty acid esters which are to be mentioned are therefore: ethyl oleate. isopropyl myristate, isopropyl palmitate, "Labrafil M 2375" (polyoxyethylene glycerol trioleate from Gattefoss6, Paris), "Miglyol 812" (triglyceride of saturated fatty acids of $C_8$ to $C_{12}$ chain length from üls AG, Germany), in particular, however, vegetable oils such as cottonseed oil, almond oil, olive oil, castor oil, ground-nut oil, soya bean oil and, especially, sesame oil. Paraffin oil is also possible. Stabilizers, such as emulsifiers, wetting agents or surfactants, binders, such as starch pastes using, for example, corn starch, wheat starch, rice starch or potato starch, gelatin, gum tragacanth, methyl cellulose, hydroxypropyl methyl cellulose or hydroxypropyl cellulose (preferred), sodium carboxymethyl cellulose, cyclodextrin (s) and/or polyvinylpyrrolidone, and/or antibacterial agents can be added. Suitable emulsifiers are, in particular, oleic acid, non-ionic surfactants of the fatty acid polyhydroxyalcohol ester type, such as sorbitan monolaurate, sorbitan oleate, sorbitan stearate or sorbitan palmitate, sorbitan tristearate or sorbitan trioleate, polyoxyethylene adducts of fatty acid polyhydroxy-alcohol esters, such as polyoxyethylene sorbitan monolaurate, -oleate, -stearate, -palmitate, -tristearate or -trioleate, polyethylene glycol fatty acid esters such as polyoxyethyl stearate, polyoxyethylene glycol (300 or 400) stearate, polyethylene glycol (2000) stearate, in particular ethylene oxide-propylene oxide block copolymers of the ®Pluronic (Wyandotte Chem. Corp.; trade mark of BASF, FRG) or ®Synperonic (ICI), type. For example, if it is not soluble in the said oils, the active substance is present in suspension form, i.e. with a particle size of the active substance of between about 1 and 100 mm. Suspensions of this nature can also be used as such, i.e. without capsules.

Dyes or pigments can be added to the tablets or coated tablet coatings or capsule casings, e.g. for the purpose of identifying or labelling different active compound doses.

Starting Materials

The present invention likewise relates to novel starting materials and/or intermediates and to processes for their preparation. Preferably, those starting compounds are used, and the reaction conditions are chosen such that, the compounds which are listed as preferred are successfully prepared.

During preparation of all the starting materials, free functional groups which are not to participate in the relevant reaction can be unprotected or be in protected form, for example protected with the protecting groups which are mentioned above under process a). At suitable time points, these protecting groups can be set free using the reactions which are described under "Protecting group detachment".

The starting materials of process a) are known or, if they are novel, can be prepared by methods which are known per se, e.g. the compounds of the formula III from hydrazine or its suitable derivatives, and the compounds of the formula IV from suitable amino acids or their analogues, for example having one of the said side chains $R_3$.

The compounds of the formula III can be obtained, for example, from compounds of the formula

which are known per se or which can be prepared from hydrazine by means of protecting group insertion, as described under process a), and in which $R_8$ is hydrogen or an amino protecting group, as described above under process b), in particular tert-lower alkoxycarbonyl, such as tert-butoxycarbonyl, aryl-lower alkoxycarbonyl, such as benzyloxycarbonyl or 9-fluorenylmethoxycarbonyl, or one of the abovementioned acyl amino protecting groups, in particular trifluoroacetyl, by alkylating with a compound of the formula X, as described above under process e), or reacting the residue of the part formula

in which $R_6$ and $R_7$ have the meanings given for compounds of the formula I, by reaction of suitable carbonyl compounds of the formula X*, or reactive derivatives thereof, both defined as under process f), with the free amino group of the compound of the formula XI, or of its acylated derivatives, and subsequent reduction of the resulting hydrazone with the formation of hydrazine derivatives of the formula

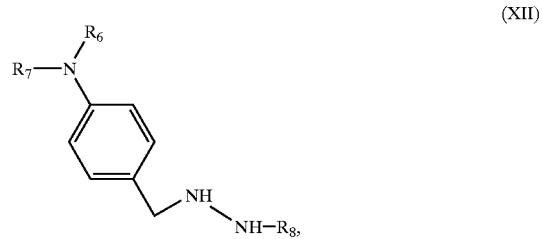

where the radicals in all the said compounds have the meanings given above and functional groups in the reagents involved which are not to participate in the reaction are protected if necessary, detaching the protecting group $R_8$ if necessary, and reacting with acids of the formula VI, or the acid derivatives thereof which are specified at that point, by means of condensation under the conditions mentioned above under process b).

The carbonyl compounds of the formula X*, or reactive derivatives thereof, as defined above under process f), which are used for preparing the compounds of the formula XII and which are suitable for introducing the residue of the part formula A are aldehydes or their reactive derivatives whose reactive carbonyl group is, after the reaction with compounds of the formula XI and the subsequent reduction, a constituent of one of the said residues of the part formula A.

The reaction of the carbonyl compounds with the compounds of the formula XI to give the corresponding hydrazones is effected under the conditions which are customary for reacting carbonyl compounds with amines, preferably in polar organic solvents, e.g. ethers, such as tetrahydrofuran or diethyl ether, alcohols, such as methanol or ethanol, carboxamides, such as dimethylformamide, or esters, such as ethyl acetate, or in aqueous solution, preferably in methanol, and also in the presence or absence of acid catalysts, e.g. carboxylic acids, such as formic acid or acetic acid, or sulfonic acids, such as p-toluenesulfonic acid, at temperatures of between 0° C. and the reflux temperature of the reaction mixture, preferably at temperatures of from 20° C. up to the reflux temperature of the reaction mixture.

Compounds of the formula

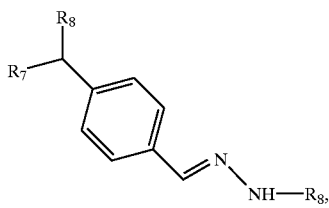
(XII*)

in which $R_5$ and $R_7$ and also Ra have the meanings given for compounds of the formula XII, are obtained.

The resulting hydrazones of the formula XII* are preferably reduced by means of hydrogenation in the presence of a suitable catalyst or using complex hydrides in the presence of acids. Suitable catalysts used for the hydrogenation are metals, such as nickel, iron, cobalt or ruthenium, or precious metals or their oxides, such as palladium or rhodium or their oxides, if desired mounted, for example, on a suitable support material, such as barium sulfate, aluminum oxide or carbon (active charcoal) or as skeleton catalysts, such as Raney nickel. Examples of customary solvents for the catalytic hydrogenation are water, alcohols, such as methanol or ethanol, esters, such as ethyl acetate, ethers, such as dioxane or tetrahydrofuran, chlorohydrocarbons, such as dichloromethane, carboxamides, such as dimethylformamide, or carboxylic acids, such as glacial acetic acid, or mixtures of these solvents. The hydrogenation is preferably effected at temperatures of from 10 to 250° C., in particular at from room temperature to 100° C., and preferably under hydrogen pressures of from 1 to 200 bar, in particular of from 1 to 10 bar, in the customary equipment. When reducing with complex hydrides, in particular borohydrides, such as alkali metal cyanoborohydrides, e.g. sodium cyanoborohydride, preference is given to adding weak acids, such as sulfonic acids, e.g. p-toluenesulfonic acid, or carboxylic acids, such as acetic acid, preferably in alcohols, such as methanol or ethanol, or mixtures thereof with water (cf., e.g., Tetrahedron 49, 8605–28 (1993)).

It is also possible to reductively alkylate compounds of the formula XI directly with compounds of the formula X*, or reactive derivatives thereof, as defined under process f), under conditions which are analogous to those described in process f).

Reaction conditions which are analogous to those described in J. Chem. Soc. Perkin 1, 1712 (1975) are also particularly preferred for preparing the compounds of the formula XI.

Compounds of the formula III can also be obtained, for example, by reacting a compound of the formula XII*, as defined above, in which $R_8$ is hydrogen (obtainable, for example, by means of protecting group detachment if $R_8$ is a protecting group), directly, with condensation under the conditions described above under process b), with acids of the formula VI, or the acid derivatives thereof which are mentioned at that point, to form compounds of the formula

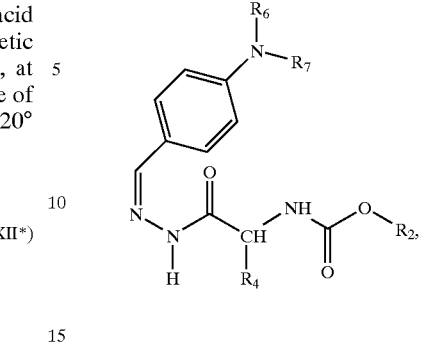
(III*)

in which the radicals have the meanings given for compounds of the formula I, and then converting these compounds, by means of reduction under conditions which are analogous to the conditions described in association with the reduction of hydrazones of formula XII*, into compounds of the formula III.

Compounds of the formula III* can also be obtained from the corresponding compounds of the formula III', which are defined as described below, by reacting these latter compounds with compounds of the formula X*, as defined above, to form the hydrazones of the formula III, under conditions which are analogous to those described above for the reaction of carbonyl compounds of the formula X* with hydrazines of the formula XI.

The compounds of the formula IV can be obtained, for example, by reducing amino acids of the formula

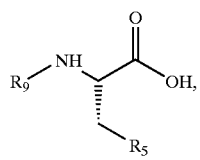
(XIII)

in which $R_9$ is hydrogen or, in particular, one of the amino protecting groups specified under process a), in particular tert-lower alkoxycarbonyl, such as tert-butoxycarbonyl, aryl-lower alkoxycarbonyl, such as benzyloxycarbonyl or 9-fluoroenylmethoxycarbonyl, or one of the acyl amino protecting groups which are specified at that point, in particular trifluoroacetyl. and $R_5$ has the meanings given for compounds of the formula I, to form aldehydes of the formula

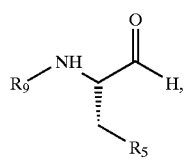
(XIV)

in which the radicals have the last-mentioned meanings, subsequently reacting these aldehydes with an ylide compound, preferably a sulfur ylide compound, to form an epoxide of the formula

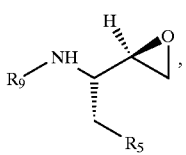

(XV)

in which the radicals have the last-mentioned meanings, if necessary detaching the protecting group $R_9$ (the resulting free amino compound in which $R_9$=hydrogen can, for example, be stable as an acid addition salt) and finally acylating the amino group of the resulting compound with an acid of the formula VII, in which the radicals have meanings which were given in association with their definition, under suitable conditions which are analogous to the conditions described for process b).

Amino acids of the formula XIII are, for example, reduced to the corresponding aldehydes of the formula XIV by means of reduction to the corresponding alcohols and subsequent oxidation to give the said aldehydes.

The reduction to give the alcohols (a free compound, or (if necessary after protecting group insertion, as described under process a)) a compound which is N-protected with a protecting group $R_9$, of the formula

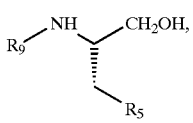

(XIII*)

in which the radicals have the meanings given for compounds of the formula XII) is effected, for example, by hydrogenating the acid halides, or other activated carboxylic acid derivatives which are mentioned under process b), under the conditions specified for hydrogenating hydrazones which are obtained from compounds of the formula XII, using diborane or using complex hydrides, such as sodium borohydride. The subsequent oxidation of the resulting alcohols can be effected, for example, by oxidizing the hydroxyl group with a sulfoxide, for example dimethyl sulfoxide, in the presence of a reagent which activates the hydroxyl group, such as an acyl chloride, e.g. oxalyl chloride, in inert solvents, e.g. a halogenated hydrocarbon, such as dichloromethane, and/or an acyclic or cyclic ether, such as tetrahydrofuran, at from −80 to 0° C., e.g. from −78 to −50° C., or by oxidizing, for example with chromic acid or its derivatives, such as pyridinium chromate or tert-butyl chromate, dichromate/sulfuric acid, sulfur trioxide in the presence of heterocyclic bases, such as pyridine/$SO_3$, and also nitric acid, manganese dioxide or selenium oxide, in water, organic solvents, such as halogenated solvents, e.g. methylene chloride, carboxamides, such as dimethylformamide, or di-lower alkyl sulfoxides, such as dimethyl sulfoxide, in the presence or absence of basic amines, e.g. tri-lower alkylamines, such as triethylamine, at temperatures of between −50 and 100° C., preferably at from −10 to 50° C., or by catalytically dehydrogenating, e.g. in the presence of metallic silver, copper, copper chromium oxide or zinc oxide at from approx. 200 to 400° C. (in a catalyst tube) and subsequently cooling rapidly. It is also possible to oxidize with 2,2,6,6-tetramethyl-1-piperidinyloxy in the presence of NaOCl (cf. Anelli et al., Org. Synth. 69, 212 (1990)).

It is also possible directly to reduce the amino acids to the aldehydes, for example by hydrogenating in the presence of a partially poisoned palladium catalyst or by reducing the corresponding amino acid esters, e.g. the lower-alkyl esters, such as ethyl esters, with complex hydrides, e.g. borohydrides, such as sodium borohydride, or preferably aluminum hydrides, e.g. lithium aluminum hydride, lithium tri-tert-butoxyaluminohydride or, in particular, diisobutylaluminum hydride, in apolar solvents, e.g. in hydrocarbons or aromatic solvents, such as toluene, at from −100 to 0° C., preferably at from −70 to −30° C., and then converting into the corresponding semicarbazones, e.g. using the corresponding acid salts of semicarbazones, such as semicarbazide hydrochloride, in aqueous solvent systems, such as alcohol/water, e.g. ethanol/water, at temperatures of between −20 and 60° C., preferably of from 0 to 30° C., and reacting the resulting semicarbazone with a reactive aldehyde, e.g. formaldehyde, in an inert solvent, for example a polar organic solvent, e.g. a carboxamide, such as dimethylformamide, at temperatures of between −30 and 60° C., preferably of from 0 to 30° C., and then an acid, for example a strong mineral acid, such as hydrohalic acid, in aqueous solution, in the presence or absence of the previously employed solvent, at temperatures of between −40 and 50° C., preferably of between −10 and 30° C. The corresponding esters are isolated by reacting the amino acids with the corresponding alcohols, for example ethanol, in analogy with the conditions used under process b) in association with the condensation, for example by reacting with inorganic acid halides, such as thionyl chloride, in organic solvent mixtures, such as mixtures of aromatic and alcoholic solvents, e.g. toluene and ethanol, at temperatures of between −50 and 50° C., preferably of between −10 and 20° C.

In a particularly preferred manner, the compounds of formula XIV are prepared under conditions which are analogous to the reaction conditions specified in J. Org. Chem. 47, 3016 (1982) or J. Org. Chem. 43, 3624 (1978).

A sulfur ylide which is suitable for converting compounds of the formula XIV into the epoxides of the formula XV is, for example, a dialkylsulfonium methylide, e.g. dimethylsulfonium methylide, an alkyl- or phenyl-dialkylaminosulfoxonium methylide, e.g. methyl- or phenyl-dimethylaminosulfoxonium methylide, or a dialkylsulfoxonium methylide, e.g. dimethyl- or diethylsulfoxonium methylide.

The relevant sulfur ylide compound is expediently prepared in situ from the corresponding sulfonium salt or sulfoxonium salt and a base, e.g. sodium hydride, in a dipolar aprotic solvent, e.g. dimethyl sulfoxide, or an ether, e.g. tetrahydrofuran or 1,2-dimethoxyethane, and then reacted with the compounds of the formula XIV. The reaction is normally carried out at room temperature. with cooling, e.g. down to −20° C., or with moderate heating, e.g. up to 40° C. The sulfide, sulfinamide or sulfoxide which is formed at the same time is removed during the subsequent aqueous working-up.

In a particularly preferred manner, the reaction with a sulfur ylide is effected in analogy with the conditions specified in J. Org. Chem. 50, 4615 (1985).

A compound of the formula XV can also be obtained from a compound of the formula XIV, as defined above, by reacting it with a tri-lower alkylsilylmethyl Grignard compound, e.g. prepared from the corresponding halomethylsilane, such as chloromethyltrimethyl-silane, in an inert solvent, e.g. an ether, such as dioxane or diethyl ether, at temperatures of between 0 and 50° C., e.g. between room temperature and about 40° C., then eliminating with removal of the silyl radical and formation of a double bond, e.g. using a Lewis acid, such as BF$_3$, with an amino protecting group R$_8$ which is present preferably also being detached, in an inert solvent, e.g. an ether, such as diethyl ether, or a halohydrocarbon, such as dichloromethane, or a mixture thereof, at temperatures of between −50° C. and the reflux temperature, in particular of between 0 and 30° C., if necessary acylating once again with insertion of an amino protecting group R$_{12}$, as defined above, and oxidizing the resulting double bond to give the oxirane, preferably using a percarboxylic acid, e.g. m-chloroperbenzoic acid or monoperphthalic acid (e.g. as the magnesium salt), in an inert solvent, e.g. halogenated hydrocarbon, such as dichloromethane, or alcohols, such as methanol, lower alkanoylnitriles, such as acetonitrile, water or mixtures thereof, at temperatures of between −20° C. and the reflux temperature of the mixture, e.g. at from 10 to 50° C.

Preferably, compounds of the formula IV are prepared by proceeding directly from an alcohol of the formula XIII*, as defined above, which alcohol may also be commercially available, reacting this alcohol with an acid of the formula VII, or a reactive derivative thereof, as defined for process c), under the conditions specified at that point, with, if necessary, protecting groups, as described under process a), being introduced and, at suitable timepoints, as described under "Protecting group detachment", being removed, with a compound being obtained which is analogous to the compound of the formula XIII*, in which the corresponding acyl radical from the acid of formula XIII is present in place of R$_9$; oxidizing the resulting compound under conditions which are analogous to those specified for oxidizing alcohols of the formula XIII* to give the corresponding aldehyde of the formula

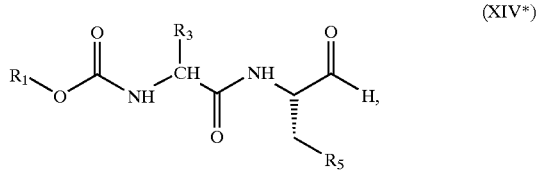

(XIV*)

in which the radicals have the meanings given for compounds of the formula I, and then converting this aldehyde into the compound of the formula IV, for example using an ylide compound, as described in association with the conversion of compounds of the formula XIV into compounds of the formula XV.

The starting materials for processes b), c) and d) are known or, if they are novel, can be prepared using methods which are known per se, for example a compound of the formula V can be prepared from suitable hydrazine derivatives of the formula XII, in which R$_8$ is a protecting group and the remaining radicals have the meanings given for compounds of the formula V, and suitable epoxides of the formula IV, in which the radicals have the meanings given for compounds of the formula I (process b), while a compound of the formula VI can be prepared from suitable hydrazine derivatives of the formula III, in which the radicals have the meanings given for compounds of the formula I, and suitable epoxides of the formula XV, in which R$_9$ is a protecting group and the remaining radicals have the meanings given for compounds of the formula I (process c), and the compound of the formula IX can be prepared from suitable hydrazine derivatives of the formula XII, in which R$_8$ is hydrogen and the remaining radicals have the meanings given for compounds of the formula I, and suitable epoxides of the formula XV, in which R$_9$ is a protecting group and the remaining radicals have the meanings given for compounds of the formula I (process d), in analogy with process a), if desired using and detaching protecting groups, as described under process a) or under "Protecting group detachment", with the protecting groups R$_8$ and R$_9$ preferably having the meanings given above in association with the definition of compounds of the formula XI and XIII, respectively.

Compounds of the formula I', in which the substituents have the abovementioned meanings, can be prepared, for example, from compounds of the formula III',

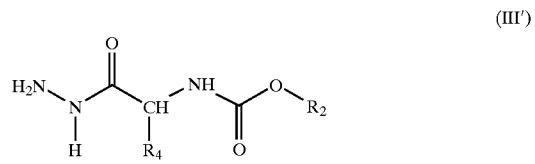

(III')

in which the radicals have the meanings given for compounds of the formula I, in a manner analogous to that described in process b), by reacting them with a compound of the formula IV, with functional groups which are present and which are not to participate in the reaction being protected as in process b), and with it being possible to set these groups free after the reaction.

Compounds of the formula III' can be obtained from compounds of the formula XI, as defined above, by reacting the latter with an acid of the formula VI, or a reactive acid derivative thereof, in which the radicals have the abovementioned meanings, in an analogous manner to that described for the reaction of compounds of the formula XII with an acid of the formula VI, and, if necessary, subsequently detaching the protecting group R$_8$ using one of the methods described under "Protecting group detachment".

When two amino protecting groups are present, these groups can be identical or different.

The amino protecting groups which are mentioned above under process a) are, for example, used as amino protecting groups. Preference is given to the corresponding compounds in which the protecting groups are selected from those which are specified as being preferred for R$_8$ and R$_9$ in compounds of the formulae XI and XIII, respectively.

The protected compounds of the formula I are prepared, for example, using one of the previously mentioned processes, in particular from compounds of the formula III and IV, with, if desired, functional groups in these compounds being protected with protecting groups as described under process a).

The acids of the formulae VI, VIII and VIIIa, and also the compounds of the formula X, and the aldehydes which are used for preparing the compounds of the formula XII, and which are suitable for introducing the residue of the part formula A, can be prepared by methods which are known per se, insofar as they are not already known.

The acids of the formula VI are prepared by the reaction of derivatives of lower alkoxy or lower alkoxy-lower alkoxycarboxylic acid which are suitable for introducing lower alkoxy- or lower alkoxy-lower alkoxycarbonyl radicals, for example by the reaction of the corresponding di-lower alkyl dicarbonates (in particular dimethyl dicarbonate; Aldrich, Buchs, Switzerland) or preferably lower alkyl halo-, such as chloro-formates (in particular methyl chloroformate, Fluka, Buchs, Switzerland), with amino acids of the formula (XVI)

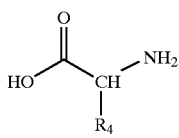

in which $R_4$ has the meanings given for compounds of the formula VI, under conditions which are analogous to those described for acylation under process b), in particular in an aqueous alkali metal hydroxide solution, e.g. aqueous sodium hydroxide solution, in the presence of dioxane at temperatures of between 20 and 100° C., in particular of between 50 and 70° C.

Correspondingly, the compounds of the formula VIII can be obtained from amino acids of the formula (XVII)

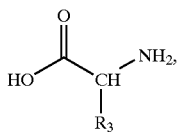

in which $R_3$ has the meanings given for compounds of the formula I, and those of the formula VIIIa can be obtained from amino acids of the formula (XVIII)

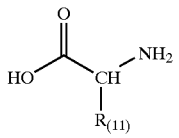

in which $R_{(II)}$ has the meanings given for compounds of the formula VIIIa, by reaction with derivatives of lower alkoxy- or lower alkoxy-lower alkoxycarboxylic acid which are suitable for introducing lower alkoxy- or lower alkoxy-lower alkoxycarbonyl radicals.

The amino acids of the formulae XVI, XVII or XVIII are known or can be prepared using methods which are known per se. They are preferably (with regard to the α-carbon atom) in the (S) form.

Compounds of the formula IV can also be prepared by condensing a compound of the formula XIX (XIX)

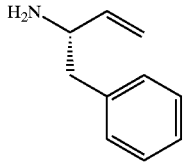

with a compound of the formula XVIII, as defined above. The condensation with an acid of the formula VIII, or an acid derivative thereof, is effected under conditions which are analogous to those specified above under process e). A compound of the formula XX, (XX)

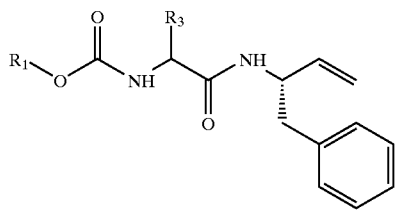

in which $R_1$ and $R_3$ have the meanings given for compounds of the formula I, is obtained.

A compound of the formula IV, as defined above, is obtained by means of epoxidation with oxygen or, preferably, chemically bound oxygen, for example in hydroperoxides, hydrogen peroxide or peroxy acids, such as perbenzoic acid, performic acid, peracetic acid, monoperoxiphthalic acid, pertungttic acid or, in particular, m-chloroperbenzoic acid; in inert solvents, such as ether, e.g. diethyl ether, or chlorinated hydrocarbons, such as chloroform or dichloromethane, at preferred temperatures of between −20 and 50° C.

The starting material of the formula XIX is preferably obtained by reacting a compound of the formula XIV, in which $R_5$ is phenyl and $R_9$ is a protecting group, with a Grignard reagent which introduces the methylidene group, in particular with the trimethylsilylmethyl Grignard reagent ($ClMgCH_2Si(CH_3)3$— which can be prepared from chloromethyltrimethylsilane (Fluka, Buchs, Switzerland) under customary conditions for preparing Grignard compounds) in an inert solvent, such as an ether, e.g. diethyl ether, at a preferred temperature of from −65 to 0° C. and then detaching the hydroxyl group and the trimethylsilyl group, for example using boron trifluoride in an ether, such as diethyl ether, at preferred temperatures of from −20 to 30° C., with simultaneous detachment of the protecting group $R_8$ (in particular in the case of detaching the tert-butoxycarbonyl protecting group) or with subsequent protecting group detachment as described under "Protecting group detachment".

The synthesis can also be effected proceeding from a compound of the formula XIV, in which $R_5$ is phenyl and $R_9$ is a protecting group, and using a suitable Wittig reagent, such as methyltriphenylphosphonium bromide or methyltridhenylphosphonium iodide in the presence of a strong base, such as sodium amide, at temperatures of from −90 to 0° C., followed by detachment of the protecting group $R_9$ in accordance with the conditions specified under "Protecting group detachment".

Compounds of the formula X* are known, can be prepared by methods which are known per se, or can be prepared, for example, as follows:

By proceeding from a compound of the formula XXI, (XXI)

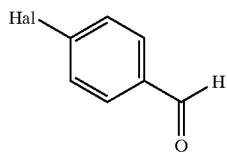

in which Hal is halogen, in particular bromine or chlorine or, especially, fluorine, the corresponding compounds of the formula X* can be obtained by means of reaction with pyrrolidine, piperidine, 4-lower alkylpiperidine or 1,2,4-triazole, if necessary in the presence of a catalyst, such as Cu(I)O, in a suitable basic medium, such as pyridine; or of a base, such as an alkali metal carbonate, in particular potassium carbonate, in suitable solvents, such as di-lower alkyl sulfoxides, e.g. dimethyl sulfoxide; at elevated temperatures, e.g. at from 40° C. up to the reflux temperature, in particular at reflux temperature or about 100° C.

Compounds of the formula X can be obtained, in accordance with standard methods, from the corresponding compounds of the formula X* by reducing the aldehyde function to a hydroxymethyl group (for example using complex hydrides, such as lithium aluminum hydride in ethanol, disiamylborane in tetrahydrofuran, sodium borohydride in the presence of lithium chloride in diglycol or sodium borohydride in ethanol) and subsequently introducing the radical X by esterifying with a strong inorganic or organic acid, such as with a mineral acid, e.g. a hydrohalic acid, such as hydrochloric acid, hydrobromic acid or hydriodic acid, or with a strong organic sulfonic acid, such as a lower alkanesulfonic acid which is unsubstituted or substituted, for example by halogen, such as fluorine, or an aromatic sulfonic acid, e.g. a benzenesulfonic acid which is unsubstituted or substituted by lower alkyl, such as methyl, halogen, such as bromine, and/or nitro, e.g. with methanesulfonic acid, p-bromotoluenesulfonic acid or p-toluenesulfonic acid, or with hydrazoic acid. Thus, halogen radicals X can be introduced by reaction with inorganic acid halides, such as thionyl or phosphoryl halides (e.g. the thionyl or phosphoryl chlorides, bromides or iodides); or the remaining compounds of the formula X can be obtained by reaction with other corresponding organic or inorganic acids, such as strong organic sulfonic acids (e.g. employed as the acid chlorides).

Starting materials can also be prepared by the methods specified in EP 0 521 827 or be obtained from the sources cited in that document; alternatively, they are known, can be prepared by methods which are known per se or are commercially available.

Starting materials for preparing compounds of the formula I are preferably prepared in analogy with the processes and process steps which are described in the examples.

The following starting materials according to the invention are particularly preferred (insofar as radicals are not specifically defined, the meanings given in association with defining compounds of the formula I apply in each case):

(1) Compounds of the formula XII;
(2) Compounds of the formula XII*;
(3) Compounds of the formula III;
(4) Compounds of the formula V;
(5) Compounds of the formula VII;
(6) Compounds of the formula IX;
(7) Compounds of the formula X;
(8) Compounds of the formula X*
(9) Compounds of the formula II

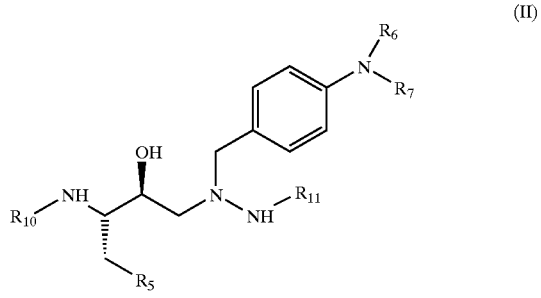

(II)

in which $R_{10}$ and $R_{11}$ are amino protecting groups which are different from each other and which are selected from those specified under process a), in particular tert-lower alkoxycarbonyl, such as tert-butoxycarbonyl, or an acylamino protecting group, in particular trifluoroacetyl; preferably, $R_{10}$ is trifluoroacetyl and $R_{11}$ is tert-butoxycarbonyl; (these compounds are compounds of the formula XI which are protected on both amino groups);

(10) Compounds of the formula XXII,

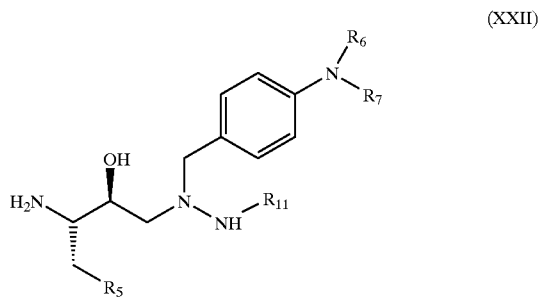

(XXII)

in which $R_{11}$ is an amino protecting group as defined for compounds of the formula XXII, in particular tert-butoxycarbonyl;

Insofar as salt-forming groups are present, the compounds mentioned above under (1) to (15) as starting compounds can also be present in the form of a salt.

The following examples serve to illustrate the invention; they are not intended to restrict the scope of the present invention in any way.

$R_f$ ratio of distance migrated to mobile solvent front in TLC;

HPLC gradients:

| | |
|---|---|
| $HPLC_{20-100}$ | 20% → 100% of a) in b) over 20 min. |
| $HPLC_{20-100(12')}$ | 20% → 100% of a) in b) over 12 min and then 100% of a) for 8 min. |

Mobile solvent a): acetonitrile+0.05% TFA; mobile solvent b): water+0.05% TFA. Column (250×4.6 mm) filled with C18 Nucleosil reversed-phase material (silica gel which is covalently derivatized with octadecylsilanes and which is of 5 μm mean particle size, Macherey & Nagel, Duren, FRG). Detection by means of UV absorption at 254 nm. The retention times ($t_{Ret}$) are given in minutes. Flow rate 1 ml/min.

The other abbreviations which are used have the following meanings:

| | |
|---|---|
| abs. | absolute (indicates that the solvent is water-free) |
| anal. | elemental analysis |
| Boc | tert-butyloxycarbonyl (protecting group) |
| brine | saturated sodium chloride solution |
| calc. | calculated |
| DBU | 1,8-diazabicyclo[5.4.0]undec-7-ene-(1,5-5) (Fluka, Buchs, Switzerland) |
| decomp. | with decomposition |
| DIPE | diisopropyl ether |
| DMF | dimethylformamide |
| DMSO | dimethyl sulfoxide |
| DMSO-$D_6$ | perdeuterated DMSO |
| EDC | N-ethyl-N'-(3-dimethylaminopropyl)carbodiimide hydrochloride (Fluka, Buchs, Switzerland) |
| Ether | diethyl ether |
| FAB MS | fast atom bombardment mass spectroscopy |
| fnd. | found |
| h | hour(s) |
| HOAc | acetic acid |
| HOBT | 1-hydroxybenzotriazole |
| Hünig's base | N-ethyldiisopropylamine |
| HV | high vacuum |
| Hyflo | Hyflo Super Cel ® (kieselguhr-based filtration aid; obtainable from Fluka, Buchs, Switzerland) |
| i.a. | inter alia |
| min | minute(s) |
| m.p. | melting point |
| NMM | N-methylmorpholine |
| $^1$H NMR | proton-magnetic nuclear resonance |
| Pd/C | palladium on active charcoal |
| $R_f$ | Ratio of distance migrated to solvent front in TLC |
| RT | room temperature |
| RE | rotary evaporator |
| sat. | saturated |
| THF | tetrahydrofuran (dist. over Na/benzophenone) |
| TLC | thin layer chromatography |
| TPTU | O-(1,2-dihydro-2-oxo-1-pyridyl)-N,N,N',N'-tetramethyluronium tetrafluoroborate (Fluka, Buchs, Switzerland) |

Origin of some amino acid derivatives which are used as starting compounds:

N-methoxycarbonyl-(L)-valine (*Chem. Lett.* 705 (1980))

N-methoxycarbonyl-(L)-isoleucine (*Chem. Lett.* 705 (1980))

(2R)-[(1'S)-Boc-amino-2'-phenylethyl]oxirane (*J. Org. Chem.* 50, 4615 (1985))

(2R)-[(1'S)-(trifluoroacetyl)amino-2'-phenylethyl]oxirane (EP 0 521 827, p. 78, Ex. 16d)

EXAMPLE 1

1-[p-(N,N-Diethylamino)phenyl]-4(S)-hydroxy-2-[N-(N-methoxycarbonyl-(L)-tert-leucyl)amino]-5(S)-[N-(N-methoxycarbonyl-(L)-valyl)amino]-6-pheny-2-azahexane In analogy with Example 2, 1.05 ml (7.5 mmol) of triethylamine are added to a solution of 0.37 g (2 mmol) of N-methoxycarbonyl-(L)-tert-leucine (Example 2h), 0.7 g (3.75 mmol) of EDC and 0.33 g (2.5 mmol) of HOBT in 8 ml of DMF and the whole is stirred at RT for 10 min. After that, 0.95 g (1.25 mmol) of 1-[p-(N,N-diethylamino) phenyl]-4(S)-hydroxy-2-amino-5(S)-[N-(N-methoxycarbonyl-(L)-valyl)amino]-6-phenyl-2-azahexane hydrochloride (Example 5b), dissolved in 2 ml of DMF, is added and the whole is stirred at RT for 2.75 h. The reaction mixture is evaporated under reduced pressure. After having been taken up in methylene chloride, the residue is washed consecutively with water, aqueous sodium bicarbonate and brine. The organic phase is then concentrated and the residue is digested in DIPE. The title compound is obtained after filtering off and drying.

TLC: $R_f$=0.55 (ethyl acetate). $HPLC_{20-100}$: $t_{ret}$=10.90; FAB MS $(M+H)^+$=685.

EXAMPLE 2

1-[p-(N,N-Diethylamino)phenyl]-4(S)-hydroxy-5(S)-2,5-bis[N-(N-methoxycarbonyl-(L)-tert-leucyl) amino]-6-phenyl-2-azahexane 0.42 ml (2.5 mmol) of Hünig's base is added to a solution of 0.21 g (1.1 mmol) of N-methoxycarbonyl-(L)-tert-leucine (Example 2h) and 0.327 g (1.1 mmol) of TPTU in 3 ml of DMF and the whole is stirred at RT for 10 min. After that, 0.63 g (1 mmol) of 1-[p-(N,N-diethylamino)phenyl]-4(S)-hydroxy-2-amino-5(S)-[N-(N-methoxycarbonyl-(L)-tert-leucyl)amino]-6-phenyl-2-azahexane hydrochloride, dissolved in 2 ml of DMF, is added and the whole is stirred at RT for 21 h. The reaction mixture is poured onto 25 ml of water and the resulting solid is filtered off and washed twice with water. The moist suction filter residue is taken up in methylene chloride and this solution is washed twice with aqueous sodium bicarbonate solution, once with water and once with brine. After the organic phase has been separated off, the solvent is removed from it and the residue is dried under reduced pressure. The crude product is digested in DIPE and, after having been filtered off, is dried in a heated desiccator at 45° C. This results in the title compound:

TLC: $R_f$=0.57 (ethyl acetate). $HPLC_{20-100}$: $t_{ret}$=11.47; FAB MS $(M+H)^+$=699.

Alternative Method:

In analogy with Example 1, 180 ml of Hünig's base are added to 45.4 g (240 mmol) of N-methoxycarbonyl-(L)-tert-leucine and 71.2 g (240 mmol) of TPTU in 300 ml of DMF and the whole is stirred at RT for 15 min. After that, 57 g (120 mmol) of 1-[p-(N,N-diethylamino)-phenyl]-4(S)-hydroxy-2-amino-5(S)-amino-6-phenyl-2-azahexane hydrochloride (Example 2g), dissolved in 120 ml of DMF, are added and the whole is stirred at RT for 26 h. After working-up in the same way as described in Example 1, the residue is dissolved in methanol and the title compound is precipitated by adding ether and then filtered off. The suction filter residue is washed once again with ether and dried in a heated desiccator at 50° C., with the title compound thereby being obtained.

The Starting Materials are Obtained as Follows:

2a) N-1-(tert-Butyloxycarbonyl)-N-2-[p-(N,N-diethylamino)phenyl]-methylidene]hydrazone A solution of 100 g (564 mmol) of p-N,N-diethylaminobenzaldehyde (Fluka, Buchs, Switzerland) and 74.4 g (564 mmol) of tert-butyl carbazate (Fluka, Buchs, Switzerland) in 800 ml of ethanol is stirred at 78° C. for 5 h. The reaction mixture is cooled down in an ice bath and diluted with 200 ml of water. The resulting precipitate is filtered off, washed with ethanol/water 10:1 and dried, with the title compound thereby being obtained.

M.p.: 175° C.; TLC: $R_f$=0.4 (hexane/ethyl acetate: 2/1); $HPLC_{20-100}$: $t_{ret}$=9.35.

2b) N-1-(tert-Butyloxycarbonyl)-N-2-[p-(N,N-diethylamino)benzyl]hydrazine 20 g (68.7 mmol) of N-1-(tert-butyloxycarbonyl)-N-2-[p-(N,N-diethylamino)phenyl]-methylidene]hydrazone (Example 2a) and 2 g of 5% Pd/C in 100 ml of methanol are hydrogenated at RT for 20 min under standard pressure. The catalyst is filtered off and the solvent is removed. The title compound is obtained as a pale yellow oil, which is subjected to further processing without purification.

TLC: $R_f$=0.36 (hexane/ethyl acetate: 2/1). $HPLC_{20-100}$: $t_{ret}$=7.10.

2c) 1-[p-(N,N-Diethylamino)phenyl]-4(S)-hydroxy-2-(tert-butyloxycarbonyl)amino-5(S)-(trifluoroacetyl)amino-6-phenyl-2-azahexane A solution of 69.9 g (270 mmol) of (2R)-[(1'S)-(trifluoroacetyl)amino-2'-phenylethyl]oxirane and 79 g (270 mmol) of N-1-(tert-butyloxycarbonyl)-N-2-[p-(N,N-diethylamino)benzyl]-hydrazine (Example 2b) in a total of 1500 ml of isopropanol is stirred at 90° C. for about 20 h and, after having been cooled down, concentrated by ⅓. The resulting crystalline mass is treated with DIPE and filtered off through a suction filter. The suction filter residue is washed with DIPE and dried at 60° C. under reduced pressure, with the title compound thereby being obtained.

M.p.: 160° C. TLC: $R_f$=0.45 (hexane/ethyl acetate 2:1). $HPLC_{20-100}$: $t_{ret}$=12.78. FAB MS $(M+H)^+$=553.

2d) 1-[p-(N,N-Diethylamino)phenyl]-4(S)-hydroxy-2-(tert-butyylocarbonyl)amino-5(S)-amino-6-phenyl-2-azahexane 710 ml of a 1 M aqueous solution of potassium carbonate are added to 78 g (141 mmol) of 1-[p-(N,N-diethylamino)phenyl]-4(S)-hydroxy-2-(tert-butyloxycarbonyl)amino-5(S)-(trfifuoroacetyl)amino-6-phenyl-2-azahexane (Example 2c) in 2100 ml of methanol (slightly warmed) and the whole is stirred at 60° C. for 3 h under argon. After that, the methanol is removed in vacuo and the residue is dissolved in ethyl acetate. The organic phase is washed consecutively with water, dilute brine and brine and then concentrated and the residue cooled with ice water. The title compound which crystallizes out during this procedure is then digested in hexane and, after having been filtered off, dried at 60° C. The title compound is obtained in the form of colorless crystals.

M.p.: 97° C. TLC: $R_f$=0.40 (methylene chloride/methanol: 9/1). $HPLC_{20-100}$: $t_{ret}$=8.60. FAB MS $(M+H)^+$=457.

2e) 1-[p-(N,N-Diethylamino)phenyl]-4(S)-hydroxy-2-(tert-butyloxycarbonyl)amino-5(S)-[N-(N-methoxycarbonyl-(L)-tertleucyl)amino]-6-phenyl-2-azahexane 1.3 ml (7.5 mmol) of Hünia's base is added to a solution of 0.625 g (3.3 mmol) of N-methoxycarbonyl-(L)-tert-leucine and 0.98 g (3.3 mmol) of TPTU in 10 ml of DMF and the whole is stirred at RT for 10 min. After that, 1.36 g (3 mmol) of 1-[p-(N,N-diethylamino)-phenyl]-4(S)-hydroxy-2-(tert-butyloxycarbonyl)amino-5(S)-amino-6-phenyl-2-azahexane, dissolved in 4 ml of DMF, are added and the whole is stirred at RT for 17 h. The reaction mixture is then poured onto 70 ml of water and the resulting solid is filtered off and washed twice with water. The moist suction filter residue is taken up in methylene chloride and this solution is washed twice with an aqueous solution of sodium bicarbonate, once with water and once with brine. After separating the organic phase, the solvent is removed and the residue is dried under reduced pressure, with the title compound thereby being obtained:

TLC: $R_f$=0.55 (ethyl acetate). $HPLC_{20-100}$: $t_{ret}$=10.90. FAB MS $(M+H)^+$=628.

2f) 1-[p-(N,N-Diethylamino)phenyl]-4(S)-hydroxy-2-amino-5(S)-[N-(N-methoxycarbonyl-(L)-tert-leucyl)amino]-6-phenyl-2-azahexane Hydrochloride 30 ml of 4N hydrogen chloride in dioxane (Aldrich, Buchs, Switzerland) are added to a solution of 1.85 g (3 mmol) of 1-[p-(N,N-diethylamino)phenyl]-4(S)-hydroxy-2-(tert-butyloxycarbonyl)amino-5(S)-[N-(N-methoxycarbonyl-(L)-tert-leucyl)amino]-6-phenyl-2-azahexane in 1.5 ml of DMF and the whole is stirred at RT for approximately 2.25 h. After that, the solvent is removed and toluene is added twice to the residue, with each addition being followed by evaporation. The residue is taken up in dioxane and this solution is lyophilized, with the title compound thereby being obtained.

TLC: $R_f$=0.6 (methylene chloride/methanol: 9/1). $HPLC_{20-100}$: $t_{ret}$=8.33.

2 g) 1-[p-(N,N-Diethylamino)phenyl]-4(S)-hydroxy-2-amino-5(S)-amino-6-phenyl-2-aza-hexane Hydrochloride 850 ml of a 4M solution of hydrogen chloride in dioxane is added to a solution of 57 g (124.8 mmol) of 1-[p-(N,N-diethylamino)phenyl]-4(S)-hydroxy-2-(tert-butyloxycarbonyl)-amino-5(S)-amino-6-phenyl-2-azahexane (Example 2d) in 200 ml of DMF and the whole is stirred at RT for 4 h. After that, the mixture is concentrated and treated firstly with dioxane and then with toluene with subsequent evaporation taking place in each case. The residue is triturated twice with dioxane and decanted off. The oily title compound which is obtained in this way is subjected to further processing without any additional purification.

TLC: $R_f$=0.15 (methylene chloride/methanol: 9/1). $HPLC_{20-100}$: $t_{ret}$=7.02. FAB MS $(M+H)^+$=357.

2h) N-(Methoxycarbonyl)-(L)-tert-leucine 23.5 ml (305 mmol) of methyl chlorotormate are added, over a period of 20 min, to a solution of 20 g (152 mmol) of (L)-tert-leucine (=2(S)-amino-3,3-dimethylbutyric acid=(L)-α-tert-butylglycine; Fluka, Buchs, Switzerland) in a mixture of 252 ml (504 mmol) of a 2N aqueous solution of sodium hydroxide and 80 ml of dioxane, and the reaction solution is heated at 60° C. for 14 h. After the reaction solution has cooled down to room temperature, it is washed twice with methylene chloride. The aqueous phase is acidified to pH 2 with 4N aqueous hydrochloric acid and extracted three times with ethyl acetate. The organic extracts are combined, dried ($Na_2SO_4$) and concentrated by evaporation. During this procedure, the product begins to harden. Digestion of the hardened solid with hexane yields the title compound as a white powder. M.p. 106–108° C.

EXAMPLE 3

1-[p-(N,N-Diethylamino)phenyl]-4(S)-hydroxy-2-[N-(N-methoxycarbonyl-(L)-valyl]amino]-5(S)-[N-(N-methoxycarbonyl-(L)-tert-leucyl)amino]-6-phenyl-2-azahexane In analogy with Example 2, 0.42 ml of Hünig's base is added to 0.193 g (1.1 mmol) of N-methoxycarbonyl-(L)-valine and 0.327 g (1.1 mmol) of TPTU in 3 ml of DMF and the whole is stirred at RT for 10 min. After that, 0.63 g (1 mmol) of 1-[p-(N,N-diethylamino)-phenyl]-4(S)-hydroxy-2-amino-5(S)-[N-(N-methoxycarbonyl-(L)-tert-leucyl) amino]-6-phenyl-2-azahexane hydrochloride (Example 2f), dissolved in 2 ml of DMF, is added and the mixture is stirred at RT for 21 h. After working-up in the same way as described for Example 2, the residue is digested in DIPE and the title compound is filtered off. The suction filter residue is washed once again with DIPE and dried in a heated desiccator at 45° C. TLC: $R_f$0.50 (ethyl acetate). $HPLC_{20-100}$: $t_{ret}$=10.93; FAB MS $(M+H)^+$=685.

EXAMPLE 4

1-[p-(N,N-Diethylamino)phenyl]-4(S)-hydroxy-2-[N-(N-methoxycarbonyl-(L)-isoleucyl)amino]-5(S)-[N-(N-methoxycarbonyl-(L)-tert-leucyl)amino]-6-phenyl-2-azahexane In analogy with Example 2, 0.42 ml of Hünig's base is added to 0.21 g (1.1 mmol) of N-methoxycarbonyl-(L)-isoleucine and 0.327 g (1.1 mmol) of TPTU in 3 ml of DMF and the whole is stirred at RT for 10 min. After that, 0.63 g (1 mmol) of 1-[p-(N,N-diethylamino)-phenyl]-4(S)-hydroxy-2-amino-5(S)-[N-(N-methoxycarbonyl-(L)-tert-leucyl)amino]-6-phenyl-2-azahexane hydrochloride (Example 2f), dissolved in 2 ml of DMF, is added and the mixture is stirred at RT for 21 h. After working-up in the same manner as described in Example 2, the residue is digested in DIPE and the title compound is filtered off. The suction filter residue is washed once again with DIPE and dried in a heated desiccator at 45° C.

TLC: $R_f$=0.54 (ethyl acetate). $HPLC_{20\text{-}100}$: $t_{ret}$=11.49; FAB MS $(M+H)^+$=699.

EXAMPLE 5

1-[p-(N,N-Diethylamino)phenyl]-4(S)-hydroxy-2-[N-(N-methoxycarbonyl-(L)-isoleucyl)amino]-5(S)-[N-(N-methoxycarbonyl-(L)-valyl)amino]-6-phenyl-2-azahexane In analogy with Example 2, 0.78 ml of DBU is added to 0.23 g (1.25 mmol) of N-methoxycarbonyl-(L)-isoleucine and 0.37 g (1.25 mmol) of TPTU in 4 ml of DMF and the whole is stirred at RT for 10 min. After that, 0.95 g (1.25 mmol) of 1-[p-(N,N-diethylamino)phenyl]-4(S)-hydroxy-2-amino-5(S)-[N-(N-methoxycarbonyl-(L)-valyl)amino]-6-phenyl-2-azahexane hydrochloride, dissolved in 2 ml of DMF, is added and the mixture is stirred at RT for 5 h. After working up in the same manner as described for Example 2, the residue is digested in DIPE and the title compound is filtered off. The suction filter residue is washed once again with DIPE and dried in a heated desiccator at 40° C.

TLC: $R_f$=0.50 (ethyl acetate). $HPLC_{20\text{-}100}$: $t_{ret}$=10.87; FAB MS $(M+H)^+$=685.

The Starting Material is Obtained as Follows:

5a) 1-[p-(N,N-Diethlamino)phenyl]-4(S)-hydroxy-2-(tert-butyloxycarbonyl)amino-5(S)-[N-(N-methoxycarbonyl-(L)-valyl)amino]-6-phenyl-2-azahexane In analogy with Example 2e, 1.5 ml of Hünig's base are added to 0.77 g (4.3 mmol) of N-methoxycarbonyl-(L)-valine and 1.3 g (4.3 mmol) of TPTU in 20 ml of DMF and the whole is stirred at RT for 5 min. After that, 2.0 g (4.3 mmol) of 1-[p-(N,N-diethylamino)phenyl]-4(S)-hydroxy-2-(tert-butyloxycarbonyl)amino-5(S)-amino-6-phenyl-2-azahexane (Example 2d), dissolved in DMF, are added and the mixture is stirred at RT for 2 h. After working up in the same manner as described for Example 2e, the residue is digested in DIPE and the title compound is filtered off. The suction filter residue is washed once again with DIPE and dried in a heated desiccator at 60° C., with the title compound thereby being obtained. TLC: $R_f$=0.80 (methylene chloride/methanol). $HPLC_{20\text{-}100}$: $t_{ret}$=11.79.

5b) 1-[p-(N,N-Diethylamino)phenyl]-4(S)-hydroxy-2-amino-5(S)-[N-(N-methoxycarbonyl-(L)-valyl)amino]-6-phenyl-2-azahexane Hydrochloride In analogy with Example 2f, 25 ml of a 4N solution of hydrogen chloride in dioxane (Aldrich, Buchs, Switzerland) are added to a solution of 1.53 g (2.5 mmol) of 1-[p-(N,N-diethylamino)-phenyl]-4(S)-hydroxy-2-(tert-butyloxycarbonyl)amino-5(S)-[N-(N-methoxycarbonyl-(L)-valyl)amino]-6-phenyl-2-azahexane in 1 ml of DMF and the whole is stirred at RT for approximately 2.5 h. After that, the solvent is removed and toluene is added (twice) to the residue with evaporation taking place on each occasion. The residue is taken up in dioxane and this solution is lyophilized, with the title compound thereby being obtained.

TLC: $R_f$=0.6 (methylene chloride/methanol: 9/1). $HPLC_{20\text{-}100}$ $t_{ret}$=7.66.

EXAMPLE 6

1-[p-(N,N-Diethylamino)phenyl]-4(S)-hydroxy-2-[N-(N-methoxacarbonyl-(L)-valyl)amino]-5(S)-[N-(N-methoxycarbonyl-(L)-isoleucyl)amino]-6-phenyl-2-azahexane In analogy with Example 2, 0.42 ml of Hünig's base is added to 0.193 g (1.1 mmol) of N-methoxycarbonyl-(L)-valine and 0.327 g (1.1 mmol) of TPTU in 3 ml of DMF and the whole is stirred at RT for 10 min. After that, 0.53 g (1 mmol) of 1-[p-(N,N-diethytamino)-phenyl]-4(S)-hydroxy-2-amino-5(S)-[N-(N-methoxycarbonyl-(L)-isoleucyl)amino]-6-phenyl-2-azahexane hydrochloride, dissolved in 2 ml of DMF, is added and the mixture is stirred at RT for 21 h. After working up in the same manner as described for Example 2, the residue is digested in DIPE and the title compound is filtered off. The suction filter residue is washed once again with DIPE and dried in a desiccator, with the title compound thereby being obtained.

TLC: $R_f$=0.5 (ethyl acetate). $HPLC_{20\text{-}100}$: $t_{ret}$=11.03; FAB MS $(M+H)^+$=684.

The Starting Material is Obtained as Follows:

6a) 1-[p-(N,N-Diethylamino)phenyl]-4S)-hydroxy-2-(tert-butyloxycarbonyl)amino-5(S)-[N-(N-methoxycarbonyl-(L)-isoleucyl)amino]-6-phenyl-2-azahexane In analogy with Example 2e, 1.05 ml of DBU are added to 0.56 g (3 mmol) of N-methoxycarbonyl-(L)-isoleucine and 0.91 g (3 mmol) of TPTU in 10 ml of DMF and the whole is stirred at RT for 5 min. After that, 1.36 g (3 mmol) of 1-[p-(N,N-diethylamino)phenyl]-4(S)-hydroxy-2-(tert-butyloxycarbonyl)amino-5(S)-amino-6-phenyl-2-azahexane (Example 2d), dissolved in 4 ml of DMF, are added and the mixture is stirred at RT for 3 h. After working up in the same manner as described for Example 2e, the residue is digested in DIPE and the title compound is filtered off. The suction filter residue is washed once again with DIPE and dried in a desiccator.

TLC: $R_f$=0.70 (methylene chloride/methanol: 9/1). $HPLC_{20\text{-}100}$: $t_{ret}$=12.34.

6b) 1-[p-(N,N-Diethylamino)phenyl]-4(S)-hydroxy-2-amino-5(S)-[N-(N-methoxycarbonyl-(L)-isoleucyl)amino]-6-phenyl-2-azahexane Hydrochloride In analogy with Example 2f, 20 ml of a 4N solution of hydrogen chloride in dioxane (Aldrich, Buchs, Switzerland) are added to a solution of 1.2 g (2 mmol) of 1-[p-(N,N-diethylamino)-phenyl]-4(S)-hydroxy-2-(tert-butyloxycarbonyl)amino-5(S)-[N-(N-methoxycarbonyl-(L)-isoleucyl)amino]-6-phenyl-2-azahexane in 1 ml of DMF and the whole is stirred at RT for about 2.5 h. After that, the solvent is removed and toluene is added twice to the residue with evaporation then taking place on each occasion. The residue is taken up in dioxane and this solution is lyophilized, with the title compound thereby being obtained.

TLC: $R_f$=0.55 (methylene chloride/methanol: 9/1). HPLC$_{20-100}$: $t_{ret}$=8.37.

EXAMPLE 7

1-[p-(N,N-Diethylamino)phenyl]-4(S)-hydroxy-5(S)-2,5bis[N-(N-methoxycarbonyl-(L)-isoleucylamino]-6-phenyl-2-azahexane In analogy with Example 2, 0.42 ml of Hünig's base is added to 0.21 g (1.1 mmol) of N-methoxycarbonyl-(L)-isoleucine and 0.327 g (1.1 mmol) of TPTU in 3 ml of DMF and the whole is stirred at RT for 10 min. After that, 0.52 g (1 mmol) of 1-[p-(N,N-diethylamino)-phenyl]-4(S)-hydroxy-2-amino-5(S)-[N-(N-methoxycarbonyl-(L)-isoleucyl)amino]-6-phenyl-2-azahexane hydrochloride (Example 6b), dissolved in 2 ml of DMF, is added and the mixture is stirred at RT for 19 h. After working up in the same manner as described for Example 2, the residue is digested in DIPE and the title compound is filtered off. The suction filter residue is washed once again with DIPE and dried in a heated desiccator at 45° C., with the title compound thereby being obtained.

TLC: $R_f$=0.5 (ethyl acetate). HPLC$_{20-100}$: $t_{ret}$=11.64; FAB MS (M+H)$^+$=699.

EXAMPLE 8

1-[p-(Pyrrolidin-1-yl)phenyl]-4(S)-hydroxy-2-[N-(N-methoxycarbonyl-(L)-valyl)amino]-5(S)-[N-(N-methoxycarbonyl-(L)-tert-leucyl)amino]-6-phenyl-2-azahexane 175 mg (1 mmol) of N-methoxycarbonyl-(L)-valine and 300 mg (1 mmol) of TPTU in 3 ml of DMF are stirred at RT for 20 min, after which 600 mg (1 mmol) of 1-[p-(pyrrolidin-1-yl)-phenyl]-4(S)-hydroxy-2-amino-5(S)-[N-(N-methoxycarbonyl-(L)-tert-leucyl)amino]-6-phenyl-2-azahexane hydrochloride (Example 8f) and 0.56 ml (5 mmol) of triethylamine in 4 ml of DMF are added and the whole is stirred at RT for 16 h. The reaction mixture is added dropwise onto 100 ml of water and the resulting suspension is stirred at RT for 20 min. The precipitate is filtered off and taken up in methylene chloride. The organic phase is washed consecutively with water, a sat. solution of sodium bicarbonate/water 1:1, water and brine. After removing the solent, the title compound residue is obtained in a solid form from DIPE/methylene chloride.

TLC: $R_f$=0.40 (ethyl acetate). HPLC$_{20-100}$: $t_{ret}$=12.84. FAB MS (M+H)$^+$=683.

The Starting Material is Prepared as Follows:

8a) N-1-(tert-Butyloxycarbonyl)-N-2-{4-[(pyrrolidin-1-yl)phenyl]-methylidene}hydrazone A solution of 24.68 g (142.7 mmol) of p-pyrrolidinobenzaldehyde (Lancaster, Strasbourg, France) and 17.9 g (135.7 mmol) of tert-butyl carbazate (Fluka, Buchs, Switzerland) in 350 ml of ethanol is stirred at 78° C. overnight. The reaction mixture is cooled in an ice bath, in association with which the title compound crystallizes out. The precipitate is filtered off, washed with cold ethanol and ether and then dried, with the title compound thereby being obtained.

M.p.: 180–181° C.; TLC: $R_f$=0.64 (ethyl acetate); HPLC$_{20-100}$: $t_{ret}$=14.40.

8b) N-1-(tert-Butyloxycarbonyl)-N-2-[p-(pyrrolidin-1-yl)benzyl]hydrazine 26.8 g (92.6 mmol) of N-1-(tert-butyloxycarbonyl)-N-2-{p-[(pyrrolidin-1-yl)phenyl]-methylidene}hydrazone (Example 8a) and 5 g of 5% Pd/C in 150 ml of THF are hydrogenated at RT for 8 h under standard pressure. The catalyst is filtered off and the solvent is removed. The title compound is obtained as a pale yellow oil which is subject to further processing without being purified.

TLC: $R_f$=0.43 (hexane/ethyl acetate 1:1). HPLC$_{20-100}$: $t_{ret}$=9.63.

8c) 1-[p-(Pyrrolidin-1-yl)phenyl]-4(S)-hydroxy-2-(tert-butyloxycarbonyl)amino-5(S)-(trifluoroacetyl)amino-6-phenyl-2-azahexane A solution of 32 g (123.5 mmol) of (2R)-[(1'S)-(trifluoroacetyl)amino-2'-phenylethyl]oxirane and 27 g (92.6 mmol) of N-1-(tert-butyloxycarbonyl)-N-2-[p-(pyrrolidin-1-yl)benzyl]hydrazine (Example 8b) in a total of 800 ml of isopropanol is stirred at 80° C. for approximately 12 h and at RT for approximately 48 h. A gelatinous suspension is obtained which is filtered through a suction filter. The precipitate is washed with isopropanol and ether and dried, with the title compound thereby being obtained.

M.p.: 169–170° C. TLC: $R_f$=0.50 (hexane/ethyl acetate 1:1). $^1$H NMR (CD$_3$OD; 200 MHz) i.a.: 7.3–7.1/m (5H); 7.12 and 6.48/in each case d, J=6 (2×2H); 1.33/s (9H).

8d) 1-[p-(Pyrrolidin-1-yl)phenyl]-4(S)-hydroxy-2-(tert-butyloxycarbonyl)amino-5(S)-amino-6-phenyl-2-azahexane 150 ml of a 1M aqueous solution of potassium carbonate are added to 16.4 g (29.8 mmol) of 1-[p-(pyrrolidin-1-yl)phenyl]-4(S)-hydroxy-2-(tert-butyloxycarbonyl)amino-5(S)-(trifluoroacetyl)amino-6-phenyl-2-azahexane (Example 8c) in 750 ml of methanol (slightly heated) and the whole is stirred at 60° C. for 6 h under argon. After that, the methanol is removed in vacuo and the residue is dissolved in ethyl acetate. The organic phase is washed consecutively with water, dilute brine and brine, then concentrated down to approximately 100 ml and cooled with ice water. In association with this, the title compound crystallizes out. It is obtained in the form of colorless crystals.

M.p.: 151–153° C. TLC: $R_f$=0.44 (methylene chloride/methanol/sat. ammonia 300:50:1). HPLC$_{20-100}$: $t_{ret}$=9.61.

8e) 1-[p-(Pyrrolidin-1-yl)phenyl]-4(S)-hydroxy-2-(tert-butyloxycarbonyl)amino-5(S)-[N-(N-methoxycarbonyl-(L)-tert-leucyl)amino]-6-phenyl-2-azahexane 12.3 ml (88 mmol) of triethylamine are added to a solution of 3.3 g (17.6 mmol) of N-methoxycarbonyl-(L)-tert-leucine, 6.7 g (35.2 mmol) of EDC and 4.8 g (35.2 mmol) of HOBT in 90 ml of DMF (degassed under vacuum) and the whole is stirred at RT for 20 min. After that, 4 g (8.8 mmol) of 1-[p-(pyrrolidin-1-yl)phenyl]-4(S)-hydroxy-2-(tert-butyloxycarbonyl)amino-5(S)-amino-6-phenyl-2-azahexane (Example 8d), dissolved in 20 ml of DMF, are added and the mixture is stirred at RT for 16 h. The reaction mixture is concentrated by evaporation and the residue is taken up in ethyl acetate/water. The organic phase is separated off and subsequently washed consecutively with water, 5% sodium bicarbonate solution (twice), water, dilute brine and brine, with the title compound thereby being obtained. The solvent is removed and the residue is recrystallized from ether in an ice bath, with the title compound thereby being obtained.

TLC: $R_f$=0.13 (hexane/ethyl acetate 1:1). $^1$H NMR (CD$_3$OD; 200 MHz) i.a.: 7.3–7.1/m (5H); 7.12 and 6.48/in each case d, J=6 (2×2H); 1.32/s (9H); 0.86/s (9H).

8f) 1-[p-(Pyrrolidin-1-yl)phenyl]-4(S)-hydroxy-2-amino-5(S)-[N-(N-methoxycarbonyl-(L-tert-leucyl)amino]-6-phenyl-2-azahexane Hydrochloride A mixture consisting of 4.85 g (7.75 mmol) of 1-[p-(pyrrolidin-1-yl)phenyl]-4(S)-hydroxy-2-(tert-butyloxycarbonyl)amino-5(S)-[N-(N-methoxycarbonyl-(L)-tert-leucyl)amino]-6-phenyl-2-azahexane (Example 8e) in 140 ml of 4N hydrogen chloride in dioxane (Aldrich, Buchs, Switzerland) is stirred at RT for approximately 4 h. After that, the solvent is removed and the residue is treated with dioxane (once) and toluene (twice) followed by evaporation on each occasion. The residue is dissolved in dioxane and this solution is concentrated down with the residue being treated with ether. In association with this, the title compound is obtained in crystalline form.

HPLC$_{20-100}$: $t_{ret}$=8.31. FAB MS (M+H)$^+$=526.

EXAMPLE 9

1-[p-(Pyrrolidin-1-yl)phenyl]-4(S)-hydroxy-2-[N-(N-methoxycarbonyl-(L)-isoleucyl)amino]-5(S)-[N-(N-methoxycarbonyl-(L)-tert-leucyl)amino]-6-phenyl-2-azahexane In analogy with Example 8, the title compound is obtained, after working-up, from 600 mg (1 mmol) of 1-[p-(pyrrolidin-1-yl)phenyl]-4(S)-hydroxy-2-amino-5(S)-[N-(N-methoxycarbonyl-(L)-tert-leucyl)amino]-6-phenyl-2-azahexane hydrochloride (Example 8f) and 0.56 ml (5 mmol) of triethylamine in 4 ml of DMF and also 190 mg (1 mmol) of N-methoxycarbonyl-(L)-isoleucine and 300 mg of TPTU in 3 ml of DMF.

M.p.: 158–161° C. TLC: $R_f$=0.42 (ethyl acetate). FAB MS (M+H)$^+$=697.

EXAMPLE 10

1-[p-(Pyrrolidin-1-yl)phenyl]-4(S)-hydroxy-5(S)-2,5bis[N-(N-methoxycarbonyl-(L)-tert-leucyl)amino]-6-phenyl-2-azahexane In analogy with Example 8e, the title compound is obtained, after working-up, from 1.2 g (2 mmol) of 1-[p-(pyrrolidin-1-yl)phenyl]-4(S)-hydroxy-2-amino-5(S)-[N-(N-methoxycarbonyl-(L)-tert-leucyl)amino]-6-phenyl-2-azahexane hydrochloride (Example 8f), 0.76 g (4 mml) of N-methoxycarbonyl-(L)-tert-leucine, 1.5 g (8 mmol) of EDC, 1.1 g (8 mmol) of HOBT and 3.4 ml (24 mmol) of triethylamine in 30 ml of DMF; it is then obtained in crystalline form by chromatography on silica gel (hexane/ethyl acetate 1:1) and digesting with ether.

M.p.: 208–211 ° C. TLC: $R_f$=0.47 (ethyl acetate). FAB MS (M+H)$^+$=697.

EXAMPLE 11

1-[p-(Pyrrolidin-1-yl)phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane In analogy with Example 8, the title compound is obtained, after working-up, from 337 mg (1 mmol) of 1-[p-(pyrrolidin-1-yl)phenyl]-4(S)-hydroxy-2-amino-5(S)-[N-(N-methoxycarbonyl-(L)-valyl)-amino]-6-phenyl-2-azahexane (Example 11b) and 0.42 ml (3 mmol) of triethylamine in 3 ml of DMF (solution A), 190 mg (1 mmol) of N-methoxycarbonyl-(L)-tert-leucine and 300 mg (1 mmol) of TPTU in 3 ml of DMF.

M.p.: 118–121° C. (decomp.). TLC: $R_f$=0.40 (ethyl acetate). FAB MS (M+H)$^+$=683.

The Starting Material is Prepared as Follows:

11a) 1-[p-(Pyrrolidin-1-yl)phenyl]-4(S)-hydroxy-2-(tert-butyloxycarbonyl)amino-5(S)-[N-(N-methoxycarbonyl-(L)-valyl)amino]-6-phenyl-2-azahexane In analogy with Example 8e, the title compound is obtained, after working-up, from 4 g (8.8 mmol) of 1-[p-(pyrrolidin-1-yl)phenyl]-4(S)-hydroxy-2-(tert-butyloxycarbonyl)amino-5(S)-amino-6-phenyl-2-azahexane (Example 8d), 3 g (17.6 mmol) of N-methoxycarbonyl-(L)-valine, 6.7 g (35.2 mmol) of EDC, 4.8 g (35.2 mmol) of HOBT and 12.3 ml (88 mmol) of triethylamine in 90 ml of DMF; it is then obtained in crystalline form from ethyl acetate/ether.

TLC: $R_f$=0.55 (ethyl acetate). HPLC$_{20-100}$: $t_{ret}$=12.90.

11 b) 1-[p-(Pyrrolidin-1-yl)phenyl]-4(S)-hydroxy-2-amino-5(S)-[N-(N-methoxycarbonyl-(L)-valyl)-amino]-6-phenyl-2-azahexane 612 mg (1 mmol) of 1-[p-(pyrrolidin-1-yl)phenyl]-4(S)-hydroxy-2-(tert-butyloxycarbonyl)-amino-5(S)-[N-(N-methoxycarbonyl-(L)-valyl)amino]-6-phenyl-2-azahexane (Example 11a) in 15 ml of methylene chloride are cooled in an ice bath, after which 15 ml of trifluoroacetic acid are added. The mixture is allowed to warm to RT and is stirred for a further 2 h. The solvent is removed while excluding moisture. The residue is taken up in methylene chloride and this solution is washed with sat. sodium bicarbonate solution/water 1:1. After separating the phases, the washing procedure with sodium bicarbonate solution and water is repeated. The organic phase is concentrated by evaporation and the title compound is obtained as a pale brown foam which is subjected to further processing without being purified.

HPLC$_{20-100}$: $t_{ret}$=10.88. TLC: $R_f$=0.71 (methylene chloride/methanol/sat. ammonia 300:50:1).

EXAMPLE 12

1-[p-(Pyrrolidin-1-yl)phenyl]-4(S)-hydroxy-5(S)-2,5bis[N-(N-methoxycarbonyl-(L)-isoleucyl)amino]-6-phenyl-2-azahexane In analogy with Example 8, the title compound is obtained, after working-up, from 900 mg (1.5 mmol) of 1-[p-(pyrrolidin-1-yl)phenyl]-4(S)-hydroxy-2-amino-5(S)-[N-(N-methoxycarbonyl-(L)-isoleucyl)amino]-6-phenyl-2-azahexane hydrochloride (Example 12b) and 1.1 ml (8 mmol) of triethylamine in 6 ml of DMF (solution A) and also 380 mg (1 mmol) of N-methoxycarbonyl-(L)-isoleucine and 600 mg (1 mmol) of TPTU in 5 ml of DMF (solution B).

M.p.: 200–203° C. TLC: $R_f$=0.47 (ethyl acetate). FAB MS (M+H)$^+$=697.

The Starting Material is Prepared as Follows:

12a) 1-[p-(Pyrrolidin-1-yl)phenyl]-4(S)-hydroxy-2-(tert-butyloxycarbonyl)amino-5(S)-[N-(N-methoxycarbonyl-(L)-isoleucyl)amino]-6-phenyl-2-azahexane In analogy with Example 8e, the title compound is obtained, after working-up, from 4 g (8.8 mmol) of 1-[p-

(pyrrolidin-1-yl)phenyl]-4(S)-hydroxy-2-(tert-butyloxycarbonyl)amino-5(S)-amino-6-phenyl-2-azahexane (Example 8d), 3.3 g (17.6 mmol) of N-methoxycarbonyl-(L)-isoleucine, 6.7 g (35.2 mmol) of EDC, 4.8 g (35.2 mmol) of HOBT and 12.3 ml (88 mmol) of triethylamine in 90 ml of DMF; it is then obtained in crystalline form from ethyl acetate/ether/petroleum ether.

TLC: $R_f$=0.58 (ethyl acetate). $HPLC_{20-100}$: $t_{ret}$=13.58.

12b) 1-[p-(Pyrrolidin-1-yl)phenyl]-4(S)-hydroxy-2-amino-5(S)-[N-(N-methoxycarbonyl-(L)-isoleucyl)amino]-6-phenyl-2-azahexane Hydrochloride In analogy with Example 8f, the title compound, which is subjected to further processing without being purified, is obtained, as a pale pink powder, from 2.3 g (3.7 mmol) of 1-[p-(pyrrolidin-1-yl)phenyl]-4(S)-hydroxy-2-(tert-butyloxycarbonyl)amino-5(S)-[N-(N-methoxycarbonyl-(L)-isoleucyl)amino]-6-phenyl-2-azahexane (Example 12a) in a mixture consisting of 60 ml of 4N hydrochloric acid in dioxane and 10 ml of methanol after stirring at RT for 2.5 h.

EXAMPLE 13

1-[p-(Pyrrolidin-1-yl)phenyl]-4(S)-hydroxy-2-[N-(N-methoxycarbonyl-(L)-valyl)amino]-5(S)-[N-(N-methoxycarbonyl-(L)-isoleucyl)amino]-6-phenyl-2-azahexane In analogy with Example 8, the title compound is obtained, after working-up, from 600 mg (1.5 mmol) of 1-[p-(pyrrolidin-1-yl)phenyl]-4(S)-hydroxy-2-amino-5(S)-[N-(N-methoxycarbonyl-(L)-isoleucyl)amino]-6-phenyl-2-azahexane hydrochloride (Example 12b) and 0.56 ml (5 mmol) of triethylamine in 4 ml of DMF (solution A) and also 175 mg (1 mmol) of N-methoxycarbonyl-(L)-valine and 300 mg (1 mmol) of TPTU in 3 ml of DMF (solution B). It is then lyophilized from dioxane.

TLC: $R_f$=0.39 (ethyl acetate). FAB MS $(M+H)^+$=683.

EXAMPLE 14

1-[p-(1,2,4-Triazol-4-yl)phenyl]-4(S)-hydroxy-2-[N-(N-methoxycarbonyl-(L)-isoleucyl)amino]-5(S)-[N-(N-methoxycarbonyl-(L)-valyl)amino]-6-phenyl-2-azahexane In analogy with Example 8e, the title compound is obtained, after working-up, from 200 mg (0.39 mmol) of 1-[p-(1,2,4-triazol-4-yl)phenyl]-4(S)-hydroxy-2-amino-5(S)-[N-(N-methoxycarbonyl-(L)-valyl)amino]-6-phenyl-2-azahexane (Example 14g), 238 mg (1.26 mmol) of N-methoxycarbonyl-(L)-isoleucine, 450 mg (2.35 mmol) of EDC, 318 mg (2.35 mmol) of HOBT and 0.876 ml (6.28 mmol) of triethylamine in 10 ml of DMF (with a further one half of the abovementioned quantities of the reagents and starting compounds being added after the reaction has been in progress for 4 h). The substance is precipitated from methylene chloride with DIPE and lyophilized from dioxane.

$HPLC_{20-100}$: $t_{ret}$=11.47. FAB MS $(M+H)^+$=681.

The Starting Material is Prepared as Follows:

14a p-(1,2,4-Triazol-1-yl)benzaldehyde and p-(1,2,4-Triazol-4-yl)benzaldehyde 21 ml (200 mmol) of 4-fluorobenzaldehyde (Fluka, Buchs, Switzerland), 30.48 g (220 mmol) of potassium carbonate and 13.8 g (200 mmol) of 1,2,4-triazole (Fluka, Buchs, Switzerland) are suspended in 100 ml of pyridine, after which 1.2 g of copper(I) oxide are added. The reaction mixture is boiled at reflux for 16 h. After that, the solvent is removed and the residue is taken up twice in toluene, followed by evaporation, and dissolved in methylene chloride. The insoluble material is removed by filtration and the solution is concentrated. This yields a mixture of the two 1,2,4-triazol-1-yl- and 1,2,4-triazol-4-yl-substituted benzaldehyde, which can be separated, after digesting with hexane, by means of chromatography on silica gel (mobile solvent: hexane/ethyl acetate 1:1, ethyl acetate and methylene chloride/5% methanol).

p-(1,2,4-Triazol-1-yl)benzaldehyde: $HPLC_{20-100}$: $t_{ret}$=8.50. $^1H$ NMR (DMSO-$D_6$; 200 MHz): 10.04/s (1H); 9.47/s (1H); 8.31/s (1H); 8.12 and 8.09/in each case d, J=10 (2×2H). p-(1,2,4-Triazol-4-yl)benzaldehyde: $HPLC_{20-100}$: $t_{ret}$=5.96. $^1H$ NMR (DMSO-$D_6$; 200 MHz): 10.05/s (1H); 9.27/s (1H); 8.31/s (1H); 8.09 and 7.98/in each case d, J=9 (2×2H).

14b) N-1-(tert-Butyloxycarbonyl)-N-2-{p-[(1,2,4-triazol-4-yl)phenyl]-methylidene}hydrazone A solution of 2.88 g (16.6 mmol) of p-(1,2,4-triazol-4-yl)benzaldehyde (Example 14a) and 2 g (15.1 mmol) of tert-butyl carbazate (Fluka, Buchs, Switzerland) in 50 ml of ethanol is stirred at 80° C. overnight. The reaction mixture is concentrated down to approximately half its volume, and 50 ml of water are then added. This results in the formation of a crystalline precipitate, which is filtered off. For purification, the precipitate is dissolved in isopropanol and the title compound is precipitated once again with water.

$HPLC_{20-100}$: $t_{ret}$=9.60. $^1H$ NMR ($CD_3OD$; 200 MHz): 9.05/s (2H); 7.97/s (1H); 7.91 and 7.67/in each case d (2×2H); 1.55/s (9H).

14c) N-1-(tert-Butyloxycarbonyl)-N-2-[p-(1,2,4-triazol-4-yl)benzyl]hydrazine 2.38 g (8.28 mmol) of N-1-(tert-butyloxycarbonyl)-N-2-{p-[(1,2,4-triazol-4-yl)phenyl]-methylidene}hydrazone (Example 14b) and 0.5 g of 5% Pd/C in 50 ml of methanol are hydrogenated at RT for 14 h under standard pressure. The catalyst is filtered off and the solvent removed. The title compound is obtained as a yellow oil, which can be subjected to further use without being purified.

$HPLC_{20-100}$: $t_{ret}$=7.00. $^1H$ NMR ($CD_3OD$; 200 MHz): 8.97/s (2H); 7.60/s (4H); 4.00/s (2H); 1.44/s (9H).

14d) 1-[p-(1,2,4-Triazol-4-yl)phenyl]-4(S)-hydroxy-2-(tert-butyloxycarbonyl)amino-5(S)-(trifluoroacetyl)amino-6-phenyl-2-azahexane 2.09 g (8.05 mmol) of (2R)-[(1'S)-(trifluoroacetyl)amino-2'-phenylethyl]oxirane and 2.33 g (8.05 mmol) of N-1-(tert-butyloxycarbonyl)-N-2-[p-(1,2,4-triazol-4-yl)benzyl]hydrazine (Example 14c) in 50 ml of isopropanol are heated at reflux overnight. The solvent is then removed and the residue is dried in vacuo and chromatographed on silica gel (methylene chloride/methanol 19:1). The title compound is obtained as a yellow solid. $HPLC_{20-100}$: $t_{ret}$=13.39.

14e) 1-[p-(1,2,4-Triazol-4-yl)phenyl]-4(S)-hydroxy-2-(tert-butyloxycarbonyl)amino-5(S)-amino-6-phenyl-2-azahexane 0.756 g (1.38 mmol) of 1-[p-(1,2,4-triazol-4-yl)phenyl]-4(S)-hydroxy-2-(tert-butyloxycarbonyl)amino-5(S)-(trifluoroacetyl)amino-6-phenyl-2-azahexane (Example 14d) is initially introduced in 28 ml of methanol, and 6.9 ml (6.89 mmol) of a 1 M aqueous solution of potassium carbonate are then added. The reaction mixture is stirred under reflux for 3 h and then concentrated down to about 10 ml; it is then acidified with dilute hydrochloric acid and extracted with methylene chloride. The title compound crystallizes out on concentrating. $HPLC_{20-100}$: $t_{ret}$=8.97. $^1$H NMR (CD$_3$OD; 200 MHz) i.a.: 8.98/s (2H); 7.75–7.6/m (4H); 7.5–7.1/m (5H); 3.96/bs (2H); 1.32/s (9H).

14f) 1-[p-(1,2,4-Triazol-4-yl)phenyl]-4(S)-hydroxy-2-(tert-butyloxycarbonyl)amino-5(S)[N-(N-methoxycarbonyl-(L)-valyl)amino]-6-phenyl-2-azahexane In analogy with Example 8e, the title compound is obtained from 0.547 g (1.18 mmol) of 1-[p-(1,2,4-triazol-4-yl)phenyl]-4(S)-hydroxy-2-(tert-butyloxycarbonyl)amino-5(S)-amino-6-phenyl-2-azahexane (Example 14e), 0.413 g (2.35 mmol) of N-methoxycarbonyl-(L)-valine, 0.903 g (4.71 mmol) of EDC, 0.636 g (4.71 mmol) of HOBT and 1.64 ml (11.8 mmol) of triethylamine in 20 ml of DMF, and is then precipitated from methanol/DIPE/hexane. $HPLC_{20-100}$: $t_{ret}$=12.45. $^1$H NMR (CD$_3$OD; 200 MHz) i.a.: 8.98/s (2H); 7.75–7.5/m (4H); 7.36–7.04/m (5H); 1.31/s (9H); 0.81/d, J=7.5 (6H).

14 g) 1-[p-(1,2,4-Triazol-4-yl) phenyl]-4(S)-hydroxy-2-amino-5(S)-[N-(N-methoxycarbonyl-(L)-valyl)amino]-6-phenyl-2-azahexane 0.543 g (0.89 mmol) of 1-[p-(1,2,4-triazol-4-yl)phenyl]-4(S)-hydroxy-2-(tert-butyloxycarbonyl)amino-5(S)-[N-(N-methoxycarbonyl-(L)-valyl)amino]-6-phenyl-2-azahexane (Example 14f) is stirred in 20 ml of formic acid at RT for 4 h under nitrogen. The formic acid is removed, the residue is taken up in methylene chloride, and the organic phase is washed with a sat. solution of sodium bicarbonate. The title compound is isolated as a yellow foam, which is subjected to further processing without being purified.

$HPLC_{20-100}$: $t_{ret}$=8.12.

EXAMPLE 15

1-[p-(1,2,4-Triazol-1-yl)phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane In analogy with Example 8e, the title compound is obtained, after working-up, from 300 mg (0.589 mmol) of 1-[p-(1,2,4-triazol-1-yl)phenyl]-4(S)-hydroxy-2-amino-5(S)-N-(N-methoxycarbonyl-(L)-valyl)amino]-6-phenyl-2-azahexane (Example 15f), 334 mg (1.76 mmol) of N-methoxycarbonyl-(L)-tert-leucine, 790 mg (4.12 mmol) of EDC, 556 mg (4.12 mmol) of HOBT and 1.15 ml (8.24 mmol) of triethylamine in 20 ml of DMF. The substance is precipitated from methylene chloride with DIPE. Additional purification is by chromatography on silica gel (hexane/acetone 1:1).

$HPLC_{20-100}$: $t_{ret}$=12.77. FAB MS (M+H)$^+$=681.

The Starting Material is Prepared as Follows:

15a) N-1-(tert-Butyloxycarbonyl)-N-2-{p-[(1,2,4-triazol-1-yl)phenyl]-methylidene}hydrazone In analogy with Example 14b, the title compound is obtained, as colorless crystals, from 2.88 g (16.6 mmol) of p-(1,2,4-triazol-1-yl)benzaldehyde (Example 14a) and 2 g (15.1 mmol) of tert-butyl carbazate (Fluka, Buchs, Switzerland) in 50 ml of ethanol.

$HPLC_{20-100}$: $t_{ret}$=11.66. $^1$H NMR (CD$_3$OD; 200 MHz): 9.15/s (1H); 8.18/s (1H); 7.97/a (1H); 7.88/s (4H); 1.56/s (9H).

15b) N-1-(tert-Butyloxycarbonyl)-N-2-[p-(1,2,4-triazol-1-yl)benzy]hydrazine

In analogy with Example 14c, the title compound is obtained, as colorless crystals, from 4 g (13.96 mmol) of N-1-(tert-butyloxycarbonyl)-N-2-{p-[(1,2,4-triazol-1-yl)phenyl]methylidene}hydrazone (Example 15a) and 0.5 g of 5% Pd/C in 60 ml of methanol. The hydrogenation is carried out for approximately 5 h.

$HPLC_{20-100}$: $t_{ret}$=8.39. $^1$H NMR (CD$_3$OD; 200 MHz): 9.08/s (1H); 8.17/s (1H); 7.78 and 7.55/in each case d, J=9 (2×2H); 4.0/s (2H); 1.44/s (9H).

15c) 1-[p-(1,2,4-Triazol-1-yl)phenyl]-4(S)-hydroxy-2-(tert-butyloxycarbonyl)amino-5(S)-(trifluoroacetyl)amino-6-phenyl-2-azahexane In analogy with Example 14d, the title compound is obtained from 2.99 g (11.5 mmol) of (2R)-[(1'S)-(trifluoroacetyl)amino-2'-phenylethyl]oxirane and 3.34 g (11.5 mmol) of N-1-(tert-butyloxycarbonyl)-N-2-[p-(1,2,4-triazol-1-yl)benzyl]hydrazine (Example 15b) in 50 ml of isopropanol.

$HPLC_{20-100}$: $t_{ret}$=14.98.

15d) 1-[p-(1,2,4-Triazol-1-yl)phenyl]-4(S)-hydroxy-2-(tert-butyloxycarbonyl)amino-5(S)-amino-6-phenyl-2-azahexane In analogy with Example 14e, the title compound, which is subjected to further processing without being purified, is obtained from 5.29 g (9.64 mmol) of 1-[p-(1,2,4-triazol-1-yl)-phenyl]-4(S)-hydroxy-2-(tert-butyloxycarbonyl)amino-5(S)-(trifluoroacetyl)amino-6-phenyl-2-azahexane (Example 15c) and 48.2 ml of a 1 M aqueous solution of potassium carbonate in 200 ml of methanol.

$HPLC_{20-100}$: $t_{ret}$=10.20.

15e) 1-[p-(1,2,4-Triazol-1-yl)phenyl]-4(S)-hydroxy-2-(tert-butyloxycarbonyl)amino-5(S)-[N-(N-methoxycarbonyl-(L)-valyl)amino]-6-phenyl-2-azahexane In analogy with Example 8e, the title compound is obtained from 2 g (4.42 mmol) of 1-[p-(1,2,4-triazol-1-yl)phenyl]-4(S)-hydroxy-2-(tert-butyloxycarbonyl)amino-5 (S)-amino-6-phenyl-2-azahexane (Example 15d), 1.24 g (7.07 mmol) of N-methoxycarbonyl-(L)-valine, 2.54 g (13.26 mmol) of EDC, 1.19 g (8.84 mmol) of HOBT and 3.69 ml (26.5 mmol) of triethylamine in 60 ml of DMF; for purification, it is then chromatographed on silica gel (methylene chloride/methanol 30:1).

$HPLC_{20-100}$: $t_{ret}$=13.92. FAB MS (M+H)$^+$=610.

15f) 1-[p-(1,2,4-Triazol-1-yl)phenyl]-4(S)-hydroxy-2-amino-5(S)-[N-(N-methoxycarbonyl-(L)-valyl)amino]-6-phenyl-2-azahexane In analogy with Example 14g, the title compound, which is subjected to further processing without being purified, is obtained from 0.84 g (1.37 mmol) of 1-[p-(1,2,4-triazol-1-yl)-phenyl]-4(S)-hydroxy-2-(tert-butyloxycarbonyl)amino- 5(S)-N-(N-methoxycarbonyl-(L)-valyl)amino-6-phenyl-2-azahexane (Example 15e) in 20 ml of formic acid.

HPLC$_{20-100}$: t$_{ret}$=8.96.

EXAMPLE 16

1-[p-(4-Methylpiperazin-1-yl)phenyl]-4(S)-hydroxy-5(S)-2,5-bis[N-(N-methoxycarbonyl-(L)-valyl)amino]-6-phenyl-2-azahexane While excluding moisture, 119 mg (0.68 mmol) of N-methoxycarbonyl-(L)-valine, 244 mg (1.28 mmol) of EDC and 115 mg (0.85 mmol) of HOBT are initially introduced in 5.4 ml of DMF. After 20 min at RT, 0.355 ml (2.55 mmol) of triethylamine is added. 232 mg (0.425 mmol) of 1-[p-(4-methylpiperazin-1-yl)phenyl]-4(S)-hydroxy-2-amino-5(S)-[N-(N-methoxycarbonyl-(L)-valyl)amino]-6-phenyl-2-azahexane are then added and the mixture is thoroughly stirred overnight. The reaction mixture is evaporated under HV; the residue is dissolved in methylene chloride and this solution is washed with sat. NaHCO$_3$ solution, water and brine. The aqueous phases are extracted twice with methylene chloride. The combined organic phases are dried (Na$_2$SO$_4$) and concentrated by evaporation. Precipitating with DIPE from a concentrated solution in methanol gives the title compound:

HPLC$_{20-100}$(12'): t$_{ret}$=7.9; FAB MS (M+H)$^+$=698.

The Starting Material is Prepared as Follows:

16a) p-(4-Methylpiperazin-1-yl)benzaldehyde 20 ml (0.18 mol) of 1-methylpiperazine and 19 ml (0.18 mol) of 4-fluorobenzaldehyde (Fluka, Buchs, Switzerland), in each case in 45 ml of DMSO, are added to 25 g (0.18 mol) of K$_2$CO$_3$ in 90 ml of DMSO and the whole is stirred at 100° C. for 3 h. The reaction mixture is cooled down and poured onto 2l of ice water; this mixture is then extracted twice with ethyl acetate. The organic phases are washed with brine, dried (Na$_2$SO$_4$) and concentrated by evaporation, with the title compound thereby being obtained:

$^1$H NMR (CDCl$_3$) d 9.78 (s, HCO), 7.74 and 6.91 (2d, J=8, 2×2H), 3.42 and 2.55 (2t, J=5, 2×4H), 2.33 (s, Me).

16b) N-1-(tert-Butyloxycarbonyl)-N-2-{[p-(4-methylpiperazin-1-yl)phenyl]-methylidene}hydrazone A solution of 30.1 g (147 mmol) of p-(4-methylpiperazin-1-yl)benzaldehyde and 20.4 g (154 mmol) of tert-butyl carbazate in 910 ml of ethanol is stirred at 80° C. for 15 h. Cooling down, evaporating down to approximately 0.5 l, and crystallizing by adding 1 l of water, yields the title compound:

$^1$H NMR (CDCl$_3$) d 7.72 (sb, HC=N), 7.57 and 6.87 (2d, J=9, 2×2H), 3.28 and 2.55 (2t, J=5, 2×4H), 2.34 (s, Me), 1.53 (s, Me$_3$C).

16c) N-1-(tert-Butyloxycarbonyl)-N-2-[p-(4-methylpiperazin-1-yl)benzyl]hydrazine 22.2 g (69.7 mmol) of N-1-(tert-butyloxycarbonyl)-N-2-{[p-(4-methylpiperazin-1-yl)phenyl]-methylidene}hydrazone in 400 ml of methanol are hydrogenated in the presence of 2 g of 5% Pd/C. The catalyst is filtered off through Hyflo and the filtrate is concentrated by evaporation. Dissolving the residue in 100 ml of hot ethyl acetate, adding 240 ml of hexane, cooling and filtering off yields the crystalline title compound:

Anal. (C$_{17}$H$_{28}$ N$_4$O$_2$) calc. C, 63.72, H, 8.81, N, 17.48: fnd. C, 63.60, H, 8.55, N, 17.54.

16d) 1-[p-(4-Methylpiperazin-1-yl)phenyl]-4(S)-hydroxy-2-(tert-butyloxycarbonyl)amino-5(S)-(trifluoroacetyl)amino-6-phenyl-2-azahexane 16.6 g (63.9 mmol) of (2R)-[(1'S)-(trifluoroacetyl)amino-2'-phenylethyl]oxirane and 20.5 g (63.9 mmol) of N-1-(tert-butyloxycarbonyl)-N-2-[p-(4-methylpiperazin-1-yl)benzyl]hydrazine in 205 ml of isopropanol are heated at 80° C. for 36 h. Cooling of the reaction mixture, evaporation and column chromatography (SiO$_2$, methylene chloride/methanol 20:1) results in the title compound:

TLC: R$_f$=0.43 (methylene chloride/methanol 8.1); FAB MS (M+H)$^+$=580.

16e) 1-[p-(4- Methylpiperazin-1-yl)phenyl]-4(S)-hydroxy-2-(tert-butyloxycarbonyl)amino-5(S)-amino-6-phenyl-2-azahexane 100 ml of a 1N solution of K$_2$CO$_3$ are added dropwise to a solution of 5.8 g (10.0 mmol) of 1-[p-(4-methylpiperazin-1-yl)phenyl]-4(S)-hydroxy-2-(tert-butyloxycarbonyl)amino-5(S)-(trifluoroacetyl)amino-6-phenyl-2-azahexane in 100 ml of methanol and the whole is heated to boiling for 15 h. The mixture is partially concentrated by evaporation, after which methylene chloride and water are added; the water phase is separated off and extracted twice with methylene chloride, after which the organic phases are washed twice with water and brine, dried (Na$_2$SO$_4$) and concentrated by evaporation. Stirring the residue in hexane yields the title compound:

HPLC$_{20-100}$: t$_{ret}$=8.4.

16f) 1-[p-(4-Methylpiperazin-1-yl)phenyl]-4(S)-hydroxy-2-(tert-butyloxycarbonyl)amino-5(S)-[N-(N-methoxycarbonyl-(L)-valyl)amino]-6-phenyl-2-azahexane 1.60 g (9.16 mmol) of N-methoxycarbonyl-(L)-valine, 3.29 g (17.16 mmol) of EDC and 1.54 g (11.4 mmol) of HOBT are dissolved, under a N$_2$ atmosphere, in 49 ml of DMF. After 20 min at RT, 4.8 ml (34.4 mmol) of triethylamine are added. 2.77 g (5.7 mmol) of 1-[p-(4-methylpiperazin-1-yl)phenyl]-4(S)-hydroxy-2-(tert-butyloxycarbonyl)amino-5(S)-amino-6-phenyl-2-azahexane in 24 ml of DMF are then added and the whole is thoroughly stirred overnight. The reaction mixture is evaporated under HV and the residue is dissolved in methylene chloride and a little methanol; this solution is then washed with sat. NaHCO$_3$ solution, water and brine. The aqueous phases are extracted twice with methylene chloride. The combined organic phases are dried (Na$_2$SO$_4$) and concentrated by evaporation. Precipitating with DIPE from a concentrated solution in boiling methylene chloride results in the title compound:

Anal. (C$_{34}$H$_{52}$ N$_6$O$_6$ (0.38 H$_2$O)) calc. C, 63.05, H, 8.21, N, 12.98, H$_2$O 1.06: fnd. C, 62.83, H, 8.21, N, 12.76, H$_2$O 1.06.

16g) 1-[p-(4-Methylpipperazin-1-yl)phenyl]-4(S)-hydroxy-2-amino-5(S)-[N-(N-methoxycarbonyl-(L)-valyl)amino]-6-phenyl-2-azahexane While excluding moisture, 600 mg (0.936 mmol) of 1-[p-(4-methylpiperazin-1-yl)phenyl]-4(S)-hydroxy-2-(tert-butyloxycarbonyl)amino-5(S)-[N-(N-methoxycarbonyl-(L)-valyl)amino]-6-phenyl-2-azahexane are dissolved in 40 ml of methylene chloride at 0° C., and 20 ml of trifluoroacetic acid are then added. After 15 h at 0° C., the mixture is evaporated under mild conditions and the residue is taken up in methylene chloride and sat. NaHCO$_3$ solution. The aqueous phase is separated off and extracted twice with methylene chloride. Washing the organic phases with sat. NaHCO$_3$ solution and brine, drying them (Na$_2$SO$_4$) and concentrating them by evaporation, results in the title compound:

HPLC$_{20-100}$: t$_{ret}$=6.5.

EXAMPLE 17

1-[p-(4-Methylpiperazin-1-yl)phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane 129 mg (0.68 mmol) of N-methoxycarbonyl-(L)-tert-leucine, 244 mg (1.28 mmol) of EDC and 115 mg (0.85 mmol) of HOBT are initially introduced, under a N$_2$ atmosphere, in 5.4 ml of DMF. After 20 min at RT, 0.355 ml (2.55 mmol) of triethylamine is added. 232 mg (0.425 mmol) of 1-[p-(4-methylpiperazin-1-yl)phenyl]-4(S)-hydroxy-2-amino-5(S)-[N-(N-methoxycarbonyl-(L)-valyl)amino]-6-phenyl-2-azahexane (Example 16g) are then added and the mixture is thoroughly stirred overnight; working-up then takes place in analogy with Example 16. Column chromatography (SiO$_2$; ethyl acetate/ethanol 1:1) results in the title compound:

TLC: R$_f$=0.24 (ethyl acetate/ethanol 1:1); HPLC$_{20-100(12')}$: t$_{ret}$=8.2; FAB MS (M+H)$^+$=712.

EXAMPLE 18

1-[p-(4-Methylpiperazin-1-yl)phenyl]-4(S)-hydroxy-2-[N-(N-methoxycarbonyl-(L)-isoleucyl)amino-5(S)-[N-(N-methoxcycarbonyl-(L)-valyl)amino]-6-phenyl-2-azahexane 129 mg (0.68 mmol) of N-methoxycarbonyl-(L)-isoleucine, 244 mg (1.28 mmol) of EDC and 115 mg (0.85 mmol) of HOBT are initially introduced, under a N$_2$ atmosphere, in 5.4 ml of DMF. After 20 min at RT, 0.355 ml (2.55 mmol) of triethylamine is added. 232 mg (0.425 mmol) of 1-[p-(4-methylpiperazin-1-yl)phenyl]-4(S)-hydroxy-2-amino-5(S)-[N-(N-methoxycarbonyl-(L)-valyl)amino]-6-phenyl-2-azahexane are then added and the mixture is thoroughly stirred overnight and worked up in analogy with Example 16. Crystallizing with DIPE from a boiling solution in ethanol results in the title compound:

HPLC$_{20-100(12')}$: t$_{ret}$=8.2; FAB MS (M+H)$^+$=712.

EXAMPLE 19

Gelatin Solution

An aqueous solution, which has been sterilized by filtration and which contains 20% cyclodextrins as solubilizers, of one of the compounds of the formula I mentioned in the preceding examples (e.g. the title compound from Example 2), as active compound, is mixed under aseptic conditions, while heating, with a sterile gelatin solution, which contains phenol as preservative, such that 1.0 ml of solution has the following composition:

| | |
|---|---|
| Active compound | 3 mg |
| Gelatin | 150 mg |
| Phenol | 4.7 mg |
| dist. water containing 20% cyclodextrins as solubilizers | 1.0 ml |

EXAMPLE 20

Sterile Dry Substance for Injection 5 mg of one of the compounds of the formula I mentioned in the preceding examples (for example the title compound from Example 1), as active compound, are dissolved in 1 ml of an aqueous solution containing 20 mg of mannitol and 20% cyclodextrins as solubilizers. The solution is sterilized by filtration and aliquotted, under aseptic conditions, into 2 ml ampoules, after which it is deep-frozen and lyophilized. Prior to use, the lyophilisate is dissolved in 1 ml of distilled water or 1 ml of physiological sodium chloride solution. The solution is used intramuscularly or intravenously. This formulation can also be aliquotted into double-chamber cartridge disposable syringes.

EXAMPLE 21

Nasal Spray 500 mg of finely ground (<5.0 μm) powder of one of the compounds of the formula I mentioned in the preceding examples (for example the compound from Example 4) are suspended, as active compound, in a mixture of 3.5 ml of Myglyol 812® and 0.08 g of benzyl alcohol. This suspension is aliquotted into a container possessing a metering valve. 5.0 g of Freon 12® (dichlorodifluoromethane; trade mark of DuPont) are aliquotted, under pressure, through the valve into the container. The "Freon" is dissolved in the Myglyol/benzyl alcohol mixture by shaking. This spray container comprises approx. 100 single doses, which can be administered individually.

EXAMPLE 22

Lacquered Tablets

In order to prepare 10,000 tablets each comprising 100 mg of active compound, the following constituents are processed:

| | |
|---|---|
| Active compound | 1000 g |
| Corn starch | 680 g |
| Colloidal silicic acid | 200 g |
| Magnesium stearate | 20 g |
| Stearic acid | 50 g |
| Sodium carboxymethyl starch | 250 g |
| Water | quantum satis |

A mixture of one of the compounds of the formula I mentioned in the preceding examples (for example the compound from Example 3), as active compound, 50 g of corn starch and the colloidal silicic acid is worked into a moist mass together with starch paste consisting of 250 g of corn starch and 2.2 kg of demineralized water. This mass is impelled through a sieve of 3 mm mesh width and dried at 45° for 30 min in a fluidized bed dryer. The dried granules are pressed through a sieve of 1 mm mesh width, mixed with a previously sieved mixture (1 mm sieve) of 330 g of corn starch, the magnesium stearate, the stearic acid and the sodium carboxymethyl starch, and compressed into slightly convex tablets.

EXAMPLE 23

Capsules (I)

A compound from one of the abovementioned examples (e.g. the title compound from Example 5) is micronized (particle size approx. from 1 to 100 μm) using a customary blade mixer (e.g. Turmix). ®Pluronic F 68 (block copolymer consisting of polyethylene and polypropylene glycol; Wyandotte Chem. Corp., Michigan, USA; can also be obtained from Emkalyx, France; trade mark of BASF))) is likewise micronized using a customary mixer and the fines are sieved out with a sieve (0.5 mm) and then subsequently used as described below. 16.00 g of sesame oil are initially introduced into a beaker, and 1.20 g of the micronized active substance, 1.20 g of the ®Pluronic F 68 fines and 1.20 g of hydroxypropyl methyl cellulose (HP-M-603 cellulose from Shin-Etsu Chemicals Ltd., Tokyo, Japan) are added while stirring with a stirrer (IKA-Werk, FRG) which is combined with a toothed stirrer (diameter: 46 mm) (stirring speed: 2000 rpm). 20 min of stirring at the given stirring speed produces a suspension of paste-like consistency which is aliquotted into hard gaelatin capsules (20×40 mm; R. P. Scherer AG, Eberbach, FRG).

EXAMPLE 24

Capsules (II)

In order to prepare 10,000 capsules comprising 100 mg of active compound (from one of the abovementioned examples, e.g. the title compound from Example 2) per capsule the constituents listed below are processed as follows:

| | |
|---|---|
| Active compound | 1000 g |
| ®Pluronic F 68 | 1000 g |
| Hydroxypropyl methyl cellulose | 1000 g |
| Sesame oil | 1000 g |
| (origin of the constituents: cf. Example 23) | |

The sesame oil is initially introduced into a heatable vat (Fryma) and the ®Pluronic F 68 is then sprinkled in. The vat is heated to 60° C. and the ®Pluronic F 68 is dispersed while stirring (time approx. 2 h). While stirring and homogenizing, the mixture is cooled down to approx. 30° C. The hydroxypropyl methyl cellulose and the active compound are sprinkled in and dispersed in the oily mass while stirring and homogenizing (approx. 1 h). The suspension, which is of a paste-like consistency, is aliquotted into hard gelatin capsules (size 0; obtainable, for example, from Elanco or Parke-Davies (Caprogel)) or soft gelatin capsules (20 mm oblong; R. P. Scherer A G, Eberbach, FRG) using the customary equipment.

EXAMPLE 25

Dispersion

In order to prepare a dispersion comprising 120.0 mg of active compound/10 ml (preferably the title compound from Example 2), the constituents listed below are processed as follows:

| | |
|---|---|
| Active compound | 120.0 mg |
| ® Klucel HF (hydroxypropyl cellulose; Hercules, Germany)) | 50.0 mg |
| ® Tween 20 (polyoxyethylene sorbitan monolaurate; Fluka, Buchs, Switzerland) | 100.00 mg |
| Demineralized water | 10.0 ml |

The demineralized water is initially introduced, and the hydroxypropyl cellulose is then sprinkled in slowly while stirring with a magnetic stirrer and the whole is left to swell for 1 h. The polyoxyethylene sorbitan monolaurate is then added and the mixture is stirred with the magnetic stirrer for 5 min. The active substance is then finally added and the mixture is stirred with the magnetic stirrer for 15 min.

---

What is claimed is:

1. A compound of the formula I,

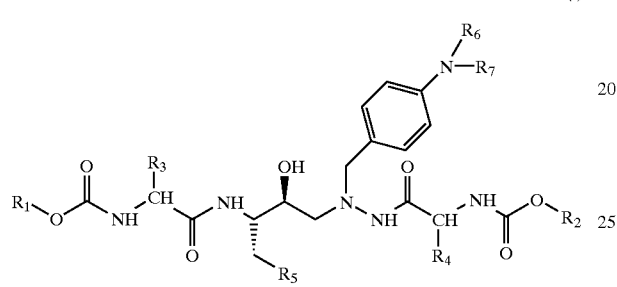

(I)

in which $R_1$ and $R_2$ are, independently of each other, lower alkyl or lower alkoxy-lower alky;

$R_3$ and $R_4$ are, independently of each other, sec-lower alkyl or tert-lower alkyl;

$R_5$ is phenyl or cyclohexyl; and $R_6$ and $R_7$ are, independently of each other, lower alkyl, or, together with the linking nitrogen atom, pyrrolidino, piperidino, 4-lower alkylpiperidino, 1,2,4-triazol-1-yl or 1,24-triazol-4-yl;

or a salt thereof, provided that at least one salt-forming group is present wherein the compound of formula I possesses HIV protease inhibitory activity.

2. A compound of the formula I according to claim 1, in which $R_1$ and $R_2$ are in each case, independently of each other, lower alkyl;

$R_3$ and $R_4$ are, independently of each other, sec- or tert-lower alkyl;

$R_5$ is phenyl; and $R_6$ and $R_7$ are, independently of each other, lower alkyl, or, together with the linking nitrogen atom, are pyrrolidino;

or a salt thereof, provided at least one salt-forming group is present.

3. A compound of the formula I according to claim 1, in which $R_1$ and $R_2$ are in each case methyl;

$R_3$ is isopropyl or tert-butyl;

$R_4$ is tert-butyl; and $R_5$ is phenyl; and $R_6$ are in each case lower alkyl, or a salt thereof, provided a salt-forming group is present.

4. A compound according to claim 1 of the formula Ia,

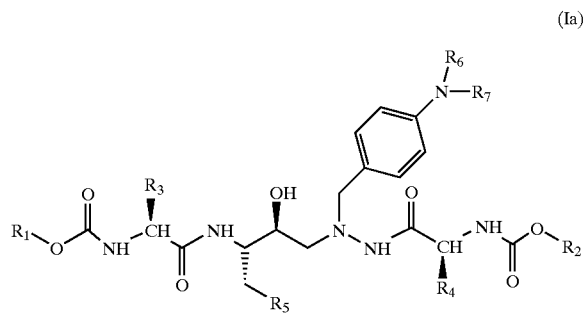

(Ia)

in which the radicals $R_1$ to $R_7$ are as defined in claim 1, or a salt thereof, provided at least one salt-forming group is present.

5. A composition comprising a carrier or diluent and a compound of the formula I according to claim 1, or a salt thereof, in an amount effective to inhibit a retroviral aspartyl protease.

6. A compound of the formula I according to claim 1 having the designation 1-[p-(N,N-diethylamino)phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane, or a salt thereof.

7. A compound of the formula I according to claim 1 which is 1-[p-(N,N-diethylamino)phenyl]-4(S)-hydroxy-5(S)-2,5-bis[N-(N-methoxycarbony-(L)-tert-leucyl)amino]-6-phenyl-2-azahexane, or a salt thereof.

8. A compound of the formula I according to claim 1, which is selected from the compounds 1-[p-(N,N-diethylamino)phenyl]-4(S)-hydroxy-2-[N-(N-methoxycarbonyl-(L)-valyl)amino]-5(S)-[N-(N-methoxycarbonyl-(L)-tert-leucyl)amino]-6-phenyl-2-azahexane;

1-[p-(N,N-diethylamino)phenyl]-4(S)-hydroxy-2-[N-(N-methoxycarbonyl-(L)-isoleucyl)amino]-5(S)-[N-(N-methoxycarbonyl-(L)-tert-leucyl)amino]-6-phenyl-2-azahexane;

1-[p-(N,N-diethylamino)phenyl]-4(S)-hydroxy-2-[N-(N-methoxycarbonyl-(L)-isoleucyl)amino]-5(S)-[N-(N-methoxycarbonyl-(L)-valyl)amino]-6-phenyl-2-azahexane;

1-[p-(N,N-diethylamino)phenyl]-4(S)-hydroxy-2-[N-(N-methoxycarbonyl-(L)-valyl)amino]-5(S)-[N-(N-methoxycarbonyl-(L)-isoleucyl)amino]-6-phenyl-2-azahexane;

1-[p-(N,N-diethylamino)phenyl]-4(S)-hydroxy-5(S)-2,5-bis[N-(N-methoxycarbonyl-(L)-isoleucyl)amino]-6-phenyl-2-azahexane;

1-[p-(pyrrolidin-1-yl)phenyl]-4(S)-hydroxy-2-[N-(N-methoxycarbonyl-(L)-valyl)amino]-5(S)-[N-(N-methoxycarbonyl-(L)-tert-leucyl)amino]-6-phenyl-2-azahexane;

1-[p-(pyrrolidin-1-yl)phenyl]-4(S)-hydroxy-2-[N-(N-methoxycarbonyl-(L)-isoleucyl)amino]-5(S)-[N-(N-methoxycarbonyl-(L)-tert-leucyl)amino]-6-phenyl-2-azahexane;

1-[p-(pyrrolidin-1-yl)phenyl]4(S)-hydroxy-5(S)-2,5-bis[N-(N-methoxycarbonyl-(L)-tert-leucyl)amino]-6-phenyl-2-azahexane;

1-[p-(pyrrolidin-1-yl)phenyl]-4(S)-hydroxy-2-[N-(N-methoxycarbonyl-(L)-tert-leucyl)amino]-5(S)-[N-(N-methoxycarbonyl-(L)-valyl)amino]-6-phenyl-2-azahexane;

1-[p-(pyrrolidin-1-yl)phenyl]-4(S)-hydroxy-5(S)-2,5-bis[N-(N-methoxycarbonyl-(L)-isoleucyl)amino]-6-phenyl-2-azahexane;

1-[p-(pyrrolidin-1-yl)phenyl]-4(S)-hydroxy-2-[N-(N-methoxycarbonyl-(L)-valyl)amino]-5(S)-[N-(N-methoxycarbonyl-(L)-isoleucyl)amino]-6-phenyl-2-azahexane;

1-[p-(1,2,4-triazol-4-yl)phenyl]-4(S)-hydroxy-2-[N-(N-methoxycarbonyl-(L)-isoleucyl)amino]-5(S)-[N-(N-methoxycarbonyl-(L)-valyl)amino]-6-phenyl-2-azahexane;

1-[p-(1,2,4-triazol-1-yl)phenyl]-4(S)-hydroxy-2-[N-(N-methoxycarbonyl-(L)-tert-leucyl)amino]-5(S)-5(S)-[N-(N-methoxycarbonyl-(L)-valyl)amino]-6-phenyl-2-azahexane;

1-[p-(4-methylpiperazin-1-yl)phenyl]-4(S)-hydroxy-5(S)-2,5-bis[N-(N-methoxycarbonyl-(L)-valyl)amino]-6-phenyl-2-azahexane;

1-[p-(4-methylpiperazin-1-yl)phenyl]-4(S)-hydroxy-2-N-(N-methoxycarbonyl-(L)-tert-leucyl)amino-5(S)-[N-(N-methoxycarbonyl-(L)-valyl)amino]-6-phenyl-2-azahexane; and 1-[p-(4-methylpiperazin-1-yl)phenyl]-4(S)-hydroxy-2-N-(N-methoxycarbonyl-(L)-isoleucyl)amino-5(S)-[N-(N-methoxycarbonyl-(L)-valyl)amino]-6-phenyl-2-azahexane, or a salt thereof, provided at least one salt-forming group is present.

9. A method of inhibiting a retroviral aspartate protease comprising administering to a homeothermic subject in need thereof a compound of formula I according to claim 1, or a salt thereof, for a time and under conditions effective to inhibit the retroviral aspartyl protease.

10. A process for preparing a compound of the formula I,

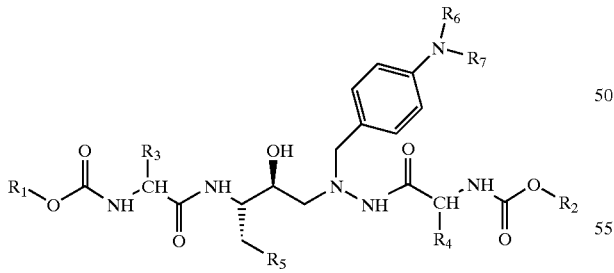

or a salt thereof,
in which $R_1$ and $R_2$ are, independently of each other, lower alkyl or lower alkoxy-lower alkyl;
$R_3$ and $R_4$ are, independently of each other, sec-lower alkyl or tert-lower alkyl;
$R_5$ is phenyl or cyclohexyl; and
$R_6$ and $R_7$ are, independently of each other, lower alkyl or, together with the linking nitrogen atom, pyrrolidino, piperidino, 4-lower alkylpiperidino, 1,2,4-triazol-1-yl or 1,2,4-triazol-4-yl, wherein said process is selected from the group consisting of process 1, process 2, process 3, process 4, process 5 and process 6,
wherein process 1 comprises
a) reacting a hydrazine derivative of the formula

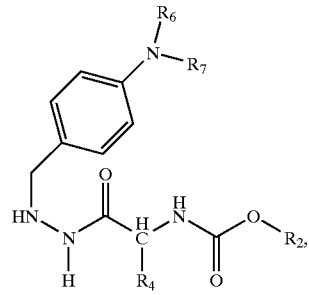

(III)

in which the radicals $R_2$, $R_4$, $R_6$ and $R_7$ have the meanings given for compounds of the formula I, with an epoxide of the formula

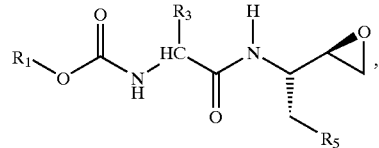

(IV)

in which the radicals $R_1$, $R_3$ and $R_5$ have the meanings given for compounds of the formula I for a time and under conditions effective to form a reaction product;
b) removing any protecting groups that may be present in the reaction product of step (a), thereby forming the compound of formula I;
c) isolating the compound of formula I;
d) optionally, converting the compound of formula I into a first salt, and subsequently isolating the first salt;
e) optionally, converting the first salt of the compound of formula I into a second salt of the compound of formula I, and subsequently isolating the second salt; and
f) optionally, converting the second salt of the compound of formula I back into the compound of formula I, and isolating the compound of formula I; and wherein process 2 comprises
a) condensing a hydrazine derivative of the formula

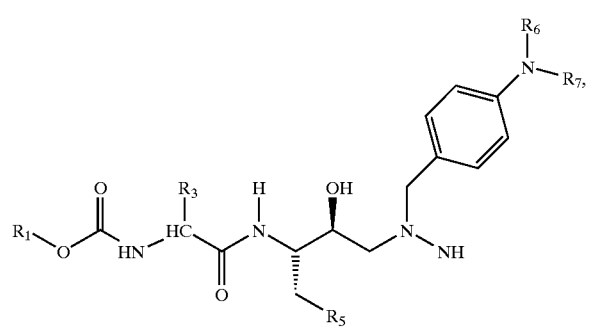

(V)

in which the radicals $R_1$, $R_3$, $R_5$, $R_6$ and $R_7$ have the meanings given for compounds of the formula I, with an acid of the formula

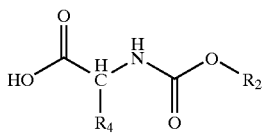
(VI)

or a reactive acid derivative thereof, in which the radicals $R_2$ and $R_4$ have the meanings given for compounds of the formula I for a time and under conditions effective to form a reaction product;

b) removing any protecting groups that may be present in the reaction product of step (a), thereby forming the compound of formula I;

c) isolating the compound of formula I;

d) optionally, converting the compound of formula I into a first salt thereof, and subsequently isolating the first salt;

e) optionally, converting the first salt of the compound of formula I into a second salt of the compound of formula I, and subsequently isolating the second salt; and f) optionally converting the second salt of the compound of formula I back into the compound of formula I, and isolating the compound of formula I; wherein process 3 comprises a) condensing a hydrazine derivative of the formula

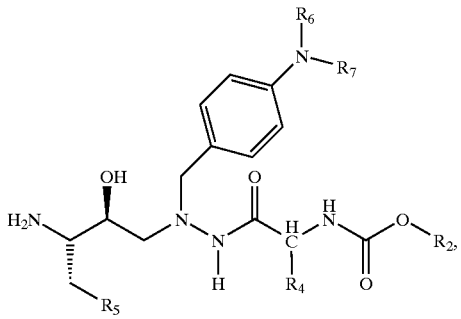
(VII)

in which the radicals $R_2$, $R_4$, $R_5$, $R_6$ and $R_7$ have the meanings given for compounds of the formula I, with an acid of the formula

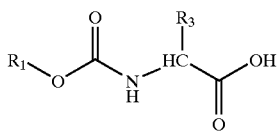
(VIII)

or a reactive acid derivative thereof, in which $R_1$ and $R_3$ have the meanings given for compounds of the formula I for a time and under conditions effective to form a reaction product;

b) removing any protecting groups that may be present in the reaction product of step (a), thereby forming the compound of formula I;

c) isolating the compound of formula I;

d) optionally, converting the compound of formula I into a first salt thereof, and subsequently isolating the first salt;

e) optionally, converting the first salt of the compound of formula I into a second salt of the compound of formula I, and subsequently isolating the second salt; and f) optionally converting the second salt of the compound of formula I back into the compound of formula I, and isolating the compound of formula I; and wherein process 4 comprises a) condensing a hydrazine derivative of the formula

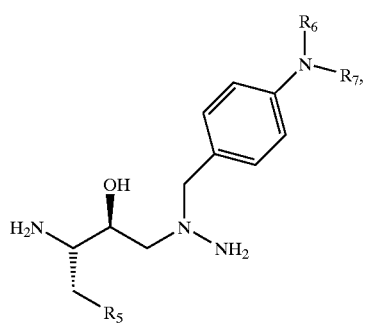
(IX)

in which $R_5$, $R_6$ and $R_7$ have the meanings given for compounds of the formula I, with an acid of the formula

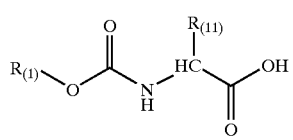
(VIIIa)

or a reactive acid derivative thereof, in which $R_{(I)}$ and $R_{(II)}$, respectively, have the meanings given in formula I for $R_1$ and $R_2$ and $R_3$ and $R_4$, respectively, with the pairs $R_1$ and $R_2$ and also $R_3$ and $R_4$ in each case being two identical radicals for a time and under conditions effective to form a reaction product;

b) removing any protecting groups that may be present in the reaction product of step (a), thereby forming the compound of formula I;

c) isolating the compound of formula I;

d) optionally, converting the compound of formula I into a first salt thereof, and subsequently isolating the first salt;

e) optionally, converting the first salt of the compound of formula I into a second salt of the compound of formula I, and subsequently isolating the second salt; and f) optionally converting the second salt of the compound of formula I back into the compound of formula I, and isolating the compound of formula I; and wherein process 5 comprises a) reacting a hydrazine derivative of the formula I',

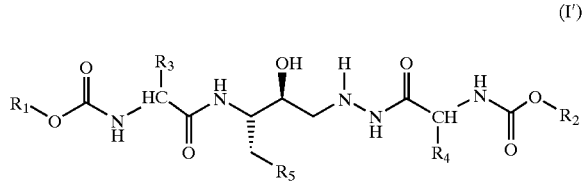
(I')

in which the radicals $R_1$, $R_2$, $R_3$, $R_4$ and $R_5$ have the meanings given for compounds of the formula I, with a compound of the formula X,

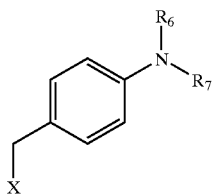
(X)

in which X is a leaving group and $R_6$ and $R_7$ have the meanings given for compounds of the formula I for a time and under conditions effective to form a reaction product;

b) removing any protecting groups that may be present in the reaction product of step (a), thereby forming the compound of formula I;

c) isolating the compound of formula I;

d) optionally, converting the compound of formula I into a first salt thereof, and subsequently isolating the first salt;

e) optionally, converting the first salt of the compound of formula I into a second salt of the compound of formula I, and subsequently isolating the second salt; and f) optionally converting the second salt of the compound of formula I back into the compound of formula I, and isolating the compound of formula I; and wherein process 6 comprises a) reacting a hydrazine derivative of the formula I',

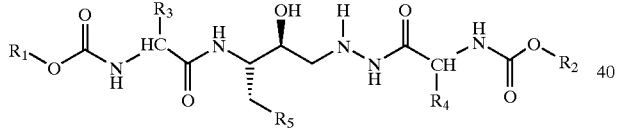
(I')

in which the radicals $R_1$, $R_2$, $R_3$, $R_4$ and $R_5$ have the meanings given for compounds of the formula I, with an aldehyde of the formula X*,

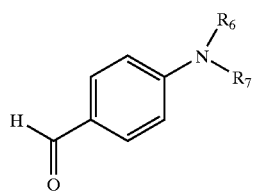
(X*)

in which $R_6$ and $R_7$ have the meanings given for compounds of the formula I, or a reactive derivative thereof with reductive alkylation for a time and under conditions effective to form a reaction product;

b) removing any protecting groups that may be present in the reaction product of step (a), thereby forming the compound of formula I;

c) isolating the compound of formula I;

d) optionally, converting the compound of formula I into a first salt thereof, and subsequently isolating the first salt;

e) optionally, converting the first salt of the compound of formula I into a second salt of the compound of formula I, and subsequently isolating the second salt; and f) optionally converting the second salt of the compound of formula I back into the compound of formula I, and isolating the compound of formula I.

11. The process of claim 10 wherein the compound of formula (I) or the first salt is in the form of two or more stereoisomers.

12. The process of claim 11, further comprising the step of resolving said stereoisomers.

* * * * *

SEQUENCE LISTING

```
<160> NUMBER OF SEQ ID NOS:  2

<210> SEQ ID NO 1
<211> LENGTH: 20
<212> TYPE: PRT
<213> ORGANISM: Artificial Sequence
<220> FEATURE:
<223> OTHER INFORMATION: artificial substrate

<400> SEQUENCE: 1

Arg Arg Ser Asn Gln Val Ser Gln Asn Tyr Pro Ile Val Gln Asn Ile
1               5                   10                  15

Gln Gly Arg Arg
            20

<210> SEQ ID NO 2
<211> LENGTH: 8
<212> TYPE: PRT
<213> ORGANISM: Artificial Sequence
<220> FEATURE:
<223> OTHER INFORMATION: artificial substrate
<221> NAME/KEY: SITE
<222> LOCATION: (1)...(1)
<223> OTHER INFORMATION: (4-(4-dimethylaminophenylazo)benzoyl-gamma-
      amino-butyryl group
```

-continued

```
<221> NAME/KEY: SITE
<222> LOCATION: (8)...(8)
<223> OTHER INFORMATION: 5-(2-aminoethylamino)-1-naphthalenesulfonic
      acid group

<400> SEQUENCE: 2

Ser Gln Asn Tyr Pro Ile Val Gln
1               5
```